(12) United States Patent
Rapp

(10) Patent No.: US 7,199,279 B2
(45) Date of Patent: *Apr. 3, 2007

(54) RECOMBINANT PROMOTERS IN AVIAN CELLS

(75) Inventor: Jeffrey C. Rapp, Athens, GA (US)

(73) Assignee: AviGenics, Inc., Athens, GA (US)

( * ) Notice: Subject to any disclaimer, the term of this patent is extended or adjusted under 35 U.S.C. 154(b) by 341 days.

This patent is subject to a terminal disclaimer.

(21) Appl. No.: 10/114,739

(22) Filed: Apr. 1, 2002

(65) Prior Publication Data

US 2003/0140363 A1 Jul. 24, 2003

Related U.S. Application Data

(63) Continuation-in-part of application No. 09/922,549, filed on Aug. 3, 2001, now Pat. No. 7,176,300.

(60) Provisional application No. 60/351,550, filed on Jan. 25, 2002, provisional application No. 60/280,004, filed on Mar. 30, 2001.

(51) Int. Cl.
- C12N 5/06 (2006.01)
- C07H 21/04 (2006.01)
- A01K 67/027 (2006.01)

(52) U.S. Cl. ............ 800/19; 435/349; 536/24.1

(58) Field of Classification Search ............ 536/23.1, 536/23.4, 24.1; 435/69.1, 320.1, 235.1, 6, 435/325, 252.3
See application file for complete search history.

(56) References Cited

U.S. PATENT DOCUMENTS

| | | | |
|---|---|---|---|
| 4,237,224 A | 12/1980 | Cohen et al. | |
| 4,603,112 A | 7/1986 | Paoletti et al. | |
| 4,722,848 A | 2/1988 | Paoletti et al. | |
| 4,769,330 A | 9/1988 | Paoletti et al. | |
| 5,174,993 A | 12/1992 | Paoletti et al. | |
| 5,175,384 A | 12/1992 | Krimpenfort et al. | |
| 5,338,683 A | 8/1994 | Paoletti et al. | |
| 5,494,807 A | 2/1996 | Paoletti et al. | |
| 5,505,941 A | 4/1996 | Paoletti et al. | |
| 5,580,859 A | 12/1996 | Felgner et al. | |
| 5,589,466 A | 12/1996 | Felgner et al. | |
| 5,591,639 A | 1/1997 | Bebbington | |
| 5,731,178 A | 3/1998 | Sippel et al. | |

FOREIGN PATENT DOCUMENTS

| | | |
|---|---|---|
| WO | WO 91/06309 | 11/1989 |
| WO | WO 92/06180 | 10/1990 |
| WO | WO 92/19749 | 5/1991 |

(Continued)

OTHER PUBLICATIONS

Alberts et al (1994). Molecular Biology of the Cell 3rd ed. Garland Publishing, New York pp. 6 and 227.*

(Continued)

*Primary Examiner*—Daniel M. Sullivan
*Assistant Examiner*—Laura McGillem
(74) *Attorney, Agent, or Firm*—Kyle D. Yesland

(57) ABSTRACT

The invention provides for cells containing nucleic acids which include lysozyme gene expression controlling region nucleotide sequences which typically are linked to a polynucleotide encoding a heterologous polypeptide.

60 Claims, 32 Drawing Sheets

| | | |
|---|---|---|
| 5pLMAR2<br>TGCCGCCTTCTTTGATATTC | SEQ ID NO: 1 | |
| LE-6.1kbrev1<br>TTGGTGGTAAGGCCYTTTTG | SEQ ID NO: 2 | |
| Lys-6.1<br>CTGGCAAGCTGTCAAAAACA | SEQ ID NO: 3 | |
| LysE1rev<br>CAGCTCACATCGTCCAAAGA | SEQ ID NO: 4 | |
| LYSBSU<br>CCCCCCCTAAGGCAGCCAGGGGCAGGAAGCAAA | SEQ ID NO: 5 | |
| SalItoNotI<br>TCGAGCGGCCGC | SEQ ID NO: 6 | |
| T7<br>TAATACGACTCACTATAGGG | SEQ ID NO: 7 | |
| lys6lenfor1<br>CGTGGTGATCAAATCTTTGTG | SEQ ID NO: 8 | |
| lys6lenrev1<br>AGGAGGGCACAGTAGGGATC | SEQ ID NO: 9 | |
| 5MARfor1<br>GTGGCCTGTGTCTGTGCTT | SEQ ID NO: 10 | |
| IFN-3rev<br>AACTCCTCTTGAGGAAAGCC | SEQ ID NO: 11 | |
| lys001rev<br>TCCTGTTTGGGGATGAATGGT | SEQ ID NO: 12 | |
| lys002for<br>CTCTCAGAATGCCCAACTCC | SEQ ID NO: 13 | |
| lys003for<br>TGTATTGGTCTCCCTCCTGC | SEQ ID NO: 14 | |
| lys005for<br>TGTTGAAATTGCAGTGTGGC | SEQ ID NO: 15 | |
| lys006rev<br>TGACAATGCAAATTTGGCTC | SEQ ID NO: 16 | |

FOREIGN PATENT DOCUMENTS

| WO | WO 92/20316 | 5/1991 |
| --- | --- | --- |
| WO | WO 92/22635 | 6/1991 |
| WO | WO 93/04701 | 9/1991 |
| WO | WO 93/25234 | 6/1992 |
| WO | WO 94/06920 | 9/1992 |
| WO | WO 94/11524 | 11/1992 |
| WO | WO 97/47739 | 6/1996 |
| WO | WO 99/19472 | 10/1997 |
| WO | WO 00/11151 | 8/1998 |
| WO | WO 00/56932 | 3/1999 |

OTHER PUBLICATIONS von Kries JP, Phi-Van L, Diekmann S, Stratling WH. 1990. A non-curved chicken lysozyme 5' matrix attachment site is 3' followed by a strongly curved DNA sequence. Nucleic Acids Res. Jul. 11;18(13):3881-5.*

Grewal T, Theisen M, Borgmeyer U, Grussenmeyer T, Rupp RA, Stief A, Qian F, Hecht A, Sippel AE. 1992. The -6.1-kilobase chicken lysozyme enhancer is a multifactorial complex containing several cell-type-specific elements. Mol Cell Biol. May.12(5):2339-50.*

Renkawitz R, Schutz G, von der Ahe D, Beato M. 1984. Sequences in the promoter region of the chicken lysozyme gene required for steroid regulation and receptor binding. Cell. Jun.37(2):503-10.*

Stumph WE, Hodgson CP, Tsai MJ, O'Malley BW. 1984. Genomic structure and possible retroviral origin of the chicken CR1 repetitive DNA sequence family. Proc Natl Acad Sci U S A. Nov.81(21):6667-71.*

Wagstrom EA, Yoon KJ, Zimmerman JJ. 2000. Immune components in porcine mammary secretions. Viral Immunol. 2000;13(3):383-97.*

Jung A, Sippel AE, Grez M, Schutz G. 1980. Exons encode functional and structural units of chicken lysozyme. Proc Natl Acad Sci U S A. Oct. 77(10):5759-63.*

Exons encode functional and structural units of chicken lysozyme, Jung et al; PNAS USA, 77:5759-5763, (Oct. 1980).

An Initiation Zone of Chromosomal DNA Replication at the Chicken Lysozyme Gene Locus*, Loc Phi-van et al; The Journal of Biological Chemistry 273:18300-18307 (1998).

The matrix attachment regions of the chicken lysozyme gene co-map with the boundaries of the chromatin domain, Phi-Van and Stratling; EMBO Journal 7:655-664 (1988).

Lysozme Level in Blood Serum of Newly Hatched White Leghorn Chickens, Rosolowska-Huszcz; Bulletin De L'academie Polonaise Des Sciences, 26:891-894 (1978).

Prerequisites for tissue specific and position independent expression of a gene locus in transgenic mice, Bonifer et al; J Mol Med 74:663-671(1996).

A nuclear DNA attachment element mediates elevated and position-independent gene activity, Stief et al; Nature 341:343-345(Sep. 1989).

Tissue specific and position independent expression of the complete gene domain for chicken lysozyme in transgenic mice, Bonifer et al; EMBO Journal 9:2843-2848 (1990).

Stopped at the border: boundaries and insulators, Bell and Felsenfeld; Current Opinion in Genetics & Development,9:191-198(1999).

Dissection of the Ability of the Chicken Lysozyme Gene 5' Matrix Attachment Region To Stimulate Transgene Expression and To Dampen Position Effects; Phi-Van and Stratling; Biochemistry 35:10735-10742(1996).

Activity of two different silencer elements of the chicken lysozyme gene can be compensated by enhancer elements, Baniahmad et al; EMBO Journal 6:2297-2303(1987).

The lysozyme enhancer: cell-specific activation of the chicken lysozyme gene by a far-upstream DNA element, Theisen et al; EMBO Journal 5:719-724(1986).

The Chicken Lysozyme Locus as a Paradigm for the Complex Developmental Regulation of Eukaryotic Gene Loci, Bonifer et al; Journal of Biological Chemistry 272:26075-26078(1997).

A progesterone responsive element maps to the far upstream steroid dependent DNase hypersensitive site of chicken lysozyme chromatin, Hecht et al; EMBO Journal 7:2063-2073(1988).

Chromatin fine structure profiles for a developmentally regulated gene: reorganization of the lysozyme locus before trans-activator binding and gene expression, Kontaraki et al.; Genes & Developmental 14:210 2122(2000).

The Far Upstream Chicken Lysozyme Enhancer at-6.1 Kilobase, by Interacting with NF-M, Mediates Lipopolysaccharide-induced Expression of the Chicken Lysozyme Gene in Chicken Myelomonocytic Cells, Goethe and Phi Van; Journal of Biological Chemistry 269:31302-31309(1994).

Chromatin Domains Constitute Regulatory Units for the Control of Eukaryotic genes, Sippel et al;Cold Spring Harbor Symposia on Quantitative Biology, 58:37-44(1993).

Dynamic Changes in the Chromatin of the Chicken Lysozyme Gene Domain During Differentiation of Multipotent Progenitors to Macrophages, Huber et al; DNA and Cell Biology 14:397-402(1995).

Alternative sets of DNase I-hypersensitive sites characterize the various functional states of the chicken lysozyme gene, Fritton et al; Nature 311:163-165(Sep. 1984).

Reduced Position Effect in Mature Transgenic Plants conferred by the Chicken Lysozyme Matrix-Associated Region, Mlynarova et al;The Plant Cell 6:417-426(1994).

Development of position-independent expression vectors and their transfer into transgenic fish, Caldovic and Hackett; Mol. Marine Biol. and Biotech 4:51-61(1995).

Chicken repeat 1(CR1) elements, which define an ancient family of vertebrate non-LTR retrotransposons, contain two closely spaced open reading frames, Haas et al; Gene 197:305-309(1997).

Sequence conservation in avian CR1: An interspersed repetitive DNA family evolving under functional constraints, Chen et al; PNAS USA 88:5814-5818 (Jul. 1991).

Position-independent expression of transgenic in zebrafish, Caldovic et al; Transgenic Research 8:321-334(1999).

Lysozyme in Hen Blood Serum, Sato and Watanabe, Poultry Science 55:1749-1756(1976).

"Lysozyme gene Activity in Chicken Macrophages is Controlled by Positive and Negative Regulatory Elements"GG2, Steiner et al; Nucleic Acids Research, 15:4163-4178 (1987).

Chong, et al., The chicken lysozyme chromatin domain contains a second, widely expressed gene, *Nucleic Acids Research*, vol. 30, No. 2 (2002) 463-467.

* cited by examiner

5pLMAR2
TGCCGCCTTCTTTGATATTC                         SEQ ID NO: 1

LE-6.1kbrev1
TTGGTGGTAAGGCCTTTTTG                         SEQ ID NO: 2

Lys-6.1
CTGGCAAGCTGTCAAAAACA                         SEQ ID NO: 3

LysE1rev
CAGCTCACATCGTCCAAAGA                         SEQ ID NO: 4

LYSBSU
CCCCCCCCTAAGGCAGCCAGGGGCAGGAAGCAAA           SEQ ID NO: 5

SalItoNotI
TCGAGCGGCCGC                                 SEQ ID NO: 6

T7
TAATACGACTCACTATAGGG                         SEQ ID NO: 7 lys61enfor1
CGTGGTGATCAAATCTTTGTG                        SEQ ID NO: 8 lys61enrev1
AGGAGGGCACAGTAGGGATC                         SEQ ID NO: 9

5MARfor1
GTGGCCTGTGTCTGTGCTT                          SEQ ID NO: 10

IFN-3rev
AACTCCTCTTGAGGAAAGCC                         SEQ ID NO: 11 lys001rev
TCCTGTTTGGGATGAATGGT                         SEQ ID NO: 12 lys002for
CTCTCAGAATGCCCAACTCC                         SEQ ID NO: 13 lys003for
TGTATTGGTCTCCCTCCTGC                         SEQ ID NO: 14 lys005for
TGTTGAAATTGCAGTGTGGC                         SEQ ID NO: 15 lys006rev
TGACAATGCAAATTTGGCTC                         SEQ ID NO: 16

*Fig. 1a* lys007for
GATATCCTTGCAGTGCCCAT                    SEQ ID NO: 17 lys008rev
GGACAAGCAAGTGCATCAGA                    SEQ ID NO: 18 lys009for
CTGATGTGCTTCAGCTCTGC                    SEQ ID NO: 19 lys010rev
TCCATGGTGGTCAAACAGAA                    SEQ ID NO: 20 lys011for
GTACTAGACCAGGCAGCCCA                    SEQ ID NO: 21 lys012rev
GTGGGAAGTACCACATTGGC                    SEQ ID NO: 22 lys013for
CGCTCAGGAGAAAGTGAACC                    SEQ ID NO: 23 lys014rev
CGGTTTTGCCTTTGTGTTTT                    SEQ ID NO: 24 lys015rev
AAATGCTCGATTTCATTGGG                    SEQ ID NO: 25 lys016rev
GCCAATCAGACTGCATTTCA                    SEQ ID NO: 26 lys017rev
AACCGCTGAATGGAACAGTC                    SEQ ID NO: 27 lys018for
ACACGCACATATTTTGCTGG                    SEQ ID NO: 28 lys019rev
CAGGAGCTGGATTCCTTCAG                    SEQ ID NO: 29 lys020for
AAAGGATGCAGTCCCAAATG                    SEQ ID NO: 30 lys021rev
GCCCCTAGACTCCATCTTCC                    SEQ ID NO: 31 lys022rev
ATTTGCTGTGGTGGATGTGA                    SEQ ID NO: 32

*Fig. 1b* lys024for
CCTTGCAGTCCTTGGTTTGT                        SEQ ID NO: 33 lys025rev
ATGATCCTTCTGATGGGCTG                        SEQ ID NO: 34 lys026rev
ACAGTGATAGCACAAGGGGG                        SEQ ID NO: 35 lys027rev
GTAAACAGCTGCAACAGGCA                        SEQ ID NO: 36 lys028rev
CAACACAAAAGTTGGACAGCA                       SEQ ID NO: 37 lys029rev
TTTGCAGATGAGACGTTTGC                        SEQ ID NO: 38 lys030rev
CCACAAGTTCTTGTTTGGGC                        SEQ ID NO: 39 lys031rev
ATCAATCCATGCCAGTAGCC                        SEQ ID NO: 40 lys032rev
GTTTAAGGCCCCTTCCAATC                        SEQ ID NO: 41 lys033for
GAGAGGGGGTTGGGTGTATT                        SEQ ID NO: 42 lys034for
ACAGTGGAAGCATTCAAGGG                        SEQ ID NO: 43 lys037for
CCAATGCCTTTGGTTCTGAT                        SEQ ID NO: 44 lys038for
AAAACACAAAGGCAAAACCG                        SEQ ID NO: 45 lys039rev
CTAAGCCTCGCCAGTTTCAA                        SEQ ID NO: 46 lys040rev
TGCCATGAAAACCCTACTGA                        SEQ ID NO: 47 lys041for
GGAATGTACCCTCAGCTCCA                        SEQ ID NO: 48

*Fig. 1c* lys042rev
CCTCTTTAGGAGGCCAGCTT                    SEQ ID NO: 49 lys043rev
AAGATGATCAGAGGGCTGGA                    SEQ ID NO: 50 lys044rev
GCAGCGCTGGTAATCTTCAT                    SEQ ID NO: 51 lys045for
CTTCAGATCCCAGGAAGTGC                    SEQ ID NO: 52 lys046for
TTCCTGCCTTACATTCTGGG                    SEQ ID NO: 53 lys047for
CCCACTGCAGGCTTAGAAAG                    SEQ ID NO: 54 lys048for
AGTTCTCCATAGCGGCTGAA                    SEQ ID NO: 55 lys051for
TGCATCCTTCAGCACTTGAG                    SEQ ID NO: 56 lys052rev
GCAGGAGGGAGACCAATACA                    SEQ ID NO: 57 lys053for
TGCACAAGGATGTCTGGGTA                    SEQ ID NO: 58 lys054for
TCCTAGCAACTGCGGATTTT                    SEQ ID NO: 59 lys056for
TCTTCCATGTTGGTGACAGC                    SEQ ID NO: 60 lys058for
CCCCCTTGTGCTATCACTGT                    SEQ ID NO: 61 lys059for
CTGACAGACATCCCAGCTCA                    SEQ ID NO: 62 lys060for
AAGTTGTGCTTCTGCGTGTG                    SEQ ID NO: 63 lys061for
TTGTTCCTGCTGTTCCTCCT                    SEQ ID NO: 64

*Fig. 1d*

SEQ ID NO: 65

```
TGCCGCCTTC TTTGATATTC ACTCTGTTGT ATTTCATCTC TTCTTGCCGA TGAAAGGATA 60
TAACAGTCTG TATAACAGTC TGTGAGGAAA TACTTGGTAT TTCTTCTGAT CAGTGTTTTT 120
ATAAGTAATG TTGAATATTG GATAAGGCTG TGTGTCCTTT GTCTTGGGAG ACAAAGCCCA 180
CAGCAGGTGG TGGTTGGGGT GGTGGCAGCT CAGTGACAGG AGAGGTTTTT TTGCCTGTTT 240
TTTTTTTTTT TTTTTTTTTT AAGTAAGGTG TTCTTTTTTC TTAGTAAATT TTCTACTGGA 300
CTGTATGTTT TGACAGGTCA GAAACATTTC TTCAAAAGAA GAACCTTTTG GAAACTGTAC 360
AGCCCTTTTC TTTCATTCCC TTTTTGCTTT CTGTGCCAAT GCCTTTGGTT CTGATTGCAT 420
TATGGAAAAC GTTGATCGGA ACTTGAGGTT TTTATTTATA GTGTGGCTTG AAAGCTTGGA 480
TAGCTGTTGT TACACGAGAT ACCTTATTAA GTTTAGGCCA GCTTGATGCT TTATTTTTTC 540
CCTTTGAAGT AGTGAGCGTT CTCTGGTTTT TTTCCTTTGA AACTGGTGAG GCTTAGATTT 600
TTCTAATGGG ATTTTTTACC TGATGATCTA GTTGCATACC CAAATGCTTG TAAATGTTTT 660
CCTAGTTAAC ATGTTGATAA CTTCGGATTT ACATGTTGTA TATACTTGTC ATCTGTGTTT 720
CTAGTAAAAA TATATGGCAT TTATAGAAAT ACGTAATTCC TGATTTCCTT TTTTTTTATC 780
TCTATGCTCT GTGTGTACAG GTCAAACAGA CTTCACTCCT ATTTTATTT ATAGAATTTT 840
ATATGCAGTC TGTCGTTGGT TCTTGTGTTG TAAGGATACA GCCTTAAATT TCCTAGAGCG 900
ATGCTCAGTA AGGCGGGTTG TCACATGGGT TCAAATGTAA AACGGGCACG TTTGGCTGCT 960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TCAGTTGTA AAAGAATTCC GCCTATTCAT 1680
ACCATGTAAT GTAATTTTAC ACCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAG TAATATAAAA AGGACCAGGT GTTTACAAG TGAAATACAT TCCTATTTGG 1980
TAAACAGTTA CATTTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TTCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTTC 2460
AGCCTTTAGG AGACTGTTAA GCAATTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
```

*FIG. 3a*

```
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAATTC TTTCTTTTCC 5520
TGTCATGTGG GATCCCTACT GTGCCCTCCT GGTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
```

*FIG. 3b*

```
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGGACAAT CGCTTACCCC TCCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GGCTACTGGC ATGGATTGAT TACATACAAC TGTAATTTTA 9600
```

FIG. 3c

```
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGGTGCGA TCTGCCTCAG ACCCACAGCC TGGGCAGCAG GAGGACCCTG ATGCTGCTGG 12000
CTCAGATGAG GAGAATCAGC CTGTTTAGCT GCCTGAAGGA TAGGCACGAT TTTGGCTTTC 12060
CTCAAGAGGA GTTTGGCAAC CAGTTTCAGA AGGCTGAGAC CATCCCTGTG CTGCACGAGA 12120
TGATCCAGCA GATCTTTAAC CTGTTTAGCA CCAAGGATAG CAGCGCTGCT TGGGATGAGA 12180
CCCTGCTGGA TAAGTTTTAC ACCGAGCTGT ACCAGCAGCT GAACGATCTG GAGGCTTGCG 12240
TGATCCAGGG CGTGGGCGTG ACCGAGACCC CTCTGATGAA GGAGGATAGC ATCCTGGCTG 12300
TGAGGAAGTA CTTTCAGAGG ATCACCCTGT ACCTGAAGGA GAAGAAGTAC AGCCCCTGCG 12360
CTTGGGAAGT CGTGAGGGCT GAGATCATGA GGAGCTTTAG CCTGAGCACC AACCTGCAAG 12420
AGAGCTTGAG GTCTAAGGAG TAAAAGTCT AGAGTCGGGG CGGCCGGCC CTTCGAGCAG 12480
ACATGATAAG ATACATTGAT GAGTTTGGAC AAACCACAAC TAGAATGCAG TGAAAAAAT 12540
GCTTTATTTG TGAAATTTGT GATGCTATTG CTTTATTTGT AACCATTATA AGCTGCAATA 12600
AACAAGTTAA CAACAACAAT TGCATTCATT TTATGTTTCA GGTTCAGGGG GAGGTGTGGG 12660
AGGTTTTTTA AAGCAAGTAA AACCTCTACA AATGTGGTAA AATCGATAAG GATCCGTCGA 12720
GCGGCCGC                                                         12728
```

FIG. 3d

SEQ ID NO: 66

```
TGCGATCTGC CTCAGACCCA CAGCCTGGGC AGCAGGAGGA CCCTGATGCT GCTGGCTCAG   60
ATGAGGAGAA TCAGCCTGTT TAGCTGCCTG AAGGATAGGC ACGATTTTGG CTTTCCTCAA  120
GAGGAGTTTG GCAACCAGTT TCAGAAGGCT GAGACCATCC CTGTGCTGCA CGAGATGATC  180
CAGCAGATCT TTAACCTGTT TAGCACCAAG GATAGCAGCG CTGCTTGGGA TGAGACCCTG  240
CTGGATAAGT TTTACACCGA GCTGTACCAG CAGCTGAACG ATCTGGAGGC TTGCGTGATC  300
CAGGGCGTGG GCGTGACCGA GACCCCTCTG ATGAAGGAGG ATAGCATCCT GGCTGTGAGG  360
AAGTACTTTC AGAGGATCAC CCTGTACCTG AAGGAGAAGA AGTACAGCCC CTGCGCTTGG  420
GAAGTCGTGA GGGCTGAGAT CATGAGGAGC TTTAGCCTGA GCACCAACCT GCAAGAGAGC  480
TTGAGGTCTA AGGAGTAA 498
```

Fig. 4

SEQ ID NO: 67

```
TGCCGCCTTC TTTGATATTC ACTCTGTTGT ATTTCATCTC TTCTTGCCGA TGAAAGGATA  60
TAACAGTCTG TATAACAGTC TGTGAGGAAA TACTTGGTAT TTCTTCTGAT CAGTGTTTTT 120
ATAAGTAATG TTGAATATTG GATAAGGCTG TGTGTCCTTT GTCTTGGGAG ACAAAGCCCA 180
CAGCAGGTGG TGGTTGGGGT GGTGGCAGCT CAGTGACAGG AGAGGTTTTT TTGCCTGTTT 240
TTTTTTTTTT TTTTTTTTTT AAGTAAGGTG TTCTTTTTC TTAGTAAATT TTCTACTGGA 300
CTGTATGTTT TGACAGGTCA GAAACATTTC TTCAAAAGAA GAACCTTTTG GAAACTGTAC 360
AGCCCTTTTC TTTCATTCCC TTTTTGCTTT CTGTGCCAAT GCCTTTGGTT CTGATTGCAT 420
TATGGAAAAC GTTGATCGGA ACTTGAGGTT TTTATTTATA GTGTGGCTTG AAAGCTTGGA 480
TAGCTGTTGT TACACGAGAT ACCTTATTAA GTTTAGGCCA GCTTGATGCT TTATTTTTC 540
CCTTTGAAGT AGTGAGCGTT CTCTGGTTTT TTTCCTTTGA AACTGGTGAG GCTTAGATTT 600
TTCTAATGGG ATTTTTTACC TGATGATCTA GTTGCATACC CAAATGCTTG TAAATGTTTT 660
CCTAGTTAAC ATGTTGATAA CTTCGGATTT ACATGTTGTA TATACTTGTC ATCTGTGTTT 720
CTAGTAAAAA TATATGGCAT TTATAGAAAT ACGTAATTCC TGATTTCCTT TTTTTTTATC 780
TCTATGCTCT GTGTGTACAG GTCAAACAGA CTTCACTCCT ATTTTTATTT ATAGAATTTT 840
ATATGCAGTC TGTCGTTGGT TCTTGTGTTG TAAGGATACA GCCTTAAATT TCCTAGAGCG 900
ATGCTCAGTA AGGCGGGTTG TCACATGGGT TCAAATGTAA AACGGGCACG TTTGGCTGCT 960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TTCAGTTGTA AAAGAATTCC GCCTATTCAT 1680
ACCATGTAAT GTAATTTTAC ACCCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAAG TAATATAAAA AGGACCAGGT GTTTTACAAG TGAAATACAT TCCTATTTGG 1980
TAAACAGTTA CATTTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TTCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTTC 2460
AGCCTTTAGG AGACTGTTAA GCAATTTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
```

FIG. 5a

```
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA ATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAATTC TTTCTTTTCC 5520
TGTCATGTGG GATCCCTACT GTGCCCTCCT GGTTTTACGT TACCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTAAT TATGTCAATA ACTGGCTTAG ATTTGGAAAT GAGAGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
```

FIG. 5b

```
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT CCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CCAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGACAAT CGCTTACCCC TCCCTGCTGG CTGCCCTGT TTTGATGCAG 7140
CCCAGGGTAC TGTTGGCCTT TCAGGCTCCC AGACCCCTTG CTGATTTGT TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
```

*FIG. 5c*

```
GTATGAACTC AGGTCTCTCG GGCTACTGGC ATGGATTGAT TACATACAAC TGTAATTTTA 9600
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGG                                                              11945
```

FIG. 5d

SEQ ID NO: 68

```
AAAGTCTAGAGTCGGGGCGGCCGGCCGCTTCGAGCAGACATGATAAGATACATTGATGAG   60
TTTGGACAAACCACAACTAGAATGCAGTGAAAAAAATGCTTTATTTGTGAAATTTGTGAT  120
GCTATTGCTTTATTTGTAACCATTATAAGCTGCAATAAACAAGTTAACAACAACAATTGC  180
ATTCATTTTATGTTTCAGGTTCAGGGGGAGGTGTGGGAGGTTTTTTAAAGCAAGTAAAAC  240
CTCTACAAATGTGGTAAAATCGATAAGGATCCGTCGAGCGGCCGC  285
```

*FIG. 6*

SEQ ID NO: 69

```
   1  CGCGTGGTAG GTGGCGGGGG GTTCCCAGGA GAGCCCCCAG CGCGGACGGC
  51  AGCGCCGTCA CTCACCGCTC CGTCTCCCTC CGCCCAGGGT CGCCTGGCGC
 101  AACCGCTGCA AGGGCACCGA CGTCCAGGCG TGGATCAGAG CTGCCGGCT
 151  GTGAGGAGCT GCCGCGCCCG GCCCGCCCGC TGCACAGCCG CCGCTTTGC
 201  GAGCGCGACG CTACCCGCTT GGCAGTTTTA AACGCATCCC TCATTAAAAC
 251  GACTATACGC AAACGCCTTC CCGTCGGTCC GCGTCTCTTT CCGCCGCCAG
 301  GGCGACACTC GCGGGGAGGG CGGGAAGGGG GCCGGGCGGG AGCCCGCGGC
 351  CAACCGTCGC CCCGTGACGG CACCGCCCCG CCCCGTGAC GCGGTGCGGG
 401  CGCCGGGGCC GTGGGGCTGA GCGCTGCGGC GGGGCCGGGC CGGGCCGGGG
 451  CGGGAGCTGA GCGCGGCGCG GCTGCGGGCG GCGCCCCCTC CGGTGCAATA
 501  TGTTCAAGAG AATGGCTGAG TTCGGGCCTG ACTCCGGGGG CAGGGTGAAG
 551  GTGCGGCGCG GCGGAGGGA CGGGGCGGGC GCGGGGCCGC CCGGCGGGTG
 601  CCGGGGCCTC TGCCGGCCCG CCCGGCTCGG GCTGCTGCGG CGCTTACGGG
 651  CGCGCTTCTC GCCGCTGCCG CTTCTCTTCT CTCCCGCGCA AGGGCGTCAC
 701  CATCGTGAAG CCGGTAGTGT ACGGGAACGT GGCGCGGTAC TTCGGGAAGA
 751  AGAGGGAGGA GGACGGGCAC ACGCATCAGT GGACGGTTTA CGTGAAGCCC
 801  TACAGGAACG AGGTAGGGCC CGAGCGCGTC GGCCGCCGTT CTCGGAGCGC
 851  CGGAGCCGTC AGCGCCGCGC CTGGGTGCGC TGTGGGACAC AGCGAGCTTC
 901  TCTCGTAGGA CATGTCCGCC TACGTGAAAA AAATCCAGTT CAAGCTGCAC
 951  GAGAGCTACG GAATCCTCT CCGAGGTGGG TGTTGCGTCG GGGGTTTGC
1001  TCCGCTCGGT CCCGCTGAGG CTCGTCGCCC TCATCTTTCT TTCGTGCCGC
1051  AGTCGTTACC AAACCGCCGT ACGAGATCAC CGAAACGGGC TGGGGCGAAT
1101  TTGAAATCAT CATCAAGATA TTTTTCATTG ATCCAAACGA GCGACCCGTA
1151  AGTACGCTCA GCTTCTCGTA GTGCTTCCCC CGTCCTGGCG GCCCGGGGCT
1201  GGGCTGCTCG CTGCTGCCGG TCACAGTCCC GCCAGCCGCG GAGCTGACTG
1251  AGCTCCCTTT CCCGGGACGT GTGCTCTGTG TTCGGTCAGC GAGGCTATCG
1301  GGAGGGCTTT GGCTGCATTT GGCTTCTCTG GCGCTTAGCG CAGGAGCACG
1351  TTGTGCTACG CCTGAACTAC AGCTGTGAGA AGGCCGTGGA AACCGCTCTC
1401  AAACTGATTT ATTGGCGAAA TGGCTCTAAA CTAAATCGTC TCCTCTCTTT
1451  GGAAATGCTT TAGAGAAGGT CTCTGTGGTA GTTCTTATGC ATCTATCCTA
1501  AAGCACTTGG CCAGACAATT TAAAGACATC AAGCAGCATT TATAGCAGGC
1551  ACGTTTAATA ACGAATACTG AATTTAAGTA ACTCTGCTCA CGTTGTATGA
1601  CGTTTATTTT CGTATTCCTG AAAGCCATTA AATCCTGTG CAGTTGTTTA
1651  GTAAGAACAG CTGCCACTGT TTTGTATCTA GGAGATAACT GGTGTTTCCC
1701  TACAGTTCTC AAGCTGATAA AACTCTGTCT TTGTATCTAG GTAACCCTGT
1751  ATCACTTGCT GAAGCTTTTT CAGTCTGACA CCAATGCAAT CCTGGGAAAG
1801  AAAACTGTAG TTTCTGAATT CTATGATGAA ATGGTATGAA AATTTTAATG
1851  TCAACCGAGC CTGACTTTAT TTAAAAAAAA TTATTGATGG TGCTGTGTAT
1901  TTTGGTCCTT CCTTAGATAT TTCAAGATCC TACTGCCATG ATGCAGCAAC
1951  TGCTAACGAC GTCCCGTCAG CTGACACTTG GTGCTTACAA GCATGAAACA
2001  GAGTGTAAGT GCAAAATGAG GATACCTTCG CCGACCGTCA TTCACTACTA
2051  ATGTTTTCTG TGGGATGTGA TCGTACAGTG AGTTTGGCTG TGTGAAATTT
2101  GAATAGCTTG GTATTGGCAG TGATGACGTG ATCGATGCCT TGCTTATCAT
2151  GTTTGAAATG AAGTAGAATA AATGCAGCCT GCTTTATTTG AGATAGTTTG
2201  GTTCATTTTA TGGAATGCAA GCAAAGATTA TACTTCCTCA CTGAATTGCA
```

Fig. 7a

```
2251  CTGTCCAAAG GTGTGAAATG TGTGGGGATC TGGAGGACCG TGACCGAGGG
2301  ACATTGGATC GCTATCTCCC ATTTCTTTTG CTGTTACCAG TTCAGATTTT
2351  CTTTTCACCT AGTCTTTAAT TCCCAGGGTT TTGTTTTTTC CTTGGTCATA
2401  GTTTTTGTTT TTCACTCTGG CAAATGATGT TGTGAATTAC ACTGCTTCAG
2451  CCACAAAACT GATGGACTGA ATGAGGTCAT CAAACAAACT TTTCTTCTTC
2501  CGTATTTCCT TTTTTTTCCC CCACTTATCA TTTTACTGC TGTTGTTGAG
2551  TCTGTAAGGC TAAAAGTAAC TGTTTTGTGC TTTTTCAGGA CGTGTGCTTT
2601  CCAAATTACT GCCACATATA TAAAGAAAGG TTGGAATTTT AAAGATAATT
2651  CATGTTTCTT CTTCTTTTTT GCCACCACAG TTGCAGATCT TGAAGTAAAA
2701  ACCAGGGAAA AGCTGGAAGC TGCCAAAAAG AAACCAGTT TTGAAATTGC
2751  TGAGCTTAAA GAAAGGTTAA AAGCAAGTCG TGAAACCATC AACTGCTTAA
2801  AGAGTGAAAT CAGAAAACTC GAAGAGGATG ATCAGTCTAA AGATATGTGA
2851  TGAGTGTTGA CTTGGCAGGG AGCCTATAAT GAGAATGAAA GGACTTCAGT
2901  CGTGGAGTTG TATGCGTTCT CTCCAATTCT GTAACGGAGA CTGTATGAAT
2951  TTCATTTGCA AATCACTGCA GTGTGTGACA ACTGACTTTT TATAAATGGC
3001  AGAAAACAAG AATGAATGTA TCCTCATTTT ATAGTTAAAA TCTATGGGTA
3051  TGTACTGGTT TATTTCAAGG AGAATGGATC GTAGAGACTT GGAGGCCAGA
3101  TTGCTGCTTG TATTGACTGC ATTTGAGTGG TGTAGGAACA TTTTGTCTAT
3151  GGTCCCGTGT TAGTTTACAG AATGCCACTG TTCACTGTTT TGTTTTGTAT
3201  TTTACTTTTT CTACTGCAAC GTCAAGGTTT TAAAAGTTGA AAATAAAACA
3251  TGCAGGTTTT TTTTAAATAT TTTTTTGTCT CTATCCAGTT TGGGCTTCAA
3301  GTATTATTGT TAACAGCAAG TCCTGATTTA AGTCAGAGGC TGAAGTGTAA
3351  TGGTATTCAA GATGCTTAAG TCTGTTGTCA GCAAACAAA AGAGAAAACT
3401  TCATAAAATC AGGAAGTTGG CATTTCTAAT AACTTCTTTA TCAACAGATA
3451  AGAGTTTCTA GCCCTGCATC TACTTTCACT TATGTAGTTG ATGCCTTTAT
3501  ATTTTGTGTG TTTGGATGCA GGAAGTGATT CCTACTCTGT TATGTAGATA
3551  TTCTATTTAA CACTTGTACT CTGCTGTGCT TAGCCTTTCC CCATGAAAAT
3601  TCAGCGGCTG TAAATCCCCC TCTTCTTTTG TAGCCTCATA CAGATGGCAG
3651  ACCCTCAGGC TTATAAAGGC TTGGGCATCT TCTTTACTGC TTTGAGATTC
3701  TGTGTTGCAG TAACCTCTGC CAGAGAGGAG AAAAGCCCCA CAAACCTCAT
3751  CCCCTTCTTC TATAGCAATC AGTATTACTA ATGCTTTGAG AACAGAGCAC
3801  TGGTTTGAAA CGTTTGATAA TTAGCATTTA ACATGGCTTG GTAAAGATGC
3851  AGAACTGAAA CAGCTGTGAC AGTATGAACT CAGTATGGAG ACTTCATTAA
3901  GACAAACAGC TGTTAAAATC AGGCATGTTT CATTGAGGAG GACGGGGCAA
3951  CTTGCACCAG TGGTGCCCAC ACAAATCCTT CCTGGCGCTG CAGACCAATT
4001  TTTCTGGCAT TCTGACTGCC GTTGCTGCTG GTCACAGAGA GCAACTATTT
4051  TTATCAGCCA CAGGCAATTT GCTTGTAGTA TTTTCCAAGT GTTGTAGGTA
4101  AGTATAAATG CATCGGCTCC AGAGCACTTT GAGTATACTT ATTAAAAACA
4151  TAAATGAAAG ACAAATTAGC TTTGCTTGGG TGCACAGAAC ATTTTTAGTT
4201  CCAGCCTGCT TTTTGGTAGA AGCCCTCTTC TGAGGCTAGA ACTGACTTTG
4251  ACAAGTAGAG AAACTGGCAA CGGAGCTATT GCTATCGAAG GATCCTTGTT
4301  AACAAAGTTA ATCGTCTTTT AAGGTTTGGT TTATTCATTA AATTTGCTTT
4351  TAAGCTGTAG CTGAAAAAGA ACGTGCTGTC TTCCATGCAC CAGGTGGCAG
4401  CTCTGTGCAA AGTGCTCTCT GGTCTCACCA GCCTTTTAAT TGCCGGGATT
4451  CTGGCACGTC TGAGAGGGCT CAGACTGGCT TCGTTTGTTT GAACAGCGTG
4501  TACTGCTTTC TGTAGACATG GCCGGTTTCT CTCCTGCAGC TTATGAAACT
4551  GTTCACACTG AACACACTGG AACAGGTTGC CCAAGGAGGC CGTGGATGCC
4601  CCATCCCTGG AGGCATTCAA GGCCAGGCTG GATGTGGCTC TGGGCAGCCT
```

*Fig. 7b*

```
4651  GGTCTGGTGG TTGGCGATCC TGCACATAGC AGCGGGGTTG AAACTCGATG
4701  ATCACTGTGG TCCTTTTCAA CCCAGGCTAT TCTATGATTC TATGATTCAA
4751  CAGCAAATCA TATGTACTGA GAGAGGAAAC AAACACAAGT GCTACTGTTT
4801  GCAAGTTTTG TTCATTTGGT AAAAGAGTCA GGTTTTAAAA TTCAAAATCT
4851  GTCTGGTTTT GGTGTTTTTT TTTTTTATT TATTATTTCT TTGGGGTTCT
4901  TTTTGATGCT TTATCTTTCT CTGCCAGGAC TGTGTGACAA TGGGAACGAA
4951  AAAGAACATG CCAGGCACTG TCCTGGATTG CACACGCTGG TTGCACTCAG
5001  TAGCAGGCTC AGAACTGCCA GTCTTTCCAC AGTATTACTT TCTAAACCTA
5051  ATTTTAATAG CGTTAGTAGA CTTCCATCAC TGGGCAGTGC TTAGTGAATG
5101  CTCTGTGTGA ACGTTTTACT TATAAGCATG TTGGAAGTTT TGATGTTCCT
5151  GGATGCAGTA GGGAAGGACA GATTAGCTAT GTGAAAAGTA GATTCTGAGT
5201  ATCGGGGTTA CAAAAGTAT AGAAACGATG AGAAATTCTT GTTGTAACTA
5251  ATTGGAATTT CTTTAAGCGT TCACTTATGC TACATTCATA GTATTTCCAT
5301  TTAAAAGTAG GAAAAGGTAA AACGTGAAAT CGTGTGATTT TCGGATGGAA
5351  CACCGCCTTC CTATGCACCT GACCAACTTC CAGAGGAAAA GCCTATTGAA
5401  AGCCGAGATT AAGCCACCAA AAGAACTCAT TTGCATTGGA ATATGTAGTA
5451  TTTGCCCTCT TCCTCCCGGG TAATTACTAT ACTTTATAGG GTGCTTATAT
5501  GTTAAATGAG TGGCTGGCAC TTTTTATTCT CACAGCTGTG GGGAATTCTG
5551  TCCTCTAGGA CAGAAACAAT TTTAATCTGT TCCACTGGTG ACTGCTTTGT
5601  CAGCACTTCC ACCTGAAGAG ATCAATACAC TCTTCAATGT CTAGTTCTGC
5651  AACACTTGGC AAACCTCACA TCTTATTTCA TACTCTCTTC ATGCCTATGC
5701  TTATTAAAGC AATAATCTGG GTAATTTTTG TTTTAATCAC TGTCCTGACC
5751  CCAGTGATGA CCGTGTCCCA CCTAAAGCTC AATTCAGGTC CTGAATCTCT
5801  TCAACTCTCT ATAGCTAACA TGAAGAATCT TCAAAAGTTA GGTCTGAGGG
5851  ACTTAAGGCT AACTGTAGAT GTTGTTGCCT GGTTTCTGTG CTGAAGGCCG
5901  TGTAGTAGTT AGAGCATTCA ACCTCTAG
```

*Fig. 7c*

SEQ ID NO: 74

```
   1  TGCCGCCTTCTTTGATATTCACTCTGTTGTATTTCATCTCTTCTTGCCGA
  51  TGAAAGGATATAACAGTCTGTATAACAGTCTGTGAGGAAATACTTGGTAT
 101  TTCTTCTGATCAGTGTTTTATAAGTAATGTTGAATATTGGATAAGGCTG
 151  TGTGTCCTTTGTCTTGGGAGACAAAGCCCACAGCAGGTGGTGGTTGGGT
 201  GGTGGCAGCTCAGTGACAGGAGAGGTTTTTTGCCTGTTTTTTTTTTT
 251  TTTTTTTTTAAGTAAGGTGTTCTTTTTCTTAGTAAATTTTCTACTGGA
 301  CTGTATGTTTTGACAGGTCAGAAACATTTCTTCAAAAGAAGAACCTTTTG
 351  GAAACTGTACAGCCCTTTTCTTTCATTCCCTTTTGCTTTCTGTGCCAAT
 401  GCCTTTGGTTCTGATTGCATTATGGAAAACGTTGATCGGAACTTGAGGTT
 451  TTTATTTATAGTGTGGCTTGAAAGCTTGGATAGCTGTTGTTACACGAGAT
 501  ACCTTATTAAGTTTAGGCCAGCTTGATGCTTTATTTTTTCCCTTTGAAGT
 551  AGTGAGCGTTCTCTGGTTTTTTCCTTTGAAACTGGTGAGGCTTAGATTT
 601  TTCTAATGGGATTTTTACCTGATGATCTAGTTGCATACCCAAATGCTTG
 651  TAAATGTTTTCCTAGTTAACATGTTGATAACTTCGGATTTACATGTTGTA
 701  TATACTTGTCATCTGTGTTTCTAGTAAAATATATGGCATTTATAGAAAT
 751  ACGTAATTCCTGATTTCCTTTTTTTTATCTCTATGCTCTGTGTGTACAG
 801  GTCAAACAGACTTCACTCCTATTTTTATTTATAGAATTTTATATGCAGTC
 851  TGTCGTTGGTTCTTGTGTTGTAAGGATACAGCCTTAAATTTCCTAGAGCG
 901  ATGCTCAGTAAGGCGGGTTGTCACATGGGTTCAAATGTAAAACGGGCACG
 951  TTTGGCTGCTGCCTTCCCGAGATCCAGGACACTAAACTGCTTCTGCACTG
1001  AGGTATAAATCGCTTCAGATCCAGGGAAGTGCAGATCCACGTGCATATT
1051  CTTAAAGAAGAATGAATACTTTCTAAATATTTTGGCATAGGAAGCAAGC
1101  TGCATGGATTTGTTTGGGACTTAAATTATTTTGGTAACGGAGTGCATAGG
1151  TTTTAAACACAGTTGCAGCATGCTAACGAGTCACAGCGTTTATGCAGAAG
1201  TGATGCCTGGATGCCTGTTGCAGCTGTTTACGGCACTGCCTTGCAGTGAG
1251  CATTGCAGATAGGGTGGGGTGCTTTGTGTCGTGTTCCCACACGCTGCCA
1301  CACAGCCACCTCCCGGAACACATCTCACCTGCTGGGTACTTTTCAAACCA
1351  TCTTAGCAGTAGTAGATGAGTTACTATGAAACAGAGAAGTTCCTCAGTTG
1401  GATATTCTCATGGGATGTCTTTTTTCCCATGTTGGGCAAAGTATGATAAA
1451  GCATCTCTATTTGTAAATTATGCACTTGTTAGTTCCTGAATCCTTTCTAT
1501  AGCACCACTTATTGCAGCAGGTGTAGGCTCTGGTGTGGCCTGTGTCTGTG
1551  CTTCAATCTTTTAAAGCTTCTTTGGAAATACACTGACTTGATTGAAGTCT
1601  CTTGAAGATAGTAAACAGTACTTACCTTTGATCCCAATGAAATCGAGCAT
1651  TTCAGTTGTAAAAGAATTCCGCCTATTCATACCATGTAATGTAATTTTAC
1701  ACCCCAGTGCTGACACTTTGGAATATATTCAAGTAATAGACTTTGGCCT
1751  CACCCTCTTGTGTACTGTATTTTGTAATAGAAATATTTTAAACTGTGCA
1801  TATGATTATTACATTATGAAAGAGACATTCTGCTGATCTTCAAATGTAAG
1851  AAAATGAGGAGTGCGTGTGCTTTTATAAATACAAGTGATTGCAAATTAGT
1901  GCAGGTGTCCTTAAAAAAAAAAAAAAAAGTAATATAAAAAGGACCAGGT
1951  GTTTTACAAGTGAAATACATTCCTATTTGGTAAACAGTTACATTTTATG
2001  AAGATTACCAGCGCTGCTGACTTTCTAAACATAAGGCTGTATTGTCTTCC
2051  TGTACCATTGCATTTCCTCATTCCCAATTTGCACAAGGATGTCTGGGTAA
```

*Fig. 8a*

```
2101  ACTATTCAAGAAATGGCTTTGAAATACAGCATGGGAGCTTGTCTGAGTTG
2151  GAATGCAGAGTTGCACTGCAAATGTCAGGAAATGGATGTCTCTCAGAAT
2201  GCCCAACTCCAAAGGATTTTATATGTGTATATAGTAAGCAGTTTCCTGAT
2251  TCCAGCAGGCCAAAGAGTCTGCTGAATGTTGTGTTGCCGGAGACCTGTAT
2301  TTCTCAACAAGGTAAGATGGTATCCTAGCAACTGCGGATTTTAATACATT
2351  TTCAGCAGAAGTACTTAGTTAATCTCTACCTTTAGGGATCGTTTCATCAT
2401  TTTTAGATGTTATACTTGAAATACTGCATAACTTTAGCTTTCATGGGTT
2451  CCTTTTTTTCAGCCTTTAGGAGACTGTTAAGCAATTGCTGTCCAACTTT
2501  TGTGTTGGTCTTAAACTGCAATAGTAGTTTACCTTGTATTGAAGAAATAA
2551  AGACCATTTTTATATTAAAAATACTTTTGTCTGTCTTCATTTTGACTTG
2601  TCTGATATCCTTGCAGTGCCCATTATGTCAGTTCTGTCAGATATTCAGAC
2651  ATCAAAACTTAACGTGAGCTCAGTGGAGTTACAGCTGCGGTTTGATGCT
2701  GTTATTATTTCTGAAACTAGAAATGATGTTGTCTTCATCTGCTCATCAAA
2751  CACTTCATGCAGAGTGTAAGGCTAGTGAGAAATGCATACATTTATTGATA
2801  CTTTTTTAAAGTCAACTTTTTATCAGATTTTTTTTCATTTGGAAATATA
2851  TTGTTTTCTAGACTGCATAGCTTCTGAATCTGAAATGCAGTCTGATTGGC
2901  ATGAAGAAGCACAGCACTCTTCATCTTACTTAAACTTCATTTGGAATGA
2951  AGGAAGTTAAGCAAGGGCACAGGTCCATGAAATAGAGACAGTGCGCTCAG
3001  GAGAAAGTGAACCTGGATTTCTTTGGCTAGTGTTCTAAATCTGTAGTGAG
3051  GAAAGTAACACCCGATTCCTTGAAAGGGCTCCAGCTTTAATGCTTCCAAA
3101  TTGAAGGTGGCAGGCAACTTGGCCACTGGTTATTTACTGCATTATGTCTC
3151  AGTTTCGCAGCTAACCTGGCTTCTCCACTATTGAGCATGGACTATAGCCT
3201  GGCTTCAGAGGCCAGGTGAAGGTTGGGATGGGTGGAAGGAGTGCTGGGCT
3251  GTGGCTGGGGGGACTGTGGGGACTCCAAGCTGAGCTTGGGGTGGGCAGCA
3301  CAGGGAAAAGTGTGGGTAACTATTTTAAGTACTGTGTTGCAAACGTCTC
3351  ATCTGCAAATACGTAGGGTGTGTACTCTCGAAGATTAACAGTGTGGGTTC
3401  AGTAATATATGGATGAATTCACAGTGGAAGCATTCAAGGGTAGATCATCT
3451  AACGACACCAGATCATCAAGCTATGATTGGAAGCGGTATCAGAAGAGCGA
3501  GGAAGGTAAGCAGTCTTCATATGTTTTCCCTCCACGTAAAGCAGTCTGGG
3551  AAAGTAGCACCCCTTGAGCAGAGACAAGGAAATAATTCAGGAGCATGTGC
3601  TAGGAGAACTTTCTTGCTGAATTCTACTTGCAAGAGCTTTGATGCCTGGC
3651  TTCTGGTGCCTTCTGCAGCACCTGCAAGGCCCAGAGCCTGTGGTGAGCTG
3701  GAGGGAAAGATTCTGCTCAAGTCCAAGCTTCAGCAGGTCATTGTCTTTGC
3751  TTCTTCCCCCAGCACTGTGCAGCAGAGTGGAACTGATGTCGAAGCCTCCT
3801  GTCCACTACCTGTTGCTGCAGGCAGACTGCTCTCAGAAAAGAGAGCTAA
3851  CTCTATGCCATAGTCTGAAGGTAAATGGGTTTTAAAAAGAAAACACAA
3901  AGGCAAAACCGGCTGCCCCATGAGAAGAAAGCAGTGGTAAACATGGTAGA
3951  AAAGGTGCAGAAGCCCCCAGGCAGTGTGACAGGCCCCTCCTGCCACCTAG
4001  AGGCGGGAACAAGCTTCCTGCCTAGGGCTCTGCCCGCGAAGTGCGTGTT
4051  TCTTTGGTGGGTTTTGTTTGGCGTTTGGTTTTGAGATTTAGACACAAGGG
4101  AAGCCTGAAGGAGGTGTTGGGCACTATTTTGGTTTGTAAAGCCTGTACT
4151  TCAAATATATATTTTGTGAGGGAGTGTAGCGAATTGGCCAATTTAAAATA
4201  AAGTTGCAAGAGATTGAAGGCTGAGTAGTTGAGAGGGTAACACGTTTAAT
4251  GAGATCTTCTGAAACTACTGCTTCTAAACACTTGTTTGAGTGGTGAGACC
```

*Fig. 8b*

```
4301  TTGGATAGGTGAGTGCTCTTGTTACATGTCTGATGCACTTGCTTGTCCTT
4351  TTCCATCCACATCCATGCATTCCACATCCACGCATTTGTCACTTATCCCA
4401  TATCTGTCATATCTGACATACCTGTCTCTTCGTCACTTGGTCAGAAGAAA
4451  CAGATGTGATAATCCCCAGCCGCCCCAAGTTTGAGAAGATGGCAGTTGCT
4501  TCTTTCCCTTTTTCCTGCTAAGTAAGGATTTTCTCCTGGCTTTGACACCT
4551  CACGAAATAGTCTTCCTGCCTTACATTCTGGGCATTATTTCAAATATCTT
4601  TGGAGTGCGCTGCTCTCAAGTTTGTGTCTTCCTACTCTTAGAGTGAATGC
4651  TCTTAGAGTGAAAGAGAAGGAAGAGAAGATGTTGGCCGCAGTTCTCTGAT
4701  GAACACACCTCTGAATAATGGCCAAAGGTGGGTGGGTTTCTCTGAGGAAC
4751  GGGCAGCGTTTGCCTCTGAAAGCAAGGAGCTCTGCGGAGTTGCAGTTATT
4801  TTGCAACTGATGGTGGAACTGGTGCTTAAAGCAGATTCCCTAGGTTCCCT
4851  GCTACTTCTTTTCCTTCTTGGCAGTCAGTTTATTTCTGACAGACAAACAG
4901  CCACCCCACTGCAGGCTTAGAAAGTATGTGGCTCTGCCTGGGTGTGTTA
4951  CAGCTCTGCCCTGGTGAAAGGGGATTAAAACGGGCACCATTCATCCCAAA
5001  CAGGATCCTCATTCATGGATCAAGCTGTAAGGAACTTGGGCTCCAACCTC
5051  AAAACATTAATTGGAGTACGAATGTAATTAAAACTGCATTCTCGCATTCC
5101  TAAGTCATTTAGTCTGGACTCTGCAGCATGTAGGTCGGCAGCTCCCACTT
5151  TCTCAAAGACCACTGATGGAGGAGTAGTAAAAATGGAGACCGATTCAGAA
5201  CAACCAACGGAGTGTTGCCGAAGAAACTGATGGAAATAATGCATGAATTG
5251  TGTGGTGGACATTTTTTTAAATACATAAACTACTTCAAATGAGGTCGGA
5301  GAAGGTCAGTGTTTATTAGCAGCCATAAAACCAGGTGAGCGAGTACCAT
5351  TTTTCTCTACAAGAAAACGATTCTGAGCTCTGCGTAAGTATAAGTTCTC
5401  CATAGCGGCTGAAGCTCCCCCCTGGCTGCCTGCCATCTCAGCTGGAGTGC
5451  AGTGCCATTTCCTTGGGGTTTCTCTCACAGCAGTAATGGGACAATACTTC
5501  ACAAAAATTCTTTCTTTTCCTGTCATGTGGGATCCCTACTGTGCCCTCCT
5551  GGTTTTACGTTACCCCCTGACTGTTCCATTCAGCGGTTTGGAAAGAGAAA
5601  AAGAATTTGGAAATAAAACATGTCTACGTTATCACCTCCTCCAGCATTTT
5651  GGTTTTTAATTATGTCAATAACTGGCTTAGATTTGGAAATGAGAGGGGGT
5701  TGGGTGTATTACCGAGGAACAAAGGAAGGCTTATATAAACTCAAGTCTTT
5751  TATTTAGAGAACTGGCAAGCTGTCAAAAACAAAAAGGCCTTACCACCAAA
5801  TTAAGTGAATAGCCGCTATAGCCAGCAGGGCCAGCACGAGGGATGGTGCA
5851  CTGCTGGCACTATGCCACGGCCTGCTTGTGACTCTGAGAGCAACTGCTTT
5901  GGAAATGACAGCACTTGGTGCAATTTCCTTTGTTTCAGAATGCGTAGAGC
5951  GTGTGCTTGGCGACAGTTTTTCTAGTTAGGCCACTTCTTTTTTCCTTCTC
6001  TCCTCATTCTCCTAAGCATGTCTCCATGCTGGTAATCCCAGTCAAGTGAA
6051  CGTTCAAACAATGAATCCATCACTGTAGGATTCTCGTGGTGATCAAATCT
6101  TTGTGTGAGGTCTATAAAATATGGAAGCTTATTTATTTTCGTTCTTCCA
6151  TATCAGTCTTCTCTATGACAATTCACATCCACCACAGCAAATTAAGGTG
6201  AAGGAGGCTGGTGGGATGAAGAGGGTCTTCTAGCTTTACGTTCTTCCTTG
6251  CAAGGCCACAGGAAAATGCTGAGAGCTGTAGAATACAGCCTGGGGTAAGA
6301  AGTTCAGTCTCCTGCTGGGACAGCTAACCGCATCTTATAACCCCTTCTGA
6351  GACTCATCTTAGGACCAAATAGGGTCTATCTGGGGTTTTGTTCCTGCTG
6401  TTCCTCCTGGAAGGCTATCTCACTATTTCACTGCTCCACGGTTACAAAC
6451  CAAAGATACAGCCTGAATTTTTTCTAGGCCACATTACATAAATTTGACCT
```

*Fig. 8c*

```
6501  GGTACCAATATTGTTCTCTATATAGTTATTTCCTTCCCCACTGTGTTTAA
6551  CCCCTTAAGGCATTCAGAACAACTAGAATCATAGAATGGTTTGGATTGGA
6601  AGGGGCCTTAAACATCATCCATTTCCAACCCTCTGCCATGGGCTGCTTGC
6651  CACCCACTGGCTCAGGCTGCCCAGGGCCCCATCCAGCCTGGCCTTGAGCA
6701  CCTCCAGGGATGGGGCACCCACAGCTTCTCTGGGCAGCCTGTGCCAACAC
6751  CTCACCACTCTCTGGGTAAAGAATTCTCTTTTAACATCTAATCTAAATCT
6801  CTTCTCTTTTAGTTTAAAGCCATTCCTCTTTTCCCGTTGCTATCTGTCC
6851  AAGAAATGTGTATTGGTCTCCCTCCTGCTTATAAGCAGGAAGTACTGGAA
6901  GGCTGCAGTGAGGTCTCCCCACAGCCTTCTCTTCTCCAGGCTGAACAAGC
6951  CCAGCTCCTTCAGCCTGTCTTCGTAGGAGATCATCTTAGTGGCCCTCCTC
7001  TGGACCCATTCCAACAGTTCCACGGCTTTCTTGTGGAGCCCCAGGTCTGG
7051  ATGCAGTACTTCAGATGGGCCTTACAAGGCAGAGCAGATGGGGACAAT
7101  CGCTTACCCTCCCTGCTGGCTGCCCTGTTTGATGCAGCCCAGGGTAC
7151  TGTTGGCCTTTCAGGCTCCAGACCCCTTGCTGATTTGTGTCAAGCTTTT
7201  CATCCACCAGAACCCACGCTTCCTGGTTAATACTTCTGCCCTCACTTCTG
7251  TAAGCTTGTTTCAGGAGACTTCCATTCTTTAGGACAGACTGTGTTACACC
7301  TACCTGCCCTATTCTTGCATATACATTTCAGTTCATGTTTCCTGTAAC
7351  AGGACAGAATATGTATTCCTCTAACAAAATACATGCAGAATTCCTAGTG
7401  CCATCTCAGTAGGGTTTTCATGGCAGTATTAGCACATAGTCAATTTGCTG
7451  CAAGTACCTTCCAAGCTGCGGCCTCCCATAAATCCTGTATTTGGGATCAG
7501  TTACCTTTTGGGGTAAGCTTTTGTATCTGCAGAGACCCTGGGGGTTCTGA
7551  TGTGCTTCAGCTCTGCTCTGTTCTGACTGCACCATTTTCTAGATCACCCA
7601  GTTGTTCCTGTACAACTTCCTTGTCCTCCATCCTTTCCCAGCTTGTATCT
7651  TTGACAAATACAGGCCTATTTTGTGTTTGCTTCAGCAGCCATTTAATTC
7701  TTCAGTGTCATCTTGTTCTGTTGATGCCACTGGAACAGGATTTTCAGCAG
7751  TCTTGCAAAGAACATCTAGCTGAAAACTTTCTGCCATTCAATATTCTTAC
7801  CAGTTCTTCTTGTTTGAGGTGAGCCATAAATTACTAGAACTTCGTCACTG
7851  ACAAGTTTATGCATTTTATTACTTCTATTATGTACTTACTTTGACATAAC
7901  ACAGACACGCACATATTTGCTGGGATTTCCACAGTGTCTCTGTGTCCTT
7951  CACATGGTTTTACTGTCATACTTCCGTTATAACCTTGGCAATCTGCCCAG
8001  CTGCCCATCACAAGAAAGAGATTCCTTTTTATTACTTCTCTTCAGCCA
8051  ATAAACAAATGTGAGAAGCCCAAACAAGAACTTGTGGGCAGGCTGCCA
8101  TCAAGGGAGAGACAGCTGAAGGGTTGTGTAGCTCAATAGAATTAAGAAAT
8151  AATAAAGCTGTGTCAGACAGTTTTGCCTGATTTATACAGGCACGCCCAA
8201  GCCAGAGAGGCTGTCTGCCAAGGCCACCTTGCAGTCCTTGGTTTGTAAGA
8251  TAAGTCATAGGTAACTTTTCTGGTGAATTGCGTGGAGAATCATGATGGCA
8301  GTTCTTGCTGTTTACTATGGTAAGATGCTAAATAGGAGACAGCAAAGTA
8351  ACACTTGCTGCTGTAGGTGCTCTGCTATCCAGACAGCGATGGCACTCGCA
8401  CACCAAGATGAGGGATGCTCCAGCTGACGGATGCTGGGGCAGTAACAGT
8451  GGGTCCCATGCTGCCTGCTCATTAGCATCACCTCAGCCCTCACCAGCCCA
8501  TCAGAAGGATCATCCCAAGCTGAGGAAAGTTGCTCATCTTCTTCACATCA
8551  TCAAACCTTTGGCCTGACTGATGCCTCCCGGATGCTTAAATGTGGTCACT
8601  GACATCTTTATTTTTCTATGATTTCAAGTCAGAACCTCCGGATCAGGAGG
8651  GAACACATAGTGGGAATGTACCCTCAGCTCCAAGGCCAGATCTTCCTTCA
```

*Fig. 8d*

```
 8701  ATGATCATGCATGCTACTTAGGAAGGTGTGTGTGTGTGAATGTAGAATTG
 8751  CCTTTGTTATTTTTTCTTCCTGCTGTCAGGAACATTTTGAATACCAGAGA
 8801  AAAAGAAAAGTGCTCTTCTTGGCATGGGAGGAGTTGTCACACTTGCAAAA
 8851  TAAAGGATGCAGTCCCAAATGTTCATAATCTCAGGGTCTGAAGGAGGATC
 8901  AGAAACTGTGTATACAATTTCAGGCTTCTCTGAATGCAGCTTTTGAAAGC
 8951  TGTTCCTGGCCGAGGCAGTACTAGTCAGAACCCTCGGAAACAGGAACAAA
 9001  TGTCTTCAAGGTGCAGCAGGAGGAAACACCTTGCCCATCATGAAAGTGAA
 9051  TAACCACTGCCGCTGAAGGAATCCAGCTCCTGTTTGAGCAGGTGCTGCAC
 9101  ACTCCCACACTGAAACAACAGTTCATTTTATAGGACTTCCAGGAAGGAT
 9151  CTTCTTCTTAAGCTTCTTAATTATGGTACATCTCCAGTTGGCAGATGACT
 9201  ATGACTACTGACAGGAGAATGAGGAACTAGCTGGGAATATTTCTGTTTGA
 9251  CCACCATGGAGTCACCCATTTCTTTACTGGTATTTGGAAATAATAATTCT
 9301  GAATTGCAAAGCAGGAGTTAGCGAAGATCTTCATTTCTTCCATGTTGGTG
 9351  ACAGCACAGTTCTGGCTATGAAAGTCTGCTTACAAGGAAGAGGATAAAAA
 9401  TCATAGGGATAATAAATCTAAGTTTGAAGACAATGAGGTTTTAGCTGCAT
 9451  TTGACATGAAGAAATTGAGACCTCTACTGGATAGCTATGGTATTTACGTG
 9501  TCTTTTTGCTTAGTTACTTATTGACCCCAGCTGAGGTCAAGTATGAACTC
 9551  AGGTCTCTCGGGCTACTGGCATGGATTGATTACATACAACTGTAATTTTA
 9601  GCAGTGATTAGGGTTTATGAGTACTTTTGCAGTAAATCATAGGGTTAGT
 9651  AATGTTAATCTCAGGGAAAAAAAAAAAAGCCAACCCTGACAGACATCCC
 9701  AGCTCAGGTGGAAATCAAGGATCACAGCTCAGTGCGGTCCCAGAGAACAC
 9751  AGGGACTCTTCTCTTAGGACCTTTATGTACAGGGCCTCAAGATAACTGAT
 9801  GTTAGTCAGAAGACTTTCCATTCTGGCCACAGTTCAGCTGAGGCAATCCT
 9851  GGAATTTTCTCTCCGCTGCACAGTTCCAGTCATCCCAGTTTGTACAGTTC
 9901  TGGCACTTTTTGGGTCAGGCCGTGATCCAAGGAGCAGAAGTTCCAGCTAT
 9951  GGTCAGGGAGTGCCTGACCGTCCAACTCACTGCACTCAAACAAAGGCGA
10001  AACCACAAGAGTGGCTTTTGTTGAAATTGCAGTGTGGCCCAGAGGGGCTG
10051  CACCAGTACTGGATTGACCACGAGGCAACATTAATCCTCAGCAAGTGCAA
10101  TTTGCAGCCATTAAATTGAACTAACTGATACTACAATGCAATCAGTATCA
10151  ACAAGTGGTTTGGCTTGGAAGATGGAGTCTAGGGGCTCTACAGGAGTAGC
10201  TACTCTCTAATGGAGTTGCATTTGAAGCAGGACACTGTGAAAAGCTGGC
10251  CTCCTAAAGAGGCTGCTAAACATTAGGGTCAATTTTCCAGTGCACTTTCT
10301  GAAGTGTCTGCAGTTCCCCATGCAAAGCTGCCCAAACATAGCACTTCCAA
10351  TTGAATACAATTATATGCAGGCGTACTGCTTCTTGCCAGCACTGTCCTTC
10401  TCAAATGAACTCAACAAACAATTTCAAAGTCTAGTAGAAAGTAACAAGCT
10451  TTGAATGTCATTAAAAAGTATATCTGCTTTCAGTAGTTCAGCTTATTTAT
10501  GCCCACTAGAAACATCTTGTACAAGCTGAACACTGGGGCTCCAGATTAGT
10551  GGTAAAACCTACTTTATACAATCATAGAATCATAGAATGGCCTGGGTTGG
10601  AAGGGACCCCAAGGATCATGAAGATCCAACACCCCGCCACAGGCAGGGC
10651  CACCAACCTCCAGATCTGGTACTAGACCAGGCAGCCCAGGGCTCCATCCA
10701  ACCTGGCCATGAACACCTCCAGGGATGGAGCATCCACAACCTCTCTGGGC
10751  AGCCTGTGCCAGCACCTCACCACCCTCTCTGTGAAGAACTTTTCCCTGAC
10801  ATCCAATCTAAGCCTTCCTCCTTGAGGTTAGATCCACTCCCCCTTGTGC
10851  TATCACTGTCTACTCTTGTAAAAGTTGATTCTCCTCCTTTTTGGAAGGT
```

*Fig. 8e*

```
10901  TGCAATGAGGTCTCCTTGCAGCCTTCTTCTCTTCTGCAGGATGAACAAGC
10951  CCAGCTCCCTCAGCCTGTCTTTATAGGAGAGGTGCTCCAGCCCTCTGATC
11001  ATCTTTGTGGCCCTCCTCTGGACCCGCTCCAAGAGCTCCACATCTTTCCT
11051  GTACTGGGGGCCCCAGGCCTGAATGCAGTACTCCAGATGGGGCCTCAAAA
11101  GAGCAGAGTAAAGAGGGACAATCACCTTCCTCACCCTGCTGGCCAGCCCT
11151  CTTCTGATGGAGCCCTGGATACAACTGGCTTTCTGAGCTGCAACTTCTCC
11201  TTATCAGTTCCACTATTAAAACAGGAACAATACAACAGGTGCTGATGGCC
11251  AGTGCAGAGTTTTTCACACTTCTTCATTTCGGTAGATCTTAGATGAGGAA
11301  CGTTGAAGTTGTGCTTCTGCGTGTGCTTCTTCCTCCTCAAATACTCCTGC
11351  CTGATACCTCACCCCACCTGCCACTGAATGGCTCCATGGCCCCCTGCAGC
11401  CAGGGCCTGATGAACCGGCACTGCTTCAGATGCTGTTTAATAGCACAG
11451  TATGACCAAGTTGCACCTATGAATACACAAACAATGTTGCATCCTTCA
11501  GCACTTGAGAAGAAGAGCCAAATTTGCATTGTCAGGAAATGGTTTAGTAA
11551  TTCTGCCAATTAAAACTTGTTTATCTACCATGGCTGTTTTATGGCTGTT
11601  AGTAGTGGTACACTGATGATGAACAATGGCTATGCAGTAAAATCAAGACT
11651  GTAGATATTGCAACAGACTATAAAATTCCTCTGTGGCTTAGCCAATGTGG
11701  TACTTCCCACATTGTATAAGAAATTTGGCAAGTTTAGAGCAATGTTTGAA
11751  GTGTTGGGAAATTTCTGTATACTCAAGAGGGCGTTTTTGACAACTGTAGA
11801  ACAGAGGAATCAAAAGGGGGTGGGAGGAAGTTAAAAGAAGAGGCAGGTGC
11851  AAGAGAGCTTGCAGTCCCGCTGTGTGTACGACACTGGCAACATGAG<u>GTCT</u>
11901  <u>TTGCTAATCTTGGTGCTTTGCTTCCTGCCCCTGGCTGCCTTAGGGTGCGA</u>
11951  <u>TCTGCCTCAGACCCACAGCCTGGGCAGCAGGAGGACCCTGATGCTGCTGG</u>
12001  <u>CTCAGATGAGGAGAATCAGCCTGTTTAGCTGCCTGAAGGATAGGCACGAT</u>
12051  <u>TTTGGCTTTCCTCAAGAGGAGTTTGGCAACCAGTTTCAGAAGGCTGAGAC</u>
12101  <u>CATCCCTGTGCTGCACGAGATGATCCAGCAGATCTTTAACCTGTTTAGCA</u>
12151  <u>CCAAGGATAGCAGCGCTGCTTGGGATGAGACCCTGCTGGATAAGTTTTAC</u>
12201  <u>ACCGAGCTGTACCAGCAGCTGAACGATCTGGAGGCTTGCGTGATCCAGGG</u>
12251  <u>CGTGGGCGTGACCGAGACCCCTCTGATGAAGGAGGATAGCATCCTGGCTG</u>
12301  <u>TGAGGAAGTACTTTCAGAGGATCACCCTGTACCTGAAGGAGAAGAAGTAC</u>
12351  <u>AGCCCCTGCGCTTGGGAAGTCGTGAGGGCTGAGATCATGAGGAGCTTTAG</u>
12401  <u>CCTGAGCACCAACCTGCAA</u>gagagcttgaggtctaaggagtaaaaagtct
12451  agagtcggggcggCGCGTGGTAGGTGGCGGGGGGTTCCCAGGAGAGCCCC
12501  CAGCGCGGACGGCAGCGCCGTCACTCACCGCTCCGTCTCCCTCCGCCCAG
12551  GGTCGCCTGGCGCAACCGCTGCAAGGGCACCGACGTCCAGGCGTGGATCA
12601  GAGGCTGCCGGCTGTGAGGAGCTGCCGCGCCCGGCCCGCCCGCTGCACAG
12651  CCGGCCGCTTTGCGAGCGCGACGCTACCCGCTTGGCAGTTTTAAACGCAT
12701  CCCTCATTAAAACGACTATACGCAAACGCCTTCCCGTCGGTCCGCGTCTC
12751  TTTCCGCCGCCAGGGCGACACTCGCGGGAGGCGGGAAGGGGCCGGGC
12801  GGGAGCCCGCGGCCAACCGTCGCCCCGTGACGGCACCGCCCCGCCCCGT
12851  GACGCGGTGCGGGCGCCGGGCCGTGGGCTGAGCGCTGCGGCGGGGCCG
12901  GCCGGGCCGGGGCGGGAGCTGAGCGCGGCGCGGCTGCGGCGGCGCCCC
12951  CTCCGGTGCAATATGTTCAAGAGAATGGCTGAGTTCGGGCCTGACTCCGG
13001  GGGCAGGGTGAAGGTGCGGCGCGGGCGGAGGGACGGGGCGGGCGCGGGC
13051  CGCCCGGCGGGTGCCGGGGCCTCTGCCGGCCCGCCCGGCTCGGGCTGCTG
```

*Fig. 8f*

```
13101  CGGCGCTTACGGGCGCGCTTCTCGCCGCTGCCGCTTCTCTTCTCTCCCGC
13151  GCAAGGGCGTCACCATCGTGAAGCCGGTAGTGTACGGGAACGTGGCGCGG
13201  TACTTCGGGAAGAAGAGGGAGGAGGACGGGCACACGCATCAGTGGACGGT
13251  TTACGTGAAGCCCTACAGGAACGAGGTAGGGCCCGAGCGCGTCGGCCGCC
13301  GTTCTCGGAGCGCCGGAGCCGTCAGCGCCGCGCCTGGGTGCGCTGTGGGA
13351  CACAGCGAGCTTCTCTCGTAGGACATGTCCGCCTACGTGAAAAAAATCCA
13401  GTTCAAGCTGCACGAGAGCTACGGGAATCCTCTCCGAGGTGGGTGTTGCG
13451  TCGGGGGGTTTGCTCCGCTCGGTCCCGCTGAGGCTCGTCGCCCTCATCTT
13501  TCTTTCGTGCCGCAGTCGTTACCAAACCGCCGTACGAGATCACCGAAACG
13551  GGCTGGGGCGAATTTGAAATCATCATCAAGATATTTTTCATTGATCCAAA
13601  CGAGCGACCCGTAAGTACGCTCAGCTTCTCGTAGTGCTTCCCCCGTCCTG
13651  GCGGCCCGGGGCTGGGCTGCTCGCTGCTGCCGGTCACAGTCCCGCCAGCC
13701  GCGGAGCTGACTGAGCTCCCTTTCCCGGGACGTGTGCTCTGTGTTCGGTC
13751  AGCGAGGCTATCGGGAGGGCTTTGGCTGCATTTGGCTTCTCTGGCGCTTA
13801  GCGCAGGAGCACGTTGTGCTACGCCTGAACTACAGCTGTGAGAAGGCCGT
13851  GGAAACCGCTCTCAAACTGATTTATTGGCGAAATGGCTCTAAACTAAATC
13901  GTCTCCTCTCTTTGGAAATGCTTTAGAGAAGGTCTCTGTGGTAGTTCTTA
13951  TGCATCTATCCTAAAGCACTTGGCCAGACAATTTAAAGACATCAAGCAGC
14001  ATTTATAGCAGGCACGTTTAATAACGAATACTGAATTTAAGTAACTCTGC
14051  TCACGTTGTATGACGTTTATTTTCGTATTCCTGAAAGCCATTAAAATCCT
14101  GTGCAGTTGTTTAGTAAGAACAGCTGCCACTGTTTTGTATCTAGGAGATA
14151  ACTGGTGTTTCCCTACAGTTCTCAAGCTGATAAAACTCTGTCTTTGTATC
14201  TAGGTAACCCTGTATCACTTGCTGAAGCTTTTTCAGTCTGACACCAATGC
14251  AATCCTGGGAAAGAAAACTGTAGTTTCTGAATTCTATGATGAAATGGTAT
14301  GAAAATTTTAATGTCAACCGAGCCTGACTTTATTTAAAAAAAATTATTGA
14351  TGGTGCTGTGTATTTTGGTCCTTCCTTAGATATTTCAAGATCCTACTGCC
14401  ATGATGCAGCAACTGCTAACGACGTCCCGTCAGCTGACACTTGGTGCTTA
14451  CAAGCATGAAACAGAGTGTAAGTGCAAAATGAGGATACCTTCGCCGACCG
14501  TCATTCACTACTAATGTTTTCTGTGGGATGTGATCGTACAGTGAGTTTGG
14551  CTGTGTGAAATTTGAATAGCTTGGTATTGGCAGTGATGACGTGATCGATG
14601  CCTTGCTTATCATGTTTGAAATGAAGTAGAATAAATGCAGCCTGCTTTAT
14651  TTGAGATAGTTTGGTTCATTTATGGAATGCAAGCAAAGATTATACTTCC
14701  TCACTGAATTGCACTGTCCAAAGGTGTGAAATGTGTGGGATCTGGAGGA
14751  CCGTGACCGAGGGACATTGGATCGCTATCTCCCATTTCTTTTGCTGTTAC
14801  CAGTTCAGATTTTCTTTTCACCTAGTCTTTAATTCCCAGGGTTTTGTTTT
14851  TTCCTTGGTCATAGTTTTTGTTTTTTCACTCTGGCAAATGATGTTGTAAT
14901  TACACTGCTTCAGCCACAAAACTGATGGACTGAATGAGGTCATCAAACAA
14951  ACTTTTCTTCTTCCGTATTTCCTTTTTTTTCCCCCACTTATCATTTTTAC
15001  TGCTGTTGTTGAGTCTGTAAGGCTAAAAGTAACTGTTTTGTGCTTTTTCA
15051  GGACGTGTGCTTTCCAAATTACTGCCACATATATAAAGAAAGGTTGGAAT
15101  TTTAAAGATAATTCATGTTTCTTCTTCTTTTTTGCCACCACAGTTGCAGA
15151  TCTTGAAGTAAAAACCAGGGAAAAGCTGGAAGCTGCCAAAAAGAAAACCA
15201  GTTTTGAAATTGCTGAGCTTAAAGAAAGGTTAAAAGCAAGTCGTGAAACC
15251  ATCAACTGCTTAAAGAGTGAAATCAGAAAACTCGAAGAGGATGATCAGTC
```

*Fig. 8g*

```
15301  TAAAGATATGTGATGAGTGTTGACTTGGCAGGGAGCCTATAATGAGAATG
15351  AAAGGACTTCAGTCGTGGAGTTGTATGCGTTCTCTCCAATTCTGTAACGG
15401  AGACTGTATGAATTTCATTTGCAAATCACTGCAGTGTGTGACAACTGACT
15451  TTTTATAAATGGCAGAAAACAAGAATGAATGTATCCTCATTTTATAGTTA
15501  AAATCTATGGGTATGTACTGGTTTATTTCAAGGAGAATGGATCGTAGAGA
15551  CTTGGAGGCCAGATTGCTGCTTGTATTGACTGCATTTGAGTGGTGTAGGA
15601  ACATTTGTCTATGGTCCCGTGTTAGTTTACAGAATGCCACTGTTCACTG
15651  TTTTGTTTTGTATTTTACTTTTTCTACTGCAACGTCAAGGTTTTAAAAGT
15701  TGAAAATAAAACATGCAGGTTTTTTTTAAATATTTTTTTGTCTCTATCCA
15751  GTTTGGGCTTCAAGTATTATTGTTAACAGCAAGTCCTGATTTAAGTCAGA
15801  GGCTGAAGTGTAATGGTATTCAAGATGCTTAAGTCTGTTGTCAGCAAAAC
15851  AAAAGAGAAAACTTCATAAAATCAGGAAGTTGGCATTTCTAATAACTTCT
15901  TTATCAACAGATAAGAGTTTCTAGCCCTGCATCTACTTTCACTTATGTAG
15951  TTGATGCCTTTATATTTTGTGTGTTTGGATGCAGGAAGTGATTCCTACTC
16001  TGTTATGTAGATATTCTATTTAACACTTGTACTCTGCTGTGCTTAGCCTT
16051  TCCCCATGAAAATTCAGCGGCTGTAAATCCCCCTCTTCTTTTGTAGCCTC
16101  ATACAGATGGCAGACCCTCAGGCTTATAAAGGCTTGGGCATCTTCTTTAC
16151  TGCTTTGAGATTCTGTGTTGCAGTAACCTCTGCCAGAGAGGAGAAAAGCC
16201  CCACAAACCTCATCCCCTTCTTCTATAGCAATCAGTATTACTAATGCTTT
16251  GAGAACAGAGCACTGGTTTGAAACGTTTGATAATTAGCATTTAACATGGC
16301  TTGGTAAAGATGCAGAACTGAAACAGCTGTGACAGTATGAACTCAGTATG
16351  GAGACTTCATTAAGACAAACAGCTGTTAAAATCAGGCATGTTTCATTGAG
16401  GAGGACGGGGCAACTTGCACCAGTGGTGCCCACACAAATCCTTCCTGGCG
16451  CTGCAGACCAATTTTTCTGGCATTCTGACTGCCGTTGCTGCTGGTCACAG
16501  AGAGCAACTATTTTATCAGCCACAGGCAATTTGCTTGTAGTATTTTCCA
16551  AGTGTTGTAGGTAAGTATAAATGCATCGGCTCCAGAGCACTTTGAGTATA
16601  CTTATTAAAAACATAAATGAAAGACAAATTAGCTTTGCTTGGGTGCACAG
16651  AACATTTTTAGTTCCAGCCTGCTTTTTGGTAGAAGCCCTCTTCTGAGGCT
16701  AGAACTGACTTTGACAAGTAGAGAAACTGGCAACGGAGCTATTGCTATCG
16751  AAGGATCCTTGTTAACAAAGTTAATCGTCTTTTAAGGTTTGGTTTATTCA
16801  TTAAATTTGCTTTTAAGCTGTAGCTGAAAAAGAACGTGCTGTCTTCCATG
16851  CACCAGGTGGCAGCTCTGTGCAAAGTGCTCTCTGGTCTCACCAGCCTTTT
16901  AATTGCCGGGATTCTGGCACGTCTGAGAGGGCTCAGACTGGCTTCGTTTG
16951  TTTGAACAGCGTGTACTGCTTTCTGTAGACATGGCCGGTTTCTCTCCTGC
17001  AGCTTATGAAACTGTTCACACTGAACACACTGGAACAGGTTGCCCAAGGA
17051  GGCCGTGGATGCCCCATCCCTGGAGGCATTCAAGGCCAGGCTGGATGTGG
17101  CTCTGGGCAGCCTGGTCTGGTGGTTGGCGATCCTGCACATAGCAGCGGGG
17151  TTGAAACTCGATGATCACTGTGGTCCTTTTCAACCCAGGCTATTCTATGA
17201  TTCTATGATTCAACAGCAAATCATATGTACTGAGAGAGGAAACAAACACA
17251  AGTGCTACTGTTTGCAAGTTTTGTTCATTTGGTAAAAGAGTCAGGTTTTA
17301  AAATTCAAAATCTGTCTGGTTTTGGTGTTTTTTTTTTTATTTATTATT
17351  TCTTTGGGGTTCTTTTTGATGCTTTATCTTTCTCTGCCAGGACTGTGTGA
17401  CAATGGGAACGAAAAGAACATGCCAGGCACTGTCCTGGATTGCACACGC
17451  TGGTTGCACTCAGTAGCAGGCTCAGAACTGCCAGTCTTTCCACAGTATTA
```

*Fig. 8h*

```
17501  CTTTCTAAACCTAATTTTAATAGCGTTAGTAGACTTCCATCACTGGGCAG
17551  TGCTTAGTGAATGCTCTGTGTGAACGTTTTACTTATAAGCATGTTGGAAG
17601  TTTTGATGTTCCTGGATGCAGTAGGGAAGGACAGATTAGCTATGTGAAAA
17651  GTAGATTCTGAGTATCGGGGTTACAAAAAGTATAGAAACGATGAGAAATT
17701  CTTGTTGTAACTAATTGGAATTTCTTTAAGCGTTCACTTATGCTACATTC
17751  ATAGTATTTCCATTTAAAAGTAGGAAAAGGTAAAACGTGAAATCGTGTGA
17801  TTTTCGGATGGAACACCGCCTTCCTATGCACCTGACCAACTTCCAGAGGA
17851  AAAGCCTATTGAAAGCCGAGATTAAGCCACCAAAAGAACTCATTTGCATT
17901  GGAATATGTAGTATTTGCCCTCTTCCTCCCGGGTAATTACTATACTTTAT
17951  AGGGTGCTTATATGTTAAATGAGTGGCTGGCACTTTTTATTCTCACAGCT
18001  GTGGGGAATTCTGTCCTCTAGGACAGAAACAATTTTAATCTGTTCCACTG
18051  GTGACTGCTTTGTCAGCACTTCCACCTGAAGAGATCAATACACTCTTCAA
18101  TGTCTAGTTCTGCAACACTTGGCAAACCTCACATCTTATTTCATACTCTC
18151  TTCATGCCTATGCTTATTAAAGCAATAATCTGGGTAATTTTGTTTTAAT
18201  CACTGTCCTGACCCCAGTGATGACCGTGTCCCACCTAAAGCTCAATTCAG
18251  GTCCTGAATCTCTTCAACTCTCTATAGCTAACATGAAGAATCTTCAAAAG
18301  TTAGGTCTGAGGGACTTAAGGCTAACTGTAGATGTTGTTGCCTGGTTTCT
18351  GTGCTGAAGGCCGTGTAGTAGTTAGAGCATTCAACCTCTAGaagaagctt
18401  ggccagctggtcgacctgcagatccggccctcgagggggggcccggtacc
18451  cagcttttgttccctttagtgagggttaatttcgagcttggcgtaatcat
18501  ggtcatagctgtttcctgtgtgaaattgttatccgctcacaattccacac
18551  aacatacgagccggaagcataaagtgtaaagcctggggtgcctaatgagt
18601  gagctaactcacattaattgcgttgcgctcactgcccgctttccagtcgg
18651  gaaacctgtcgtgccagctgcattaatgaatcggccaacgcgcgggaga
18701  ggcggtttgcgtattgggcgctcttccgcttcctcgctcactgactcgct
18751  gcgctcggtcgttcggctgcggcgagcggtatcagctcactcaaaggcgg
18801  taatacggttatccacagaatcaggggataacgcaggaaagaacatgtga
18851  gcaaaaggccagcaaaaggccaggaaccgtaaaaaggccgcgttgctggc
18901  gtttttccataggctccgcccccctgacgagcatcacaaaaatcgacgct
18951  caagtcagaggtggcgaaacccgacaggactataaagataccaggcgttt
19001  ccccctggaagctccctcgtgcgctctcctgttccgaccctgccgcttac
19051  cggatacctgtccgcctttctcccttcgggaagcgtggcgctttctcata
19101  gctcacgctgtaggtatctcagttcggtgtaggtcgttcgctccaagctg
19151  ggctgtgtgcacgaaccccccgttcagcccgaccgctgcgccttatccgg
19201  taactatcgtcttgagtccaacccggtaagacgacttatcgccactgg
19251  cagcagccactggtaacaggattagcagagcgaggtatgtaggcggtgct
19301  acagagttcttgaagtggtggcctaactacggctacactagaaggacagt
19351  atttggtatctgcgctctgctgaagccagttaccttcggaaaaagagttg
19401  gtagctcttgatccggcaaacaaaccaccgctggtagcggtggttttttt
19451  gtttgcaagcagcagattacgcgcagaaaaaaggatctcaagaagatcc
19501  tttgatcttttctacggggtctgacgctcagtggaacgaaaactcacgtt
19551  aagggattttggtcatgagattatcaaaaggatcttcacctagatcctt
19601  ttaaattaaaaatgaagttttaaatcaatctaaagtatatatgagtaaac
19651  ttggtctgacagttaccaatgcttaatcagtgaggcacctatctcagcga
```

*Fig. 8i*

```
19701  tctgtctatttcgttcatccatagttgcctgactccccgtcgtgtagata
19751  actacgatacgggagggcttaccatctggccccagtgctgcaatgatacc
19801  gcgagacccacgctcaccggctccagatttatcagcaataaaccagccag
19851  ccggaagggccgagcgcagaagtggtcctgcaactttatccgcctccatc
19901  cagtctattaattgttgccgggaagctagagtaagtagttcgccagttaa
19951  tagtttgcgcaacgttgttgccattgctacaggcatcgtggtgtcacgct
20001  cgtcgtttggtatggcttcattcagctccggttcccaacgatcaaggcga
20051  gttacatgatcccccatgttgtgcaaaaaagcggttagctccttcggtcc
20101  tccgatcgttgtcagaagtaagttggccgcagtgttatcactcatggtta
20151  tggcagcactgcataattctcttactgtcatgccatccgtaagatgcttt
20201  tctgtgactggtgagtactcaaccaagtcattctgagaatagtgtatgcg
20251  gcgaccgagttgctcttgcccggcgtcaatacgggataataccgcgccac
20301  atagcagaactttaaaagtgctcatcattggaaaacgttcttcggggcga
20351  aaactctcaaggatcttaccgctgttgagatccagttcgatgtaacccac
20401  tcgtgcacccaactgatcttcagcatcttttactttcaccagcgtttctg
20451  ggtgagcaaaaacaggaaggcaaaatgccgcaaaaaagggaataagggcg
20501  acacggaaatgttgaatactcatactcttccttttcaatattattgaag
20551  catttatcagggttattgtctcatgagcggatacatatttgaatgtattt
20601  agaaaaataaacaatagggggttccgcgcacatttccccgaaaagtgcca
20651  cctaaattgtaagcgttaatatttgttaaaattcgcgttaaattttttgt
20701  taaatcagctcattttttaaccaataggccgaaatcggcaaaatccctta
20751  taaatcaaaagaatagaccgagatagggttgagtgttgttccagtttgga
20801  acaagagtccactattaaagaacgtggactccaacgtcaaagggcgaaaa
20851  accgtctatcagggcgatggcccactacgtgaaccatcaccctaatcaag
20901  ttttttggggtcgaggtgccgtaaagcactaaatcggaaccctaaaggga
20951  gccccgatttagagcttgacggggaaagccggcgaacgtggcgagaaag
21001  gaagggaagaaagcgaaaggagcgggcgctagggcgctggcaagtgtagc
21051  ggtcacgctgcgcgtaaccaccacacccgccgcgcttaatgcgccgctac
21101  agggcgcgtcccattcgccattcaggctgcgcaactgttgggaagggcga
21151  tcggtgcgggcctcttcgctattacgccagctggcgaaaggggggatgtgc
21201  tgcaaggcgattaagttgggtaacgccagggttttcccagtcacgacgtt
21251  gtaaaacgacggccagtgaattgtaatacgactcactatagggcgaattg
21301  gagctccaccgcggtggcggccgctctag
```

*Fig. 8j*

```
                            SEQUENCE LISTING

<160> NUMBER OF SEQ ID NOS: 70

<210> SEQ ID NO 1
   <211> LENGTH: 20
   <212> TYPE: DNA
   <213> ORGANISM: Artificial Sequence
   <220> FEATURE:
   <223> OTHER INFORMATION: Primer 5pLMAR2

<400> SEQUENCE: 1
tgccgccttc tttgatattc                                                   20

<210> SEQ ID NO 2
   <211> LENGTH: 20
   <212> TYPE: DNA
   <213> ORGANISM: Artificial Sequence
   <220> FEATURE:
   <223> OTHER INFORMATION: Primer LE-6.1kbrev1

<400> SEQUENCE: 2
ttggtggtaa ggccttttg                                                    20

<210> SEQ ID NO 3
   <211> LENGTH: 20
   <212> TYPE: DNA
   <213> ORGANISM: Artificial Sequence
   <220> FEATURE:
   <223> OTHER INFORMATION: Primer lys-6.1

<400> SEQUENCE: 3
ctggcaagct gtcaaaaaca                                                   20

<210> SEQ ID NO 4
   <211> LENGTH: 20
   <212> TYPE: DNA
   <213> ORGANISM: Artificial Sequence
   <220> FEATURE:
   <223> OTHER INFORMATION: Primer LysE1rev

<400> SEQUENCE: 4
cagctcacat cgtccaaaga                                                   20

<210> SEQ ID NO 5
   <211> LENGTH: 34
   <212> TYPE: DNA
   <213> ORGANISM: Artificial Sequence
   <220> FEATURE:
```

<223> OTHER INFORMATION: Primer LYSBSU

<400> SEQUENCE: 5 cccccccccta aggcagccag gggcaggaag caaa          34

<210> SEQ ID NO 6
<211> LENGTH: 12
<212> TYPE: DNA
<213> ORGANISM: Artificial Sequence
<220> FEATURE:
<223> OTHER INFORMATION: Primer SaltoNotI

<400> SEQUENCE: 6
tcgagcggcc gc          12

<210> SEQ ID NO 7
<211> LENGTH: 20
<212> TYPE: DNA
<213> ORGANISM: Artificial Sequence
<220> FEATURE:
<223> OTHER INFORMATION: Primer T7

<400> SEQUENCE: 7
taatacgact cactataggg          20

<210> SEQ ID NO 8
<211> LENGTH: 21
<212> TYPE: DNA
<213> ORGANISM: Artificial Sequence
<220> FEATURE:
<223> OTHER INFORMATION: Primerlys61enfor1

<400> SEQUENCE: 8
cgtggtgatc aaatctttgt g          21

<210> SEQ ID NO 9
<211> LENGTH: 20
<212> TYPE: DNA
<213> ORGANISM: Artificial Sequence
<220> FEATURE:
<223> OTHER INFORMATION: Primer lys61enrev1

<400> SEQUENCE: 9
aggagggcac agtagggatc          20

<210> SEQ ID NO 10
<211> LENGTH: 19
<212> TYPE: DNA
<213> ORGANISM: Artificial Sequence
<220> FEATURE:
<223> OTHER INFORMATION: Primer 5MARfor1

<400> SEQUENCE: 10
gtggcctgtg tctgtgctt          19

<210> SEQ ID NO 11
<211> LENGTH: 20
<212> TYPE: DNA
<213> ORGANISM: Artificial Sequence
<220> FEATURE:
<223> OTHER INFORMATION: Primer IFN-3rev

<400> SEQUENCE: 11
aactcctctt gaggaaagcc          20

```
<210> SEQ ID NO 12
<211> LENGTH: 20
<212> TYPE: DNA
<213> ORGANISM: Artificial Sequence
<220> FEATURE:
<223> OTHER INFORMATION: Primer lys001rev

<400> SEQUENCE: 12
tcctgtttgg gatgaatggt                                              20

<210> SEQ ID NO 13
<211> LENGTH: 20
<212> TYPE: DNA
<213> ORGANISM: Artificial Sequence
<220> FEATURE:
<223> OTHER INFORMATION: Primer lys002for

<400> SEQUENCE: 13
ctctcagaat gcccaactcc                                              20

<210> SEQ ID NO 14
<211> LENGTH: 20
<212> TYPE: DNA
<213> ORGANISM: Artificial Sequence
<220> FEATURE:
<223> OTHER INFORMATION: Primer lys003for

<400> SEQUENCE: 14
tgtattggtc tccctcctgc                                              20

<210> SEQ ID NO 15
<211> LENGTH: 20
<212> TYPE: DNA
<213> ORGANISM: Artificial Sequence
<220> FEATURE:
<223> OTHER INFORMATION: Primer lys005for

<400> SEQUENCE: 15
tgttgaaatt gcagtgtggc                                              20

<210> SEQ ID NO 16
<211> LENGTH: 20
<212> TYPE: DNA
<213> ORGANISM: Artificial Sequence
<220> FEATURE:
<223> OTHER INFORMATION: Primer lys006rev

<400> SEQUENCE: 16
tgacaatgca aatttggctc                                              20

<210> SEQ ID NO 17
<211> LENGTH: 20
<212> TYPE: DNA
<213> ORGANISM: Artificial Sequence
<220> FEATURE:
<223> OTHER INFORMATION: Primer lys007for

<400> SEQUENCE: 17
gatatccttg cagtgcccat                                              20

<210> SEQ ID NO 18
<211> LENGTH: 20
<212> TYPE: DNA
<213> ORGANISM: Artificial Sequence
<220> FEATURE:
<223> OTHER INFORMATION: Primer lys008rev
```

```
<400> SEQUENCE: 18
ggacaagcaa gtgcatcaga                                            20

<210> SEQ ID NO 19
<211> LENGTH: 20
<212> TYPE: DNA
<213> ORGANISM: Artificial Sequence
<220> FEATURE:
<223> OTHER INFORMATION: Primer lys009for

<400> SEQUENCE: 19
ctgatgtgct tcagctctgc                                            20

<210> SEQ ID NO 20
<211> LENGTH: 20
<212> TYPE: DNA
<213> ORGANISM: Artificial Sequence
<220> FEATURE:
<223> OTHER INFORMATION: Primer lys010rev

<400> SEQUENCE: 20
tccatggtgg tcaaacagaa                                            20

<210> SEQ ID NO 21
<211> LENGTH: 20
<212> TYPE: DNA
<213> ORGANISM: Artificial Sequence
<220> FEATURE:
<223> OTHER INFORMATION: Primer lys011for

<400> SEQUENCE: 21
gtactagacc aggcagccca                                            20

<210> SEQ ID NO 22
<211> LENGTH: 20
<212> TYPE: DNA
<213> ORGANISM: Artificial Sequence
<220> FEATURE:
<223> OTHER INFORMATION: Primer lys012rev

<400> SEQUENCE: 22
gtgggaagta ccacattggc                                            20

<210> SEQ ID NO 23
<211> LENGTH: 20
<212> TYPE: DNA
<213> ORGANISM: Artificial Sequence
<220> FEATURE:
<223> OTHER INFORMATION: Primer lys013for

<400> SEQUENCE: 23
cgctcaggag aaagtgaacc                                            20

<210> SEQ ID NO 24
<211> LENGTH: 20
<212> TYPE: DNA
<213> ORGANISM: Artificial Sequence
<220> FEATURE:
<223> OTHER INFORMATION: Primer lys014rev

<400> SEQUENCE: 24
cggttttgcc tttgtgtttt                                            20

<210> SEQ ID NO 25
<211> LENGTH: 20
```

<212> TYPE: DNA
<213> ORGANISM: Artificial Sequence
<220> FEATURE:
<223> OTHER INFORMATION: Primer lys015rev

<400> SEQUENCE: 25
aaatgctcga tttcattggg                                          20

<210> SEQ ID NO 26
<211> LENGTH: 20
<212> TYPE: DNA
<213> ORGANISM: Artificial Sequence
<220> FEATURE:
<223> OTHER INFORMATION: Primer lys016rev

<400> SEQUENCE: 26
gccaatcaga ctgcatttca                                          20

<210> SEQ ID NO 27
<211> LENGTH: 20
<212> TYPE: DNA
<213> ORGANISM: Artificial Sequence
<220> FEATURE:
<223> OTHER INFORMATION: Prmer lys017rev

<400> SEQUENCE: 27
aaccgctgaa tggaacagtc                                          20

<210> SEQ ID NO 28
<211> LENGTH: 20
<212> TYPE: DNA
<213> ORGANISM: Artificial Sequence
<220> FEATURE:
<223> OTHER INFORMATION: Primer lys018for

<400> SEQUENCE: 28
acacgcacat attttgctgg                                          20

<210> SEQ ID NO 29
<211> LENGTH: 20
<212> TYPE: DNA
<213> ORGANISM: Artificial Sequence
<220> FEATURE:
<223> OTHER INFORMATION: Primer lys019rev

<400> SEQUENCE: 29
caggagctgg attccttcag                                          20

<210> SEQ ID NO 30
<211> LENGTH: 20
<212> TYPE: DNA
<213> ORGANISM: Artificial Sequence
<220> FEATURE:
<223> OTHER INFORMATION: Primer lys020for

<400> SEQUENCE: 30
aaaggatgca gtcccaaatg                                          20

<210> SEQ ID NO 31
<211> LENGTH: 20
<212> TYPE: DNA
<213> ORGANISM: Artificial Sequence
<220> FEATURE:
<223> OTHER INFORMATION: Primer lys021rev

<400> SEQUENCE: 31

-continued gcccctagac tccatcttcc      20

<210> SEQ ID NO 32
<211> LENGTH: 20
<212> TYPE: DNA
<213> ORGANISM: Artificial Sequence
<220> FEATURE:
<223> OTHER INFORMATION: Primer lys022rev

<400> SEQUENCE: 32
atttgctgtg gtggatgtga      20

<210> SEQ ID NO 33
<211> LENGTH: 20
<212> TYPE: DNA
<213> ORGANISM: Artificial Sequence
<220> FEATURE:
<223> OTHER INFORMATION: Primer lys024for

<400> SEQUENCE: 33
ccttgcagtc cttggtttgt      20

<210> SEQ ID NO 34
<211> LENGTH: 20
<212> TYPE: DNA
<213> ORGANISM: Artificial Sequence
<220> FEATURE:
<223> OTHER INFORMATION: Primer lys025rev

<400> SEQUENCE: 34
atgatccttc tgatgggctg      20

<210> SEQ ID NO 35
<211> LENGTH: 20
<212> TYPE: DNA
<213> ORGANISM: Artificial Sequence
<220> FEATURE:
<223> OTHER INFORMATION: Primer lys026rev

<400> SEQUENCE: 35
acagtgatag cacaagggg      20

<210> SEQ ID NO 36
<211> LENGTH: 20
<212> TYPE: DNA
<213> ORGANISM: Artificial Sequence
<220> FEATURE:
<223> OTHER INFORMATION: Primer lys027rev

<400> SEQUENCE: 36
gtaaacagct gcaacaggca      20

<210> SEQ ID NO 37
<211> LENGTH: 21
<212> TYPE: DNA
<213> ORGANISM: Artificial Sequence
<220> FEATURE:
<223> OTHER INFORMATION: Primer lys028rev

<400> SEQUENCE: 37
caacacaaaa gttggacagc a      21

<210> SEQ ID NO 38
<211> LENGTH: 20
<212> TYPE: DNA
<213> ORGANISM: Artificial Sequence

```
<220> FEATURE:
<223> OTHER INFORMATION: Primer lys030rev

<400> SEQUENCE: 38
tttgcagatg agacgtttgc                                               20

<210> SEQ ID NO 39
<211> LENGTH: 20
<212> TYPE: DNA
<213> ORGANISM: Artificial Sequence
<220> FEATURE:
<223> OTHER INFORMATION: Primer lys030rev

<400> SEQUENCE: 39
ccacaagttc ttgtttgggc                                               20

<210> SEQ ID NO 40
<211> LENGTH: 20
<212> TYPE: DNA
<213> ORGANISM: Artificial Sequence
<220> FEATURE:
<223> OTHER INFORMATION: Primer lys031rev

<400> SEQUENCE: 40
atcaatccat gccagtagcc                                               20

<210> SEQ ID NO 41
<211> LENGTH: 20
<212> TYPE: DNA
<213> ORGANISM: Artificial Sequence
<220> FEATURE:
<223> OTHER INFORMATION: Primer lys032rev

<400> SEQUENCE: 41
gtttaaggcc ccttccaatc                                               20

<210> SEQ ID NO 42
<211> LENGTH: 20
<212> TYPE: DNA
<213> ORGANISM: Artificial Sequence
<220> FEATURE:
<223> OTHER INFORMATION: Primer lys033for

<400> SEQUENCE: 42 gagaggggt tgggtgtatt                                                20

<210> SEQ ID NO 43
<211> LENGTH: 20
<212> TYPE: DNA
<213> ORGANISM: Artificial Sequence
<220> FEATURE:
<223> OTHER INFORMATION: Primer lys034for

<400> SEQUENCE: 43
acagtggaag cattcaaggg                                               20

<210> SEQ ID NO 44
<211> LENGTH: 20
<212> TYPE: DNA
<213> ORGANISM: Artificial Sequence
<220> FEATURE:
<223> OTHER INFORMATION: Primer lys037for

<400> SEQUENCE: 44
ccaatgcctt tggttctgat                                               20
```

<210> SEQ ID NO 45
<211> LENGTH: 20
<212> TYPE: DNA
<213> ORGANISM: Artificial Sequence
<220> FEATURE:
<223> OTHER INFORMATION: Primer lys038for

<400> SEQUENCE: 45
aaaacacaaa ggcaaaaccg                                                          20

<210> SEQ ID NO 46
<211> LENGTH: 20
<212> TYPE: DNA
<213> ORGANISM: Artificial Sequence
<220> FEATURE:
<223> OTHER INFORMATION: Primer lys039rev

<400> SEQUENCE: 46
ctaagcctcg ccagtttcaa                                                          20

<210> SEQ ID NO 47
<211> LENGTH: 20
<212> TYPE: DNA
<213> ORGANISM: Artificial Sequence
<220> FEATURE:
<223> OTHER INFORMATION: Primer lys040rev

<400> SEQUENCE: 47
tgccatgaaa accctactga                                                          20

<210> SEQ ID NO 48
<211> LENGTH: 20
<212> TYPE: DNA
<213> ORGANISM: Artificial Sequence
<220> FEATURE:
<223> OTHER INFORMATION: Primer lys041for

<400> SEQUENCE: 48
ggaatgtacc ctcagctcca                                                          20

<210> SEQ ID NO 49
<211> LENGTH: 20
<212> TYPE: DNA
<213> ORGANISM: Artificial Sequence
<220> FEATURE:
<223> OTHER INFORMATION: Primer lys042rev

<400> SEQUENCE: 49
cctctttagg aggccagctt                                                          20

<210> SEQ ID NO 50
<211> LENGTH: 20
<212> TYPE: DNA
<213> ORGANISM: Artificial Sequence
<220> FEATURE:
<223> OTHER INFORMATION: Primer lys043rev

<400> SEQUENCE: 50
aagatgatca gagggctgga                                                          20

<210> SEQ ID NO 51
<211> LENGTH: 20
<212> TYPE: DNA
<213> ORGANISM: Artificial Sequence
<220> FEATURE:
<223> OTHER INFORMATION: Primer lys044rev

<400> SEQUENCE: 51
gcagcgctgg taatcttcat                                          20

<210> SEQ ID NO 52
<211> LENGTH: 20
<212> TYPE: DNA
<213> ORGANISM: Artificial Sequence
<220> FEATURE:
<223> OTHER INFORMATION: Primer lys045for

<400> SEQUENCE: 52
cttcagatcc caggaagtgc                                          20

<210> SEQ ID NO 53
<211> LENGTH: 20
<212> TYPE: DNA
<213> ORGANISM: Artificial Sequence
<220> FEATURE:
<223> OTHER INFORMATION: Primer lys46for

<400> SEQUENCE: 53
ttcctgcctt acattctggg                                          20

<210> SEQ ID NO 54
<211> LENGTH: 20
<212> TYPE: DNA
<213> ORGANISM: Artificial Sequence
<220> FEATURE:
<223> OTHER INFORMATION: Primer lys047for

<400> SEQUENCE: 54
cccactgcag gcttagaaag                                          20

<210> SEQ ID NO 55
<211> LENGTH: 20
<212> TYPE: DNA
<213> ORGANISM: Artificial Sequence
<220> FEATURE:
<223> OTHER INFORMATION: Primer lys048for

<400> SEQUENCE: 55
agttctccat agcggctgaa                                          20

<210> SEQ ID NO 56
<211> LENGTH: 20
<212> TYPE: DNA
<213> ORGANISM: Artificial Sequence
<220> FEATURE:
<223> OTHER INFORMATION: Primer lys051for

<400> SEQUENCE: 56
tgcatccttc agcacttgag                                          20

<210> SEQ ID NO 57
<211> LENGTH: 20
<212> TYPE: DNA
<213> ORGANISM: Artificial Sequence
<220> FEATURE:
<223> OTHER INFORMATION: Primer lys052rev

<400> SEQUENCE: 57
gcaggaggga gaccaataca                                          20

<210> SEQ ID NO 58

```
<211> LENGTH: 20
<212> TYPE: DNA
<213> ORGANISM: Artificial Sequence
<220> FEATURE:
<223> OTHER INFORMATION: Primer lys053for

<400> SEQUENCE: 58
tgcacaagga tgtctgggta                                                20

<210> SEQ ID NO 59
<211> LENGTH: 20
<212> TYPE: DNA
<213> ORGANISM: Artificial Sequence
<220> FEATURE:
<223> OTHER INFORMATION: Primer lys054for

<400> SEQUENCE: 59
tcctagcaac tgcggatttt                                                20

<210> SEQ ID NO 60
<211> LENGTH: 20
<212> TYPE: DNA
<213> ORGANISM: Artificial Sequence
<220> FEATURE:
<223> OTHER INFORMATION: Primer lys056for

<400> SEQUENCE: 60
tcttccatgt tggtgacagc                                                20

<210> SEQ ID NO 61
<211> LENGTH: 20
<212> TYPE: DNA
<213> ORGANISM: Artificial Sequence
<220> FEATURE:
<223> OTHER INFORMATION: Primer lys058for

<400> SEQUENCE: 61
cccccttgtg ctatcactgt                                                20

<210> SEQ ID NO 62
<211> LENGTH: 20
<212> TYPE: DNA
<213> ORGANISM: Artificial Sequence
<220> FEATURE:
<223> OTHER INFORMATION: Primer lys059for

<400> SEQUENCE: 62
ctgacagaca tcccagctca                                                20

<210> SEQ ID NO 63
<211> LENGTH: 20
<212> TYPE: DNA
<213> ORGANISM: Artificial Sequence
<220> FEATURE:
<223> OTHER INFORMATION: Primer lys060for

<400> SEQUENCE: 63
aagttgtgct tctgcgtgtg                                                20

<210> SEQ ID NO 64
<211> LENGTH: 20
<212> TYPE: DNA
<213> ORGANISM: Artificial Sequence
<220> FEATURE:
<223> OTHER INFORMATION: Primer lys061for

<400> SEQUENCE: 64
```
ttgttcctgc tgttcctcct                                                    20

<210> SEQ ID NO 65
<211> LENGTH: 12728
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11946)..(12443)
<223> OTHER INFORMATION: Human Interferon alpha 2d encoding region codon
      optimized for expression in chicken cells (IFNMAGMAX
<220> FEATURE:
<221> NAME/KEY: polyA_signal
<222> LOCATION: (12444)..(12728)

<400> SEQUENCE: 65
tgccgccttc tttgatattc actctgttgt atttcatctc ttcttgccga tgaaaggata    60
taacagtctg tataacagtc tgtgaggaaa tacttggtat ttcttctgat cagtgttttt   120

-continued

```
ataagtaatg ttgaatattg gataaggctg tgtgtccttt gtcttgggag acaaagccca      180
cagcaggtgg tggttggggt ggtggcagct cagtgacagg agaggttttt ttgcctgttt      240
tttttttttt tttttttttt aagtaaggtg ttcttttttc ttagtaaatt ttctactgga      300
ctgtatgttt tgacaggtca gaaacatttc ttcaaaagaa gaaccttttg gaaactgtac      360
agcccttttc tttcattccc ttttttgcttt ctgtgccaat gcctttggtt ctgattgcat      420
tatggaaaac gttgatcgga acttgaggtt tttatttata gtgtggcttg aaagcttgga      480
tagctgttgt tacacgagat accttattaa gtttaggcca gcttgatgct ttattttttc      540
cctttgaagt agtgagcgtt ctctggtttt tttcctttga aactggtgag gcttagattt      600
ttctaatggg attttttacc tgatgatcta gttgcatacc caaatgcttg taaatgtttt      660
cctagttaac atgttgataa cttcggattt acatgttgta tatacttgtc atctgtgttt      720
ctagtaaaaa tatatggcat ttatagaaat acgtaattcc tgatttcctt ttttttttatc      780 tctatgctct gtgtgtacag gtcaaacaga cttcactcct attttttattt atagaatttt      840 atatgcagtc tgtcgttggt tcttgtgttg taaggataca gccttaaatt tcctagagcg      900
atgctcagta aggcgggttg tcacatgggt tcaaatgtaa aacgggcacg tttggctgct      960
gccttcccga gatccaggac actaaactgc ttctgcactg aggtataaat cgcttcagat     1020
cccagggaag tgcagatcca cgtgcatatt cttaaagaag aatgaatact ttctaaaata     1080
ttttggcata ggaagcaagc tgcatggatt tgtttgggac ttaaattatt ttggtaacgg     1140
agtgcatagg ttttaaacac agttgcagca tgctaacgag tcacagcgtt tatgcagaag     1200
tgatgcctgg atgcctgttg cagctgttta cggcactgcc ttgcagtgag cattgcagat     1260
aggggtgggg tgctttgtgt cgtgttccca cacgctgcca cacagccacc tcccggaaca     1320
catctcacct gctgggtact tttcaaacca tcttagcagt agtagatgag ttactatgaa     1380
acagagaagt tcctcagttg gatattctca tgggatgtct ttttttcccat gttgggcaaa     1440 gtatgataaa gcatctctat ttgtaaatta tgcacttgtt agttcctgaa tcctttctat     1500
agcaccactt attgcagcag gtgtaggctc tggtgtggcc tgtgtctgtg cttcaatctt     1560
ttaaagcttc tttggaaata cactgacttg attgaagtct cttgaagata gtaaacagta     1620
cttacctttg atcccaatga aatcgagcat ttcagttgta aaagaattcc gcctattcat     1680
accatgtaat gtaattttac accccagtg ctgacacttt ggaatatatt caagtaatag     1740
actttggcct caccctcttg tgtactgtat tttgtaatag aaaatatttt aaactgtgca     1800
tatgattatt acattatgaa agagacattc tgctgatctt caaatgtaag aaaatgagga     1860
gtgcgtgtgc ttttataaat acaagtgatt gcaaattagt gcaggtgtcc ttaaaaaaaa     1920
aaaaaaaaag taatataaaa aggaccaggt gttttacaag tgaaatacat tcctatttgg     1980
taaacagtta cattttttatg aagattacca gcgctgctga ctttctaaac ataaggctgt     2040
attgtcttcc tgtaccattg catttcctca ttcccaattt gcacaaggat gtctgggtaa     2100
actattcaag aaaatggcttt gaaatacagc atgggagctt gtctgagttg gaatgcagag     2160
ttgcactgca aaatgtcagg aaatggatgt ctctcagaat gcccaactcc aaaggatttt     2220
atatgtgtat atagtaagca gtttcctgat tccagcaggc caaagagtct gctgaatgtt     2280
gtgttgccgg agacctgtat ttctcaacaa ggtaagatgg tatcctagca actgcggatt     2340
ttaatacatt ttcagcagaa gtacttagtt aatctctacc tttagggatc gtttcatcat     2400
ttttagatgt tatacttgaa atactgcata acttttagct ttcatgggtt cctttttttc     2460
```

```
agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata cttttttaaa gtcaacttt t    2820
tatcagattt ttttttcatt tggaaatata ttgttttcta gactgcatag cttctgaatc    2880
tgaaatgcag tctgattggc atgaagaagc acagcactct tcatcttact aaacttcat     2940
tttggaatga aggaagttaa gcaagggcac aggtccatga aatagagaca gtgcgctcag    3000
gagaaagtga acctggattt cttt ggctag tgttctaaat ctgtagtgag aaagtaaca    3060
cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tattttt aag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaagtaag cagtcttcat atgttttccc tccacgtaaa     3540
gcagtctggg aaagtagcac cccttgagca gagacaagga aataattcag gagcatgtgc    3600
taggagaact tccttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtcttt gc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggccccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500
tctttcccctt tttcctgcta agtaaggatt ttctcctggc tttgacacct cacgaaatag    4560
tcttcctgcc ttacattctg gcattatttt caaatatctt tggagtgcgc tgctctcaag    4620
tttgtgtctt cctactctta gagtgaatgc tcttagagtg aaagaaagg aagagaagat    4680
gttggccgca gttctctgat gaacacacct ctgaataatg ccaaaggtg ggtgggtttc     4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
```

```
ttccttcttg gcagtcagtt tatttctgac agacaaacag ccacccccac tgcaggctta    4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggca attttttta aatacataaa      5280 ctacttcaaa tgaggtcgga gaaggtcagt gttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt tacccactga ctgttccatt    5580
cagcggtttg gaaagagaaa aagaatttgg aaataaaaca tgtctacgtt atcacctcct    5640
ccagcatttt ggttttttaat tatgtcaata actggcttag atttggaaat gagaggggggt   5700 tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttattttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa ccccttaagg cattcagaac aactagaatc atagaatggt ttggattgga    6600
agggccctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccctts ctgatttgtg tcaagctttt    7200
```

```
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata atcctgtat ttgggatcag     7500
ttacctttg gggtaagctt ttgtatctgc agagaccctg ggggttctga tgtgcttcag     7560
ctctgctctg ttctgactgc accattttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcatttatt acttctatta tgtacttact ttgacataac acagacacgc acatattttg     7920
ctgggatttc cacagtgtct ctgtgtcctt cacatggttt tactgtcata cttccgttat    7980
aaccttggca atctgcccag ctgcccatca caagaaaaga gattcctttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgcccaa gccagagagg ctgtctgcca     8220
aggccacctt gcagtccttg gtttgtaaga taagtcatag gtaacttttc tggtgaattg    8280
cgtggagaat catgatggca gttcttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaaccttt ggcctgactg atgcctcccg    8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
tttttcttcc tgctgtcagg aacatttga ataccagaga aaagaaaag tgctcttctt      8820
ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcatttttt ataggacttc caggaaggat cttcttctta agcttcttaa ttatggtaca   9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
tctggctatg aaagtctgct tacaaggaag aggataaaaa tcatagggat aataaatcta    9420
agtttgaaga caatgaggtt ttagctgcat ttgacatgaa gaaattgaga cctctactgg    9480
atagctatgg tatttacgtg tcttttttgct tagttactta ttgaccccag ctgaggtcaa    9540
gtatgaactc aggtctctcg ggctactggc atggattgat tacatacaac tgtaatttta    9600
```

-continued

```
gcagtgattt agggtttatg agtacttttg cagtaaatca tagggttagt aatgttaatc    9660
tcagggaaaa aaaaaaaaag ccaaccctga cagacatccc agctcaggtg gaaatcaagg    9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaattttct ctccgctgca cagttccagt catcccagtt tgtacagttc    9900
tggcactttt tgggtcaggc cgtgatccaa ggagcagaag ttccagctat ggtcagggag    9960
tgcctgaccg tcccaactca ctgcactcaa acaaaggcga aaccacaaga gtggcttttg    10020
ttgaaattgc agtgtggccc agaggggctg caccagtact ggattgacca cgaggcaaca    10080
ttaatcctca gcaagtgcaa tttgcagcca ttaaattgaa ctaactgata ctacaatgca    10140
atcagtatca acaagtggtt tggcttggaa gatggagtct aggggctcta caggagtagc    10200
tactctctaa tggagttgca ttttgaagca ggacactgtg aaaagctggc ctcctaaaga    10260
ggctgctaaa cattagggtc aattttccag tgcactttct gaagtgtctg cagttcccca    10320
tgcaaagctg cccaaacata gcacttccaa ttgaatacaa ttatatgcag gcgtactgct    10380
tcttgccagc actgtccttc tcaaatgaac tcaacaaaca atttcaaagt ctagtagaaa    10440
gtaacaagct ttgaatgtca ttaaaaagta tatctgcttt cagtagttca gcttatttat    10500
gcccactaga aacatcttgt acaagctgaa cactggggct ccagattagt ggtaaaacct    10560
actttataca atcatagaat catagaatgg cctgggttgg aagggacccc aaggatcatg    10620
aagatccaac accccgcca caggcagggc caccaacctc cagatctggt actagaccag    10680
gcagcccagg gctccatcca acctggccat gaacacctcc agggatggag catccacaac    10740
ctctctgggc agcctgtgcc agcacctcac caccctctct gtgaagaact tttccctgac    10800
atccaatcta agccttccct ccttgaggtt agatccactc ccccttgtgc tatcactgtc    10860
tactcttgta aaaagttgat tctcctcctt tttggaaggt tgcaatgagg tctccttgca    10920
gccttcttct cttctgcagg atgaacaagc ccagctccct cagcctgtct ttataggaga    10980
ggtgctccag ccctctgatc atctttgtgg ccctcctctg acccgctcc aagagctcca    11040 catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgatacctc accccacctg ccactgaatg gctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttga caactgtaga acagaggaat caaaggggg     11820 tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
```

```
tagggtgcga tctgcctcag acccacagcc tgggcagcag gaggaccctg atgctgctgg    12000
ctcagatgag gagaatcagc ctgtttagct gcctgaagga taggcacgat tttggctttc    12060
ctcaagagga gtttggcaac cagtttcaga aggctgagac catccctgtg ctgcacgaga    12120
tgatccagca gatctttaac ctgtttagca ccaaggatag cagcgctgct gggatgaga    12180 ccctgctgga taagttttac accgagctgt accagcagct gaacgatctg gaggcttgcg    12240
tgatccaggg cgtgggcgtg accgagaccc tctgatgaa ggaggatagc atcctggctg    12300
tgaggaagta ctttcagagg atcaccctgt acctgaagga gaagaagtac agcccctgcg    12360
cttgggaagt cgtgagggct gagatcatga ggagctttag cctgagcacc aacctgcaag    12420
agagcttgag gtctaaggag taaaaagtct agagtcgggg cggccggccg cttcgagcag    12480
acatgataag atacattgat gagtttggac aaaccacaac tagaatgcag tgaaaaaaat    12540
gctttatttg tgaaatttgt gatgctattg ctttatttgt aaccattata agctgcaata    12600
aacaagttaa caacaacaat tgcattcatt ttatgtttca ggttcagggg gaggtgtggg    12660
aggtttttta aagcaagtaa aacctctaca aatgtggtaa aatcgataag gatccgtcga    12720
gcggccgc                                                             12728

<210> SEQ ID NO 66
<211> LENGTH: 498
<212> TYPE: DNA
<213> ORGANISM: Artificial Sequence
<220> FEATURE:
<223> OTHER INFORMATION: IFNMAGMAX
<220> FEATURE:
<221> NAME/KEY: misc_feature
<222> LOCATION: (1)..(498)

<400> SEQUENCE: 66
tgcgatctgc ctcagaccca cagcctgggc agcaggagga ccctgatgct gctggctcag      60
atgaggagaa tcagcctgtt tagctgcctg aaggataggc acgatttgg ctttcctcaa     120 gaggagtttg gcaaccagtt tcagaaggct gagaccatcc ctgtgctgca cgagatgatc     180
cagcagatct ttaacctgtt tagcaccaag gatagcagcg ctgcttggga tgagaccctg     240
ctggataagt tttacaccga gctgtaccag cagctgaacg atctggaggc ttgcgtgatc     300
cagggcgtgg gcgtgaccga gacccctctg atgaaggagg atagcatcct ggctgtgagg     360
aagtactttc agaggatcac cctgtacctg aaggagaaga gtacagccc ctgcgcttgg     420 gaagtcgtga gggctgagat catgaggagc tttagcctga gcaccaacct gcaagagagc     480
ttgaggtcta aggagtaa                                                   498

<210> SEQ ID NO 67
<211> LENGTH: 11945
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix attachment region (MAR)
<220> FEATURE:
<221> NAME/KEY: misc_feature
<222> LOCATION: (261)..(1564)
<223> OTHER INFORMATION: 5prime matrix attachment region (MAR)
<220> FEATURE:
<221> NAME/KEY: misc_feature
<222> LOCATION: (1565)..(1912)
<223> OTHER INFORMATION: 5prime matrix attachment region (MAR)
<220> FEATURE:
<221> NAME/KEY: misc_feature
<222> LOCATION: (1930)..(2012)
```

```
<223> OTHER INFORMATION: 5prime matrix attachment region (MAR)
<220> FEATURE:
<221> NAME/KEY: misc_feature
<222> LOCATION: (2013)..(2671)
<223> OTHER INFORMATION: Intrinsically Curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat
<220> FEATURE:
<221> NAME/KEY: misc_feature
<222> LOCATION: (10926)..(11193)
<223> OTHER INFORMATION: Chicken CR1 Repeat
<220> FEATURE:
<221> NAME/KEY: misc_feature
<222> LOCATION: (11424)..(11938)
<223> OTHER INFORMATION: Proximal promoter and lysozyme signal peptide

<400> SEQUENCE: 67
```

| | | | | | |
|---|---|---|---|---|---|
| tgccgccttc | tttgatattc | actctgttgt | atttcatctc | ttcttgccga | tgaaaggata | 60 |
| taacagtctg | tataacagtc | tgtgaggaaa | tacttggtat | ttcttctgat | cagtgttttt | 120 |
| ataagtaatg | ttgaatattg | gataaggctg | tgtgtccttt | gtcttgggag | acaaagccca | 180 |
| cagcaggtgg | tggttggggt | ggtggcagct | cagtgacagg | agaggttttt | ttgcctgttt | 240 |
| tttttttttt | tttttttttt | aagtaaggtg | ttcttttttc | ttagtaaatt | ttctactgga | 300 |
| ctgtatgttt | tgacaggtca | gaaacatttc | ttcaaaagaa | gaaccttttg | gaaactgtac | 360 |
| agcccttttc | tttcattccc | ttttgctttt | ctgtgccaat | gcctttggtt | ctgattgcat | 420 |
| tatggaaaac | gttgatcgga | acttgaggtt | tttatttata | gtgtggcttg | aaagcttgga | 480 |
| tagctgttgt | tacacgagat | accttattaa | gtttaggcca | gcttgatgct | ttattttttc | 540 |
| cctttgaagt | agtgagcgtt | ctctggtttt | tttcctttga | aactggtgag | gcttagattt | 600 |
| ttctaatggg | atttttacc | tgatgatcta | gttgcatacc | caaatgcttg | taaatgtttt | 660 |
| cctagttaac | atgttgataa | cttcggattt | acatgttgta | tatacttgtc | atctgtgttt | 720 |
| ctagtaaaaa | tatatggcat | ttatagaaat | acgtaattcc | tgatttcctt | tttttttatc | 780 |
| tctatgctct | gtgtgtacag | gtcaaacaga | cttcactcct | atttttattt | atagaatttt | 840 |
| atatgcagtc | tgtcgttggt | tcttgtgttg | taaggataca | gccttaaatt | tcctagagcg | 900 |
| atgctcagta | aggcgggttg | tcacatgggt | tcaaatgtaa | aacgggcacg | tttggctgct | 960 |
| gccttcccga | gatccaggac | actaaactgc | ttctgcactg | aggtataaat | cgcttcagat | 1020 |
| cccagggaag | tgcagatcca | cgtgcatatt | cttaagaag | aatgaatact | ttctaaaata | 1080 |
| ttttggcata | ggaagcaagc | tgcatggatt | tgttgggac | ttaaattatt | ttggtaacgg | 1140 |
| agtgcatagg | ttttaaacac | agttgcagca | tgctaacgag | tcacagcgtt | tatgcagaag | 1200 |

```
tgatgcctgg atgcctgttg cagctgttta cggcactgcc ttgcagtgag cattgcagat      1260
aggggtgggg tgctttgtgt cgtgttccca cacgctgcca cacagccacc tcccggaaca      1320
catctcacct gctgggtact tttcaaacca tcttagcagt agtagatgag ttactatgaa      1380
acagagaagt tcctcagttg gatattctca tgggatgtct ttttttcccat gttgggcaaa      1440 gtatgataaa gcatctctat ttgtaaatta tgcacttgtt agttcctgaa tcctttctat      1500
agcaccactt attgcagcag gtgtaggctc tggtgtggcc tgtgtctgtg cttcaatctt      1560
ttaaagcttc tttggaaata cactgacttg attgaagtct cttgaagata gtaaacagta      1620
cttacctttg atcccaatga aatcgagcat ttcagttgta aaagaattcc gcctattcat      1680
accatgtaat gtaattttac accccccagtg ctgacactttt ggaatatatt caagtaatag      1740
actttggcct caccctcttg tgtactgtat tttgtaatag aaaatatttt aaactgtgca      1800
tatgattatt acattatgaa agagacattc tgctgatctt caaatgtaag aaaatgagga      1860
gtgcgtgtgc ttttataaat acaagtgatt gcaaattagt gcaggtgtcc ttaaaaaaaa      1920 aaaaaaaag taatataaaa aggaccaggt gttttacaag tgaaatacat tcctatttgg      1980
taaacagtta catttttatg aagattacca gcgctgctga ctttctaaac ataaggctgt      2040
attgtcttcc tgtaccattg catttcctca ttcccaattt gcacaaggat gtctgggtaa      2100
actattcaag aaatggcttt gaaatacagc atggagcttt gtctgagttg aatgcagag       2160 ttgcactgca aaatgtcagg aaatggatgt ctctcagaat gcccaactcc aaaggatttt      2220
atatgtgtat atagtaagca gtttcctgat tccagcaggc caaagagtct gctgaatgtt      2280
gtgttgccgg agacctgtat ttctcaacaa ggtaagatgg tatcctagca actgcggatt      2340
ttaatacatt ttcagcagaa gtacttagtt aatctctacc tttagggatc gtttcatcat      2400
ttttagatgt tatacttgaa atactgcata acttttagct ttcatgggtt cctttttttc      2460
agcctttagg agactgttaa gcaatttgct gtccaacttt tgtgttggtc ttaaactgca      2520
atagtagttt accttgtatt gaagaaataa agaccatttt tatattaaaa aatacttttg      2580
tctgtcttca ttttgacttg tctgatatcc ttgcagtgcc cattatgtca gttctgtcag      2640
atattcagac atcaaaactt aacgtgagct cagtggagtt acagctgcgg ttttgatgct      2700
gttattattt ctgaaactag aaatgatgtt gtcttcatct gctcatcaaa cacttcatgc      2760
agagtgtaag gctagtgaga aatgcataca tttattgata cttttttaaa gtcaacttttt      2820 tatcagattt ttttttcatt tggaaatata ttgttttcta gactgcatag cttctgaatc      2880
tgaaatgcag tctgattggc atgaagaagc acagcactct tcatcttact taaacttcat      2940
tttggaatga aggaagttaa gcaagggcac aggtccatga aatagagaca gtgcgctcag      3000
gagaaagtga acctggattt ctttggctag tgttctaaat ctgtagtgag gaaagtaaca      3060
cccgattcct tgaaagggct ccagctttaa tgcttccaaa ttgaaggtgg caggcaactt      3120
ggccactggt tatttactgc attatgtctc agtttcgcag ctaacctggc ttctccacta      3180
ttgagcatgg actatagcct ggcttcagag gccaggtgaa ggttgggatg ggtggaagga      3240
gtgctgggct gtggctgggg ggactgtggg gactccaagc tgagcttggg gtgggcagca      3300
cagggaaaag tgtgggtaac tatttttaag tactgtgttg caaacgtctc atctgcaaat      3360
acgtagggtg tgtactctcg aagattaaca gtgtgggttc agtaatatat ggatgaattc      3420
acagtggaag cattcaaggg tagatcatct aacgacacca gatcatcaag ctatgattgg      3480
aagcggtatc agaagagcga ggaaggtaag cagtcttcat atgttttccc tccacgtaaa      3540
```

-continued

```
gcagtctggg aaagtagcac cccttgagca gagacaagga aataattcag gagcatgtgc    3600
taggagaact ttcttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg ttttgtttg gcgtttggtt    4080 ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt tgagaagat ggcagttgct     4500 tctttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
tctgaggaac gggcagcgtt tgcctctgaa agcaaggagc tctgcggagt gcagttatt    4800 ttgcaactga tggtggaact ggtgcttaaa gcagattccc taggttccct gctacttctt    4860
ttccttcttg gcagtcagtt tatttctgac agacaaacag ccaccccac tgcaggctta    4920 gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttttta aatacataaa    5280 ctacttcaaa tgaggtcgga gaaggtcagt gttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt taccccctga ctgttccatt    5580
cagcggtttg gaaagagaaa aagaatttgg aaataaaaca tgtctacgtt atcacctcct    5640
ccagcatttt ggttttttaat tatgtcaata actggcttag attggaaat gagaggggt     5700 tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
```

```
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta aatacagcc tggggtaaga    6300 agttcagtct cctgctggga cagctaaccg catcttataa cccttctga gactcatctt    6360 aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt ccttcccca    6540 ctgtgtttaa cccttaagg cattcagaac aactagaatc atagaatggt ttggattgga    6600
agggccctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agaccccttg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat ttgggatcag    7500
ttaccttttg gggtaagctt ttgtatctgc agagaccctg ggggtctga tgtgcttcag    7560 ctctgctctg ttctgactgc accattttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca caagaaaaga gattcctttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaactttc tggtgaattg    8280
```

```
cgtggagaat catgatggca gttcttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaaccttt ggcctgactg atgcctcccg    8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
tttttcttcc tgctgtcagg aacattttga ataccagaga aaagaaaag tgctcttctt    8820
ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcattttt ataggacttc caggaaggat cttcttctta agcttcttaa ttatggtaca    9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
tctggctatg aaagtctgct tacaaggaag aggataaaaa tcatagggat aataaatcta    9420
agtttgaaga caatgaggtt ttagctgcat ttgacatgaa gaaattgaga cctctactgg    9480
atagctatgg tatttacgtg tcttttttgct tagttactta ttgaccccag ctgaggtcaa    9540
gtatgaactc aggtctctcg ggctactggc atggattgat tacatacaac tgtaatttta    9600
gcagtgattt agggtttatg agtacttttg cagtaaatca tagggttagt aatgttaatc    9660
tcagggaaaa aaaaaaaag ccaaccctga cagacatccc agctcaggtg gaaatcaagg    9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaattttct ctccgctgca cagttccagt catcccagtt tgtacagttc    9900
tggcactttt tgggtcaggc cgtgatccaa ggagcagaag ttccagctat ggtcagggag    9960
tgcctgaccg tcccaactca ctgcactcaa acaaaggcga aaccacaaga gtggcttttg   10020
ttgaaattgc agtgtggccc agaggggctg caccagtact ggattgacca cgaggcaaca   10080
ttaatcctca gcaagtgcaa tttgcagcca ttaaattgaa ctaactgata ctacaatgca   10140
atcagtatca acaagtggtt tggcttggaa gatggagtct aggggctcta caggagtagc   10200
tactctctaa tggagttgca ttttgaagca ggacactgtg aaaagctggc ctcctaagaa   10260
ggctgctaaa cattagggtc aattttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttatttat   10500
gcccactaga acatcttgt acaagctgaa cactgggct ccagattagt ggtaaaacct   10560
actttataca atcatagaat catagaatgg cctgggttgg aagggacccc aaggatcatg   10620
aagatccaac acccccgcca caggcagggc caccaacctc cagatctggt actagaccag   10680
```

```
gcagcccagg gctccatcca acctggccat gaacacctcc agggatggag catccacaac    10740
ctctctgggc agcctgtgcc agcacctcac caccctctct gtgaagaact tttccctgac    10800
atccaatcta agccttccct ccttgaggtt agatccactc ccccttgtgc tatcactgtc    10860
tactcttgta aaagttgat tctcctcctt tttggaaggt tgcaatgagg tctccttgca     10920
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgatacctc accccacctg ccactgaatg gctccatggc ccctgcagc    11400 cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttttga caactgtaga acagaggaat caaaagggggg   11820 tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
taggg                                                                11945
```

<210> SEQ ID NO 68
<211> LENGTH: 285
<212> TYPE: DNA
<213> ORGANISM: SV40
<220> FEATURE:
<221> NAME/KEY: misc_feature
<222> LOCATION: (1)..(285)
<223> OTHER INFORMATION: SV40 Polyadenylation Sequence

<400> SEQUENCE: 68

```
aaagtctaga gtcggggcgg ccggccgctt cgagcagaca tgataagata cattgatgag      60
tttggacaaa ccacaactag aatgcagtga aaaaaatgct ttatttgtga aatttgtgat     120
gctattgctt tatttgtaac cattataagc tgcaataaac aagttaacaa caacaattgc     180
attcatttta tgtttcaggt tcaggggag gtgtgggagg ttttttaaag caagtaaaac      240
ctctacaaat gtggtaaaat cgataaggat ccgtcgagcg gccgc                     285
```

<210> SEQ ID NO 69
<211> LENGTH: 5972
<212> TYPE: DNA
<213> ORGANISM: Gallus gallus

<400> SEQUENCE: 69

```
cgcgtggtag gtggcggggg gttcccagga gagcccccag cgcggacggc agcgccgtca      60
ctcaccgctc cgtctccctc cgcccagggt cgcctggcgc aaccgctgca agggcaccga     120
```

-continued

```
cgtccaggcg tggatcagag gctgccggct gtgaggagct gccgcgcccg gcccgcccgc      180
tgcacagccg gccgctttgc gagcgcgacg ctacccgctt ggcagtttta aacgcatccc      240
tcattaaaac gactatacgc aaacgccttc ccgtcggtcc gcgtctcttt ccgccgccag      300
ggcgacactc gcggggaggg cgggaagggg gccggcgggg agcccgcggc caaccgtcgc      360
cccgtgacgg caccgccccg cccccgtgac gcggtgcggg cgccggggcc gtggggctga      420
gcgctgcggc ggggccgggc cgggccgggg cgggagctga gcgcggcgcg gctgcgggcg      480
gcgccccctc cggtgcaata tgttcaagag aatggctgag ttcgggcctg actccggggg      540
cagggtgaag gtgcggcgcg ggcggaggga cgggcgggc gcggggccgc ccggcgggtg       600
ccggggcctc tgccgcccg cccggctcgg gctgctgcgg cgcttacggg cgcgcttctc       660
gccgctgccg cttctcttct ctcccgcgca agggcgtcac catcgtgaag ccggtagtgt      720
acgggaacgt ggcgcggtac ttcgggaaga gagggagga ggacgggcac acgcatcagt      780
ggacggttta cgtgaagccc tacaggaacg aggtagggcc cgagcgcgtc ggccgccgtt      840
ctcggagcgc cggagccgtc agcgccgcgc ctgggtgcgc tgtgggacac agcgagcttc      900
tctcgtagga catgtccgcc tacgtgaaaa aaatccagtt caagctgcac gagagctacg      960
ggaatcctct ccgaggtggg tgttgcgtcg ggggtttgc tccgctcggt cccgctgagg      1020
ctcgtcgccc tcatctttct ttcgtgccgc agtcgttacc aaaccgccgt acgagatcac      1080
cgaaacgggc tggggcgaat ttgaaatcat catcaagata ttttcattg atccaaacga      1140 gcgacccgta agtacgctca gcttctcgta gtgcttcccc cgtcctggcg gcccggggct      1200
gggctgctcg ctgctgccgg tcacagtccc gccagccgcg gagctgactg agctcccttt      1260
cccgggacgt gtgctctgtg ttcggtcagc gaggctatcg ggagggcttt ggctgcattt      1320
ggcttctctg gcgcttagcg caggagcacg ttgtgctacg cctgaactac agctgtgaga      1380
aggccgtgga aaccgctctc aaactgattt attggcgaaa tggctctaaa ctaaatcgtc      1440
tcctctcttt ggaaatgctt tagagaaggt ctctgtggta gttcttatgc atctatccta     1500
aagcacttgg ccagacaatt taaagacatc aagcagcatt tatagcaggc acgtttaata    1560
acgaatactg aatttaagta actctgctca cgttgtatga cgtttatttt cgtattcctg    1620
aaagccatta aaatcctgtg cagttgttta gtaagaacag ctgccactgt tttgtatcta    1680
ggagataact ggtgtttccc tacagttctc aagctgataa aactctgtct ttgtatctag    1740
gtaaccctgt atcacttgct gaagcttttt cagtctgaca ccaatgcaat cctgggaaag    1800
aaaactgtag tttctgaatt ctatgatgaa atggtatgaa aattttaatg tcaaccgagc    1860
ctgactttat ttaaaaaaaa ttattgatgg tgctgtgtat tttggtcctt ccttagatat    1920
ttcaagatcc tactgccatg atgcagcaac tgctaacgac gtcccgtcag ctgacacttg    1980
gtgcttacaa gcatgaaaca gagtgtaagt gcaaaatgag gataccttcg ccgaccgtca    2040
ttcactacta atgttttctg tgggatgtga tcgtacagtg agtttggctg tgtgaaattt    2100
gaatagcttg gtattggcag tgatgacgtg atcgatgcct tgcttatcat gtttgaaatg    2160
aagtagaata aatgcagcct gctttatttg agatagtttg gttcatttta tggaatgcaa    2220
gcaaagatta tacttcctca ctgaattgca ctgtccaaag gtgtgaaatg tgtgggatc     2280 tggaggaccg tgaccgaggg acattggatc gctatctccc atttcttttg ctgttaccag    2340
ttcagatttt cttttcacct agtctttaat tcccagggtt ttgttttttc cttggtcata    2400 gttttttgttt ttcactctgg caaatgatgt tgtgaattac actgcttcag ccacaaaact    2460
gatggactga atgaggtcat caaacaaact tttcttcttc cgtatttcct tttttttccc    2520
```

-continued

```
ccacttatca tttttactgc tgttgttgag tctgtaaggc taaaagtaac tgttttgtgc    2580
tttttcagga cgtgtgcttt ccaaattact gccacatata taaagaaagg ttggaatttt    2640
aaagataatt catgtttctt cttctttttt gccaccacag ttgcagatct tgaagtaaaa    2700
accagggaaa agctggaagc tgccaaaaag aaaaccagtt ttgaaattgc tgagcttaaa    2760
gaaaggttaa aagcaagtcg tgaaaccatc aactgcttaa agagtgaaat cagaaaactc    2820
gaagaggatg atcagtctaa agatatgtga tgagtgttga cttggcaggg agcctataat    2880
gagaatgaaa ggacttcagt cgtggagttg tatgcgttct ctccaattct gtaacggaga    2940
ctgtatgaat ttcatttgca aatcactgca gtgtgtgaca actgacttt tataaatggc     3000 agaaaacaag aatgaatgta tcctcatttt atagttaaaa tctatgggta tgtactggtt    3060
tatttcaagg agaatggatc gtagagactt ggaggccaga ttgctgcttg tattgactgc    3120
atttgagtgg tgtaggaaca ttttgtctat ggtcccgtgt tagtttacag aatgccactg    3180
ttcactgttt tgttttgtat tttacttttt ctactgcaac gtcaaggttt taaaagttga    3240
aaataaaaca tgcaggtttt ttttaaatat tttttgtct ctatccagtt tgggcttcaa     3300
gtattattgt taacagcaag tcctgattta agtcagaggc tgaagtgtaa tggtattcaa    3360
gatgcttaag tctgttgtca gcaaaacaaa agagaaaact tcataaaatc aggaagttgg    3420
catttctaat aacttcttta tcaacagata agagtttcta gccctgcatc tactttcact    3480
tatgtagttg atgccttat attttgtgtg tttggatgca ggaagtgatt cctactctgt     3540
tatgtagata ttctatttaa cacttgtact ctgctgtgct tagcctttcc ccatgaaaat    3600
tcagcggctg taaatccccc tcttcttttg tagcctcata cagatggcag accctcaggc    3660
ttataaaggc ttgggcatct tctttactgc tttgagattc tgtgttgcag taacctctgc    3720
cagagaggag aaaagcccca caaacctcat ccccttcttc tatagcaatc agtattacta    3780
atgctttgag aacagagcac tggtttgaaa cgtttgataa ttagcattta acatggcttg    3840
gtaaagatgc agaactgaaa cagctgtgac agtatgaact cagtatggag acttcattaa    3900
gacaaacagc tgttaaaatc aggcatgttt cattgaggag gacggggcaa cttgcaccag    3960
tggtgcccac acaaatcctt cctggcgctg cagaccaatt tttctggcat tctgactgcc    4020
gttgctgctg tcacagaga gcaactattt ttatcagcca caggcaattt gcttgtagta     4080
ttttccaagt gttgtaggta agtataaatg catcggctcc agagcacttt gagtatactt    4140
attaaaaaca taaatgaaag acaaattagc tttgcttggg tgcacagaac attttagtt     4200 ccagcctgct ttttggtaga agccctcttc tgaggctaga actgactttg acaagtagag    4260
aaactggcaa cggagctatt gctatcgaag gatccttgtt aacaaagtta atcgtctttt    4320
aaggtttggt ttattcatta aatttgcttt taagctgtag ctgaaaaaga acgtgctgtc    4380
ttccatgcac caggtggcag ctctgtgcaa agtgctctct ggtctcacca gccttttaat    4440
tgccgggatt ctggcacgtc tgagagggct cagactggct tcgtttgttt gaacagcgtg    4500
tactgctttc tgtagacatg gccggttct ctcctgcagc ttatgaaact gttcacactg     4560
aacacactgg aacaggttgc ccaaggaggc cgtggatgcc ccatccctgg aggcattcaa    4620
ggccaggctg gatgtggctc tgggcagcct ggtctggtgg ttgcgatcc tgcacatagc     4680 agcggggttg aaactcgatg atcactgtgg tccttttcaa cccaggctat tctatgattc    4740
tatgattcaa cagcaaatca tatgtactga gagaggaaac aaaacacaagt gctactgttt    4800 gcaagttttg ttcatttggt aaaagagtca ggttttaaaa ttcaaaatct gtctggtttt    4860
```

```
ggtgtttttt tttttttatt tattatttct ttgggtttct ttttgatgct ttatctttct    4920
ctgccaggac tgtgtgacaa tgggaacgaa aagaacatg ccaggcactg tcctggattg     4980
cacacgctgg ttgcactcag tagcaggctc agaactgcca gtctttccac agtattactt   5040
tctaaaccta atttttaatag cgttagtaga cttccatcac tgggcagtgc ttagtgaatg  5100
ctctgtgtga acgttttact tataagcatg ttggaagttt tgatgttcct ggatgcagta   5160
gggaaggaca gattagctat gtgaaaagta gattctgagt atcggggtta caaaaagtat   5220
agaaacgatg agaaattctt gttgtaacta attggaattt ctttaagcgt tcacttatgc   5280
tacattcata gtatttccat ttaaaagtag gaaaaggtaa aacgtgaaat cgtgtgattt   5340
tcggatggaa caccgccttc ctatgcacct gaccaacttc cagaggaaaa gcctattgaa   5400
agccgagatt aagccaccaa aagaactcat ttgcattgga atatgtagta tttgccctct   5460
tcctcccggg taattactat actttatagg gtgcttatat gttaaatgag tggctggcac   5520 ttttattct cacagctgtg gggaattctg tcctctagga cagaaacaat tttaatctgt    5580
tccactggtg actgctttgt cagcacttcc acctgaagag atcaatacac tcttcaatgt   5640
ctagttctgc aacacttggc aaacctcaca tcttatttca tactctcttc atgcctatgc   5700
ttattaaagc aataatctgg gtaattttg ttttaatcac tgtcctgacc ccagtgatga    5760
ccgtgtccca cctaaagctc aattcaggtc ctgaatctct tcaactctct atagctaaca   5820
tgaagaatct tcaaaagtta ggtctgaggg acttaaggct aactgtagat gttgttgcct   5880
ggtttctgtg ctgaaggccg tgtagtagtt agagcattca acctctagaa gaagcttggc   5940
cagctggtcg acctgcagat ccggccctcg ag                                 5972

<210> SEQ ID NO 70
<211> LENGTH: 18391
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription enhancer
<220> FEATURE:
<221> NAME/KEY: misc_feature
<222> LOCATION: (9160)..(9325)
<223> OTHER INFORMATION: Transcription enhancer
<220> FEATURE:
<221> NAME/KEY: misc_feature
<222> LOCATION: (9326)..(9626)
<223> OTHER INFORMATION: Negative regulatory element
```

```
<220> FEATURE:
<221> NAME/KEY: misc_feature
<222> LOCATION: (9621)..(9660)
<223> OTHER INFORMATION: Hormone response element
<220> FEATURE:
<221> NAME/KEY: misc_feature
<222> LOCATION: (9680)..(10060)
<223> OTHER INFORMATION: Hormone response element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11846)..(12443)
<223> OTHER INFORMATION: Human Interferon alpha 2b encoding region codon
      optimized for expression in chicken cells (IFNMAGMAX
<220> FEATURE:
<221> NAME/KEY: misc_feature
<222> LOCATION: (12464)..(18391)
<223> OTHER INFORMATION: Chicken Lysozyme 3prime domain

<400> SEQUENCE: 70
tgccgccttc tttgatattc actctgttgt atttcatctc ttcttgccga tgaaaggata    60
taacagtctg tataacagtc tgtgaggaaa tacttggtat ttcttctgat cagtgttttt   120
ataagtaatg ttgaatattg gataaggctg tgtgtccttt gtcttgggag acaaagccca   180
cagcaggtgg tggttggggt ggtggcagct cagtgacagg agaggttttt ttgcctgttt   240
tttttttttt tttttttttt aagtaaggtg ttcttttttc ttagtaaatt ttctactgga   300
ctgtatgttt tgacaggtca gaaacatttc ttcaaaagaa gaaccttttg gaaactgtac   360 agccctttc ttttcattcc tttttgcttt ctgtgccaat gcctttggtt ctgattgcat   420 tatgaaaac gttgatcgga acttgaggtt tttatttata gtgtggcttg aaagcttgga   480
tagctgttgt tacacgagat accttattaa gtttaggcca gcttgatgct ttattttttc   540
cctttgaagt agtgagcgtt ctctggtttt tttcctttga aactggtgag cttagatt    600 ttctaatggg attttttacc tgatgatcta gttgcatacc caaatgcttg taaatgtttt   660
cctagttaac atgttgataa cttcggattt acatgttgta tacttgtc atctgtgttt   720 ctagtaaaaa tatatggcat ttatagaaat acgtaattcc tgatttcctt ttttttatc   780 tctatgctct gtgtgtacag gtcaaacaga cttcactcct atttttattt atagaattt   840 atatgcagtc tgtcgttggt tcttgtgttg taaggataca gccttaaatt tcctagagcg   900
atgctcagta aggcgggttg tcacatgggt tcaaatgtaa acgggcacg tttggctgct    960 gccttcccga gatccaggac actaaactgc ttctgcactg aggtataaat cgcttcagat  1020
cccagggaag tgcagatcca cgtgcatatt cttaaagaag aatgaatact ttctaaaata  1080
ttttggcata ggaagcaagc tgcatggatt tgtttgggac ttaaattatt ttggtaacgg  1140
agtgcatagg ttttaaacac agttgcagca tgctaacgag tcacagcgtt tatgcagaag  1200
tgatgcctgg atgcctgttg cagctgttta cggcactgcc ttgcagtgag cattgcagat  1260 agggtgggg tgcttgtgt cgtgttccca cacgctgcca cacagccacc tcccggaaca  1320
catctcacct gctgggtact tttcaaacca tcttagcagt agtagatgag ttactatgaa  1380
```

```
acagagaagt tcctcagttg gatattctca tgggatgtct ttttttcccat gttgggcaaa   1440
gtatgataaa gcatctctat ttgtaaatta tgcacttgtt agttcctgaa tcctttctat   1500
agcaccactt attgcagcag gtgtaggctc tggtgtggcc tgtgtctgtg cttcaatctt   1560
ttaaagcttc tttggaaata cactgacttg attgaagtct cttgaagata gtaaacagta   1620
cttacctttg atcccaatga aatcgagcat ttcagttgta aaagaattcc gcctattcat   1680
accatgtaat gtaattttac accccagtg ctgacacttt ggaatatatt caagtaatag   1740
actttggcct caccctcttg tgtactgtat tttgtaatag aaaatatttt aaactgtgca   1800
tatgattatt acattatgaa agagacattc tgctgatctt caaatgtaag aaaatgagga   1860
gtgcgtgtgc ttttataaat acaagtgatt gcaaattagt gcaggtgtcc ttaaaaaaaa   1920
aaaaaaaag taatataaaa aggaccaggt gttttacaag tgaaatacat tcctatttgg   1980
taaacagtta cattttatg aagattacca gcgctgctga ctttctaaac ataaggctgt   2040
attgtcttcc tgtaccattg catttcctca ttcccaattt gcacaaggat gtctgggtaa   2100
actattcaag aaatggcttt gaaatacagc atgggagctt gtctgagttg aatgcagag   2160
ttgcactgca aaatgtcagg aaatggatgt ctctcagaat gcccaactcc aaaggatttt   2220
atatgtgtat atagtaagca gtttcctgat tccagcaggc caaagagtct gctgaatgtt   2280
gtgttgccgg agacctgtat ttctcaacaa ggtaagatgg tatcctagca actgcggatt   2340
ttaatacatt ttcagcagaa gtacttagtt aatctctacc tttagggatc gtttcatcat   2400
ttttagatgt tatacttgaa atactgcata acttttagct ttcatgggtt ccttttttc   2460
agcctttagg agactgttaa gcaatttgct gtccaacttt tgtgttggtc ttaaactgca   2520
atagtagttt accttgtatt gaagaaataa agaccatttt tatattaaaa aatacttttg   2580
tctgtcttca ttttgacttg tctgatatcc ttgcagtgcc cattatgtca gttctgtcag   2640
atattcagac atcaaaactt aacgtgagct cagtggagtt acagctgcgg ttttgatgct   2700
gttattattt ctgaaactag aaatgatgtt gtcttcatct gctcatcaaa cacttcatgc   2760
agagtgtaag gctagtgaga aatgcataca tttattgata ctttttttaaa gtcaactttt   2820
tatcagattt ttttttcatt tggaaatata ttgttttcta gactgcatag cttctgaatc   2880
tgaaatgcag tctgattggc atgaagaagc acagcactct tcatcttact taaacttcat   2940
tttggaatga aggaagttaa gcaagggcac aggtccatga aatagagaca gtgcgctcag   3000
gagaaagtga acctggatt ctttggctag tgttctaaat ctgtagtgag gaaagtaaca   3060
cccgattcct tgaaagggct ccagcttta tgcttccaaa ttgaaggtgg caggcaactt   3120
ggccactggt tatttactgc attatgtctc agtttcgcag ctaacctggc ttctccacta   3180
ttgagcatgg actatagcct ggcttcagag gccaggtgaa ggttgggatg ggtggaagga   3240
gtgctgggct gtggctgggg ggactgtggg gactccaagc tgagcttggg gtgggcagca   3300
cagggaaaag tgtgggtaac tatttttaag tactgtgttg caaacgtctc atctgcaaat   3360
acgtagggtg tgtactctcg aagattaaca gtgtgggttc agtaatatat ggatgaattc   3420
acagtggaag cattcaaggg tagatcatct aacgacacca gatcatcaag ctatgattgg   3480
aagcggtatc agaagagcga ggaaggtaag cagtcttcat atgtttccc tccacgtaaa   3540
gcagtctggg aaagtagcac cccttgagca gagacaagga aataattcag gagcatgtgc   3600
taggagaact tcttgctga attctacttg caagagcttt gatgcctggc ttctggtgcc   3660
ttctgcagca cctgcaaggc ccagagcctg tggtgagctg gagggaaaga ttctgctcaa   3720
gtccaagctt cagcaggtca ttgtctttgc ttcttccccc agcactgtgc agcagagtgg   3780
```

```
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500
tctttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta    4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttttta aatacataaa    5280
ctacttcaaa tgaggtcgga gaaggtcagt gttttattag cagccataaa accaggtgag    5340
cgagtaccat ttttctctac aagaaaaacg attctgagct ctgcgtaagt ataagttctc    5400
catgcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt taccccctga ctgttccatt    5580
cagcggtttg gaaagagaaa aagaatttgg aaataaaaca tgtctacgtt atcacctcct    5640
ccagcatttt ggttttttaat tatgtcaata actggcttag atttggaaat gagaggggt    5700
tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
```

-continued

```
atggaagctt atttattttt cgttcttcca tatcagtctt ctctatgaca attcacatcc   6180
accacagcaa attaaaggtg aaggaggctg gtgggatgaa gagggtcttc tagctttacg   6240
ttcttccttg caaggccaca ggaaaatgct gagagctgta gaatacagcc tggggtaaga   6300
agttcagtct cctgctggga cagctaaccg catcttataa cccttctga gactcatctt    6360
aggaccaaat agggtctatc tggggttttt gttcctgctg ttcctcctgg aaggctatct   6420
cactatttca ctgctcccac ggttacaaac caaagataca gcctgaattt tttctaggcc   6480
acattacata aatttgacct ggtaccaata ttgttctcta tatagttatt tccttcccca   6540
ctgtgtttaa ccccttaagg cattcagaac aactagaatc atagaatggt ttggattgga   6600
aggggcctta aacatcatcc atttccaacc ctctgccatg ggctgcttgc cacccactgg   6660
ctcaggctgc ccaggccccc atccagcctg gccttgagca cctccaggga tggggcaccc   6720
acagcttctc tgggcagcct gtgccaacac ctcaccactc tctgggtaaa gaattctctt   6780
ttaacatcta atctaaatct cttctctttt agtttaaagc cattcctctt tttcccgttg   6840
ctatctgtcc aagaaatgtg tattggtctc cctcctgctt ataagcagga agtactggaa   6900
ggctgcagtg aggtctcccc acagccttct cttctccagg ctgaacaagc ccagctcctt   6960
cagcctgtct tcgtaggaga tcatcttagt ggccctcctc tggacccatt ccaacagttc   7020
cacggctttc ttgtggagcc ccaggtctgg atgcagtact tcagatgggg ccttacaaag   7080
gcagagcaga tggggacaat cgcttacccc tccctgctgg ctgccctgt tttgatgcag    7140
cccagggtac tgttggcctt tcaggctccc agacccctg ctgatttgtg tcaagctttt    7200
catccaccag aacccacgct tcctggttaa tacttctgcc ctcacttctg taagcttgtt   7260
tcaggagact tccattcttt aggacagact gtgttacacc tacctgccct attcttgcat   7320
atatacattt cagttcatgt ttcctgtaac aggacagaat atgtattcct ctaacaaaaa   7380
tacatgcaga attcctagtg ccatctcagt agggttttca tggcagtatt agcacatagt   7440
caatttgctg caagtacctt ccaagctgcg gcctcccata aatcctgtat ttgggatcag   7500
ttacctttg gggtaagctt ttgtatctgc agagaccctg ggggtctga tgtgcttcag    7560
ctctgctctg ttctgactgc accattttct agatcaccca gttgttcctg tacaacttcc   7620
ttgtcctcca tcctttccca gcttgtatct ttgacaaata caggcctatt tttgtgtttg   7680
cttcagcagc catttaattc ttcagtgtca tcttgttctg ttgatgccac tggaacagga   7740
ttttcagcag tcttgcaaag aacatctagc tgaaaacttt ctgccattca atattcttac   7800
cagttcttct tgtttgaggt gagccataaa ttactagaac ttcgtcactg acaagtttat   7860
gcattttatt acttctatta tgtacttact ttgacataac acagacacgc acatattttg   7920
ctgggatttc cacagtgtct ctgtgtcctt cacatggttt tactgtcata cttccgttat   7980
aaccttggca atctgcccag ctgcccatca aagaaaaga gattccttt ttattacttc     8040
tcttcagcca ataaacaaaa tgtgagaagc ccaaacaaga acttgtgggg caggctgcca   8100
tcaagggaga gacagctgaa gggttgtgta gctcaataga attaagaaat aataaagctg   8160
tgtcagacag ttttgcctga tttatacagg cacgccccaa gccagagagg ctgtctgcca   8220
aggccacctt gcagtccttg gtttgtaaga taagtcatag gtaacttttc tggtgaattg   8280
cgtggagaat catgatggca gttccttgctg tttactatgg taagatgcta aaataggaga   8340
cagcaaagta acacttgctg ctgtaggtgc tctgctatcc agacagcgat ggcactcgca   8400
caccaagatg agggatgctc ccagctgacg gatgctgggg cagtaacagt gggtcccatg   8460
ctgcctgctc attagcatca cctcagccct caccagccca tcagaaggat catcccaagc   8520
```

```
tgaggaaagt tgctcatctt cttcacatca tcaaacctttt ggcctgactg atgcctcccg    8580
gatgcttaaa tgtggtcact gacatctttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
tttttcttcc tgctgtcagg aacattttga ataccagaga aaaagaaaag tgctcttctt    8820
ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc    9060
cgctgaagga atccagctcc tgtttgagca ggtgctgcac actcccacac tgaaacaaca    9120
gttcattttt ataggacttc caggaaggat cttcttctta agcttcttaa ttatggtaca    9180
tctccagttg gcagatgact atgactactg acaggagaat gaggaactag ctgggaatat    9240
ttctgtttga ccaccatgga gtcacccatt tctttactgg tatttggaaa taataattct    9300
gaattgcaaa gcaggagtta gcgaagatct tcatttcttc catgttggtg acagcacagt    9360
tctggctatg aaagtctgct tacaaggaag aggataaaaa tcatagggat aataaatcta    9420
agtttgaaga caatgaggtt ttagctgcat ttgacatgaa gaaattgaga cctctactgg    9480
atagctatgg tatttacgtg tcttttttgct tagttactta ttgacccccag ctgaggtcaa    9540 gtatgaactc aggtctctcg ggctactggc atggattgat tacatacaac tgtaattta    9600 gcagtgattt agggtttatg agtacttttg cagtaaatca tagggttagt aatgttaatc    9660
tcagggaaaa aaaaaaaag ccaaccctga cagacatccc agctcaggtg gaaatcaagg    9720
atcacagctc agtgcggtcc cagagaacac agggactctt ctcttaggac ctttatgtac    9780
agggcctcaa gataactgat gttagtcaga agactttcca ttctggccac agttcagctg    9840
aggcaatcct ggaattttct ctccgctgca cagttccagt catcccagtt tgtacagttc    9900
tggcactttt tgggtcaggc cgtgatccaa ggagcagaag ttccagctat ggtcagggag    9960
tgcctgaccg tcccaactca ctgcactcaa acaaaggcga aaccacaaga gtggcttttg   10020
ttgaaattgc agtgtggccc agaggggctg caccagtact ggattgacca cgaggcaaca   10080
ttaatcctca gcaagtgcaa tttgcagcca ttaaattgaa ctaactgata ctacaatgca   10140
atcagtatca acaagtggtt tggcttggaa gatggagtct agggggctcta caggagtagc   10200 tactctctaa tggagttgca ttttgaagca ggacactgtg aaaagctggc ctcctaaaga   10260
ggctgctaaa cattagggtc aatttttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttatttat   10500
gcccactaga aacatcttgt acaagctgaa cactggggct ccagattagt ggtaaaacct   10560
actttataca atcatagaat catagaatgg cctgggttgg aagggacccc aaggatcatg   10620
aagatccaac accccgcca caggcagggc caccaacctc cagatctggt actagaccag   10680
gcagcccagg gctccatcca acctggccat gaacacctcc agggatggag catccacaac   10740
ctctctgggc agcctgtgcc agcacctcac caccctctct gtgaagaact tttccctgac   10800
atccaatcta agccttccct ccttgaggtt agatccactc ccccttgtgc tatcactgtc   10860
```

```
tactcttgta aaaagttgat tctcctcctt tttggaaggt tgcaatgagg tctccttgca  10920
gccttcttct cttctgcagg atgaacaagc ccagctccct cagcctgtct ttataggaga  10980
ggtgctccag ccctctgatc atctttgtgg ccctcctctg gacccgctcc aagagctcca  11040
catctttcct gtactgggggg ccccaggcct gaatgcagta ctccagatgg ggcctcaaaa  11100
gagcagagta aagagggaca atcaccttcc tcaccctgct ggccagccct cttctgatgg  11160
agccctggat acaactggct ttctgagctg caacttctcc ttatcagttc cactattaaa  11220
acaggaacaa tacaacaggt gctgatggcc agtgcagagt ttttcacact tcttcatttc  11280
ggtagatctt agatgaggaa cgttgaagtt gtgcttctgc gtgtgcttct tcctcctcaa  11340
atactcctgc ctgataccct accccacctg ccactgaatg gctccatggc cccctgcagc  11400
cagggccctg atgaacccgg cactgcttca gatgctgttt aatagcacag tatgaccaag  11460
ttgcacctat gaatacacaa acaatgtgtt gcatccttca gcacttgaga agaagagcca  11520
aatttgcatt gtcaggaaat ggtttagtaa ttctgccaat taaaacttgt ttatctacca  11580
tggctgtttt tatggctgtt agtagtggta cactgatgat gaacaatggc tatgcagtaa  11640
aatcaagact gtagatattg caacagacta taaaattcct ctgtggctta gccaatgtgg  11700
tacttcccac attgtataag aaatttggca gtttagagc aatgtttgaa gtgttgggaa  11760
atttctgtat actcaagagg gcgtttttga caactgtaga acagaggaat caaaagggggg  11820 tgggaggaag ttaaaagaag aggcaggtgc aagagagctt gcagtcccgc tgtgtgtacg  11880
acactggcaa catgaggtct ttgctaatct tggtgctttg cttcctgccc ctggctgcct  11940
tagggtgcga tctgcctcag acccacagcc tgggcagcag gaggaccctg atgctgctgg  12000
ctcagatgag gagaatcagc ctgtttagct gcctgaagga taggcacgat tttggctttc  12060
ctcaagagga gtttggcaac cagtttcaga aggctgagac catccctgtg ctgcacgaga  12120
tgatccagca gatctttaac ctgtttagca ccaaggatag cagcgctgct tgggatgaga  12180
ccctgctgga taagttttac accgagctgt accagcagct gaacgatctg gaggcttgcg  12240
tgatccaggg cgtgggcgtg accgagaccc ctctgatgaa ggaggatagc atcctggctg  12300
tgaggaagta ctttcagagg atcacccctgt acctgaagga gaagaagtac agcccctgcg  12360
cttgggaagt cgtgagggct gagatcatga ggagctttag cctgagcacc aacctgcaag  12420
agagcttgag gtctaaggag taaaaagtct agagtcgggg cggcgcgtgg taggtggcgg  12480
ggggttccca ggagagcccc cagcgcggac ggcagcgccg tcactcaccg ctccgtctcc  12540
ctccgcccag ggtcgcctgg cgcaaccgct gcaagggcac cgacgtccag gcgtggatca  12600
gaggctgccg gctgtgagga gctgccgcgc ccggcccgcc cgctgcacag ccggccgctt  12660
tgcgagcgcg acgctacccg cttggcagtt ttaaacgcat ccctcattaa aacgactata  12720
cgcaaacgcc ttcccgtcgg tccgcgtctc tttccgccgc cagggcgaca ctcgcgggga  12780
gggcgggaag ggggccgggc gggagcccgc ggccaaccgt cgcccgtgac ggcaccgcc  12840 ccgcccccgt gacgcggtgc gggcgccggg gccgtggggc tgagcgctgc ggcggggccg  12900
ggccgggccg gggcgggagc tgagcgcggc gcggctgcgg gcggcgcccc ctccggtgca  12960
atatgttcaa gagaatggct gagttcgggc ctgactccgg gggcagggtg aaggtgcggc  13020
gcgggcggag ggacggggcg ggcgcggggc cgcccgcgg gtgccgggc ctctgccggc  13080 ccgcccggct cggcctgctg cggcgcttac gggcgcgctt ctcgccgctg ccgcttctct  13140 tctctccccgc gcaagggcgt caccatcgtg aagccggtag tgtacgggaa cgtgcgcgcg  13200
tacttcggga agaagaggga ggaggacggg cacacgcatc agtggacggt ttacgtgaag  13260
```

-continued

```
ccctacagga acgaggtagg gcccgagcgc gtcggccgcc gttctcggag cgccggagcc    13320
gtcagcgccg cgcctgggtg cgctgtggga cacagcgagc ttctctcgta ggacatgtcc    13380
gcctacgtga aaaaaatcca gttcaagctg cacgagagct acgggaatcc tctccgaggt    13440
gggtgttgcg tcgggggtt tgctccgctc ggtcccgctg aggctcgtcg ccctcatctt     13500
tctttcgtgc cgcagtcgtt accaaaccgc cgtacgagat caccgaaacg ggctggggcg    13560
aatttgaaat catcatcaag atattttca ttgatccaaa cgagcgaccc gtaagtacgc     13620
tcagcttctc gtagtgcttc ccccgtcctg gcggcccggg gctgggctgc tcgctgctgc    13680
cggtcacagt cccgccagcc gcggagctga ctgagctccc tttcccggga cgtgtgctct    13740
gtgttcggtc agcgaggcta tcgggagggc tttggctgca tttggcttct ctggcgctta    13800
gcgcaggagc acgttgtgct acgcctgaac tacagctgtg agaaggccgt ggaaaccgct    13860
ctcaaaactga tttattggcg aaatggctct aaactaaatc gtctcctctc tttggaaatg   13920
ctttagagaa ggtctctgtg gtagttctta tgcatctatc ctaaagcact tggccagaca    13980
atttaaagac atcaagcagc atttatagca ggcacgttta ataacgaata ctgaatttaa    14040
gtaactctgc tcacgttgta tgacgtttat tttcgtattc ctgaaagcca ttaaaatcct    14100
gtgcagttgt ttagtaagaa cagctgccac tgttttgtat ctaggagata actggtgttt    14160
ccctacagtt ctcaagctga taaaactctg tctttgtatc taggtaaccc tgtatcactt    14220
gctgaagctt tttcagtctg acaccaatgc aatcctggga agaaaactg tagtttctga    14280
attctatgat gaaatggtat gaaaatttta atgtcaaccg agcctgactt tatttaaaaa    14340
aaattattga tggtgctgtg tattttggtc cttccttaga tatttcaaga tcctactgcc    14400
atgatgcagc aactgctaac gacgtcccgt cagctgacac ttggtgctta caagcatgaa    14460
acagagtgta agtgcaaaat gaggatacct tcgccgaccg tcattcacta ctaatgtttt    14520
ctgtgggatg tgatcgtaca gtgagtttgg ctgtgtgaaa tttgaatagc ttggtattgg    14580
cagtgatgac gtgatcgatg ccttgcttat catgtttgaa atgaagtaga ataaatgcag    14640
cctgctttat ttgagatagt ttggttcatt ttatggaatg caagcaaaga ttatacttcc    14700
tcactgaatt gcactgtcca aaggtgtgaa atgtgtgggg atctggagga ccgtgaccga    14760
gggacattgg atcgctatct cccatttctt tgctgttac cagttcagat tttcttttca     14820
cctagtcttt aattcccagg gttttgtttt ttccttggtc atagttttg ttttcactc      14880
tggcaaatga tgttgtgaat tacactgctt cagcccacaaa actgatggac tgaatgaggt   14940
catcaaacaa acttttcttc ttccgtattt ccttttttt cccccactta tcatttttac     15000
tgctgttgtt gagtctgtaa ggctaaaagt aactgttttg tgcttttca ggacgtgtgc     15060
tttccaaatt actgccacat atataaagaa aggttggaat tttaaagata attcatgttt    15120
cttcttcttt tttgccacca cagttgcaga tcttgaagta aaaaccaggg aaaagctgga    15180
agctgccaaa aagaaaacca gttttgaaat tgctgagctt aaagaaaggt taaaagcaag    15240
tcgtgaaacc atcaactgct taagagtga atcagaaaa ctcgaagagg atgatcagtc      15300
taaagatatg tgatgagtgt tgacttggca gggagcctat aatgagaatg aaaggacttc    15360
agtcgtggag ttgtatgcgt tctctccaat tctgtaacgg agactgtatg aatttcattt    15420
gcaaatcact gcagtgtgtg acaactgact ttttataaat ggcagaaaac aagaatgaat    15480
gtatcctcat tttatagtta aaatctatgg gtatgtactg gtttatttca aggagaatgg    15540
atcgtagaga cttggaggcc agattgctgc ttgtattgac tgcatttgag tggtgtagga    15600
```

-continued

```
acatttgtc tatggtcccg tgttagttta cagaatgcca ctgttcactg ttttgttttg    15660 tatttactt tttctactgc aacgtcaagg ttttaaaagt tgaaaataaa acatgcaggt    15720
tttttttaaa tattttttg tctctatcca gtttgggctt caagtattat tgttaacagc    15780
aagtcctgat ttaagtcaga ggctgaagtg taatggtatt caagatgctt aagtctgttg    15840
tcagcaaaac aaaagagaaa acttcataaa atcaggaagt tggcatttct aataacttct    15900
ttatcaacag ataagagttt ctagccctgc atctactttc acttatgtag ttgatgcctt    15960
tatattttgt gtgtttggat gcaggaagtg attcctactc tgttatgtag atattctatt    16020
taacacttgt actctgctgt gcttagcctt tccccatgaa aattcagcgg ctgtaaatcc    16080
ccctcttctt ttgtagcctc atacagatgg cagaccctca ggcttataaa ggcttgggca    16140
tcttctttac tgctttgaga ttctgtgttg cagtaacctc tgccagagag gagaaaagcc    16200
ccacaaacct catccccttc ttctatagca atcagtatta ctaatgcttt gagaacagag    16260
cactggtttg aaacgtttga taattagcat ttaacatggc ttggtaaaga tgcagaactg    16320
aaacagctgt gacagtatga actcagtatg gagacttcat taagacaaac agctgttaaa    16380
atcaggcatg tttcattgag gaggacgggg caacttgcac cagtggtgcc cacacaaatc    16440
cttcctggcg ctgcagacca attttttctgg cattctgact gccgttgctg ctggtcacag    16500
agagcaacta tttttatcag ccacaggcaa tttgcttgta gtatttttcca agtgttgtag    16560 gtaagtataa atgcatcggc tccagagcac tttgagtata cttattaaaa acataaatga    16620
aagacaaatt agctttgctt gggtgcacag aacatttta gttccagcct gcttttttggt    16680 agaagccctc ttctgaggct agaactgact ttgacaagta gagaaactgg caacggagct    16740
attgctatcg aaggatcctt gttaacaaag ttaatcgtct tttaaggttt ggtttattca    16800
ttaaatttgc ttttaagctg tagctgaaaa agaacgtgct gtcttccatg caccaggtgg    16860
cagctctgtg caaagtgctc tctggtctca ccagcctttt aattgccggg attctggcac    16920
gtctgagagg gctcagactg gcttcgtttg tttgaacagc gtgtactgct ttctgtagac    16980
atggccggtt tctctcctgc agcttatgaa actgttcaca ctgaacacac tggaacaggt    17040
tgcccaagga ggccgtggat gccccatccc tggaggcatt caaggccagg ctggatgtgg    17100
ctctgggcag cctggtctgg tggttggcga tcctgcacat agcagcgggg ttgaaactcg    17160
atgatcactg tggtccttt caacccaggc tattctatga ttctatgatt caacagcaaa    17220
tcatatgtac tgagagagga acaaacaca agtgctactg tttgcaagtt ttgttcattt    17280
ggtaaaagag tcaggtttta aaattcaaaa tctgtctggt tttggtgttt ttttttttt    17340 atttattatt tctttggggt tcttttgat gctttatctt tctctgccag gactgtgtga    17400
caatgggaac gaaaagaac atgccaggca ctgtcctgga ttgcacacgc tggttgcact    17460
cagtagcagg ctcagaactg ccagtctttc cacagtatta cttctaaac ctaattttaa    17520 tagcgttagt agacttccat cactgggcag tgcttagtga atgctctgtg tgaacgtttt    17580
acttataagc atgttggaag ttttgatgtt cctggatgca gtagggaagg acagattagc    17640
tatgtgaaaa gtagattctg agtatcgggg ttacaaaaag tatagaaacg atgagaaatt    17700
cttgttgtaa ctaattggaa tttctttaag cgttcactta tgctacattc atagtatttc    17760
catttaaaag taggaaaagg taaaacgtga aatcgtgtga ttttcggatg gaacaccgcc    17820
ttcctatgca cctgaccaac ttccagagga aaagcctatt gaaagccgag attaagccac    17880
caaaagaact catttgcatt ggaatatgta gtatttgccc tcttcctccc gggtaattac    17940
tatactttat agggtgctta tatgttaaat gagtggctgg cactttttat tctcacagct    18000
```

```
                                        -continued gtggggaatt ctgtcctcta ggacagaaac aattttaatc tgttccactg gtgactgctt    18060
tgtcagcact tccacctgaa gagatcaata cactcttcaa tgtctagttc tgcaacactt    18120
ggcaaacctc acatcttatt tcatactctc ttcatgccta tgcttattaa agcaataatc    18180
tgggtaattt ttgttttaat cactgtcctg accccagtga tgaccgtgtc ccacctaaag    18240
ctcaattcag gtcctgaatc tcttcaactc tctatagcta acatgaagaa tcttcaaaag    18300
ttaggtctga gggacttaag gctaactgta gatgttgttg cctggtttct gtgctgaagg    18360
ccgtgtagta gttagagcat tcaacctcta g                                   18391
```

RECOMBINANT PROMOTERS IN AVIAN CELLS

This application is a continuation-in-part of U.S. patent application Ser. No. 09/922,549, filed Aug. 3, 2001 now U.S. Pat. No. 7,176,300, which claims the benefit of provisional application Ser. No. 60/280,004, filed Mar. 30, 2001. This application also claims the benefit from provisional application Ser. No. 60/351,550, filed Jan. 25, 2002.

FIELD OF THE INVENTION

The present invention relates generally to the identification of an avian lysozyme gene expression control region, specifically from the chicken. More specifically, the invention relates to recombinant nucleic acids and expression vectors, transfected cells and transgenic animals, especially chickens, that comprise the avian lysozyme gene expression control region operably linked to a polypeptide-encoding nucleic acid and, optionally, a chicken lysozyme 3' domain. The present invention further relates to the expression of the polypeptide-encoding nucleic acid under the control of the isolated avian lysozyme gene expression control region.

BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology to convert animals into "protein factories" for the production of specific proteins or other substances of pharmaceutical interest (Gordon et al., 1987, *Biotechnology* 5: 1183–1187; Wilmut et al., 1990, *Theriogenology* 33: 113–123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., in U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct, which is lined with tubular gland cells. These cells secrete the egg-white proteins, including ovalbumin, lysozyme, ovomucoid, conalbumin and ovomucin, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. As a result, efforts have been made to create transgenic chickens expressing heterologous proteins in the oviduct by means of microinjection of DNA (PCT Publication WO 97/47739).

The chicken lysozyme gene is highly expressed in the myeloid lineage of hematopoietic cells, and in the tubular glands of the mature hen oviduct (Hauser et al., 1981, *Hematol. and Blood Transfusion* 26: 175–178; Schutz et al., 1978, Cold Spring Harbor Symp. Quart. Biol. 42: 617–624) and is therefore a suitable candidate for an efficient promoter for heterologous protein production in transgenic animals. The regulatory region of the lysozyme locus extends over at least 12 kb of DNA 5' upstream of the transcription start site, and comprises a number of elements that have been individually isolated and characterized. The known elements include three enhancer sequences at about −6.1 kb, −3.9 kb, and −2.7 kb (Grewal et al., 1992, *Mol. Cell Biol.* 12: 2339–2350; Banifer et al., 1996, *J. Mol. Med.* 74: 663–671), a hormone responsive element (Hecht et al., 1988, *E.M.B.O. J.* 7: 2063–2073), a silencer element and a complex proximal promoter. The constituent elements of the lysozyme gene expression control region are identifiable as DNAase 1 hypersensitive chromatin sites (DHS). They may be differentially exposed to nuclease digestion depending upon the differentiation stage of the cell. For example, in the multipotent progenitor stage of myelomoncytic cell development, or in erythroblasts, the silencer element is a DHS. At the myeloblast stage, a transcription enchancer located −6.1 kb upstream from the gene transcription start site is a DHS, while at the later monocytic stage another enhancer, at −2.7 kb becomes DNAase sensitive (Huber et al., 1995, *DNA and Cell Biol.* 14: 397–402).

Scattered throughout the chicken genome, including the chicken lysozyme locus, are short stretches of nucleic acid that resemble features of Long Terminal Repeats (LTRs) of retrovirus. The function of these elements is unclear but most likely help define the DHS regions of a gene locus (Stein et al., 1983, *Proc. Natl. Acad. Sci. U.S.A.* 80: 6485–6489).

Flanking the lysozyme gene, including the regulatory region, are matrix attachment regions (5' MAR & 3' MAR), alternatively referred to as "scaffold attachment regions" or SARs. The outer boundaries of the chicken lysozyme locus have been defined by the MARs (Phi-Van et al., 1988, *E.M.B.O. J.* 7: 655–664; Phi-Van, L. and Stratling, W. H., 1996, *Biochem.* 35: 10735–10742). Deletion of a 1.32 kb or a 1.45 kb halves region, each comprising half of a 5 MAR, reduces positional variation in the level of transgene expression (Phi-Van and Stratling, supra).

The 5' matrix-associated region (5' MAR), located about −11.7 kb upstream of the chicken lysozyme transcription start site, can increase the level of gene expression by limiting the positional effects exerted against a transgene (Phi-Van et al., 1988, supra). At least one other MAR is located 3' downstream of the protein encoding region. Although MAR nucleic acid sequences are conserved, little cross-hybridization is seen, indicating significant overall sequence variation. However, MARs of different species can interact with the nucleomatrices of heterologous species, to the extent that the chicken lysozyme MAR can associate with the plant tobacco nucleomatrix as well as that of the chicken oviduct cells (Mlynarona et al., 1994, *Cell* 6: 417–426; von Kries et al., 1990, *Nucleic Acids Res.* 18: 3881–3885).

Gene expression must be considered not only from the perspective of cis-regulatory elements associated with a gene, and their interactions with trans-acting elements, but also with regard to the genetic environment in which they are located. Chromosomal positioning effects (CPEs), therefore, are the variations in levels of transgene expression associated with different locations of the transgene within the recipient genome. An important factor governing CPE upon the level of transgene expression is the chromatin structure around a transgene, and how it cooperates with the cis-regulatory elements. The cis-elements of the lysozyme locus are confined within a single chromatin domain (Banifer et al., 1996, supra; Sippel et al., pgs. 133–147 in Eckstein F. & Lilley D. M. J. (eds), "Nucleic Acids and Molecular Biology", Vol. 3, 1989, Springer.

Deletion of a cis-regulatory element from a transgenic lysozyme locus is sufficient to reduce or eliminate positional independence of the level of gene expression (Banifer et al., 1996, supra). There is also evidence indicating that positional independence conferred on a transgene requires the cotransfer of many kilobases of DNA other than just the protein encoding region and the immediate cis-regulatory elements.

The lysozyme promoter region of chicken is active when transfected into mouse fibroblast cells and linked to a reporter gene such as the bacterial chloramphenicol acetyltransferase (CAT) gene. The promoter element is also effective when transiently transfected into chicken promacrophage cells. In each case, however, the presence of a 5' MAR element increased positional independency of the level of transcription (Stief et al., 1989, *Nature* 341: 343–345; Sippel et al., pgs. 257–265 in Houdeline L. M. (ed), "Transgenic Animals: Generation and Use").

The ability to direct the insertion of a transgene into a site in the genome of an animal where the positional effect is limited offers predictability of results during the development of a desired transgenic animal, and increased yields of the expressed product. Sippel and Steif disclose, in U.S. Pat. No. 5,731,178, methods to increase the expression of genes introduced into eukaryotic cells by flanking a transcription unit with scaffold attachment elements, in particular the 5' MAR isolated from the chicken lysozyme gene. The transcription unit disclosed by Sippel and Steif was an artificial construct that combined only the −6.1 kb enhancer element and the proximal promoter element (base position −579 to +15) from the lysozyme gene. Other promoter associated elements were not included. However, although individual cis-regulatory elements have been isolated and sequenced, together with short regions flanking DNA, the entire nucleic acid sequence comprising the functional 5' upstream region of the lysozyme gene has not been determined in its entirety and therefore not employed as a functional promoter to allow expression of a heterologous transgene.

What is still needed, however, is an efficient transcription promoter that will allow expression of a transgene in avian cells that is not subject to positional variation.

What is also needed is a gene expression promoter cassette that will allow expression of a transgene in the oviduct cells of an avian and efficient gene expression regardless of the chromosomal location of the expression system.

SUMMARY OF THE INVENTION

Briefly described, the present invention relates to a novel isolated avian nucleic acid comprising an avian lysozyme gene expression control region.

The isolated nucleic acid of the present invention is useful for reducing the chromosomal positional effect of a transgene operably linked to the lysozyme gene expression control region and transfected into a recipient cell. By isolating a region of the avian genome extending from 5' upstream of a 5' MAR of the lysozyme locus to the junction between the signal peptide sequence and a polypeptide-encoding region, cis-elements are also included to allow gene expression in a tissue-specific manner. The lysozyme promoter region of the present invention, therefore, will allow expression of an operably linked heterologous nucleic acid insert in a transfected avian cell such as, for example, an oviduct cell.

One aspect of the present invention provides a novel isolated nucleic acid that is located immediately 5' upstream of the native lysozyme-encoding region of the chicken lysozyme gene locus. The novel isolated avian nucleic acid sequence encoding a lysozyme gene expression control region comprises at least one 5' matrix attachment region, an intrinsically curved DNA region, at least one transcription enhancer element, a negative regulatory element, at least one hormone responsive element, at least one avian CR1 repeat element, and a proximal lysozyme promoter and signal peptide-encoding region. Interspersed between these constituent elements are stretches of nucleic acid that serve at least to organize the above elements in an ordered array relative to a polypeptide-encoding region.

In one embodiment of the present invention the isolated nucleic acid is isolated from a chicken.

The isolated avian lysozyme of the present invention may be operably linked with a selected nucleic acid insert, wherein the nucleic acid insert encodes a polypeptide desired to be expressed in a transfected cell. The nucleic acid insert may be placed in frame with a signal peptide sequence. Translation initiation may start with the signal peptide and continue through the nucleic acid insert, thereby producing an expressed polypeptide having the desired amino acid sequence.

The sequence of the expressed nucleic acid insert may be optimized for codon usage by a host cell. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken.

The recombinant DNA of the present invention may further comprise a polyadenylation signal sequence that will allow the transcript directed by the novel lysozyme gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like.

The recombinant DNA of the present invention may also further comprise the chicken lysozyme 3' domain operably linked to the nucleic acid insert encoding a polypeptide. The 3' domain may include a 3' untranslated region, a polyadenylation signal and a 3' MAR that may reduce positional variation in transgenic avians.

Yet another aspect of the present invention are expression vectors suitable for delivery to a recipient cell for expression of the vector therein. The expression vector of the present invention may comprise an isolated avian lysozyme gene expression control region operably linked to a nucleic acid insert encoding a polypeptide, and optionally a polyadenylation signal sequence. The expression vector may further comprise a bacterial plasmid sequence, a viral nucleic acid sequence, or fragments or variants thereof that may allow for replication of the vector in a suitable host.

Another aspect of the present invention is a method of expressing a heterologous polypeptide in a eukaryotic cell by transfecting the cell with a recombinant DNA comprising an avian lysozyme gene expression control region operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

Also within the scope of the present invention are recombinant cells, tissues and animals containing non-naturally occurring recombinant nucleic acid molecules according to the present invention and described above. In one embodiment of the present invention, the transformed cell is a chicken oviduct cell and the nucleic acid insert comprises the chicken lysozyme gene expression control region, a nucleic acid insert encoding a human interferon α2b and codon optimized for expression in an avian cell, and an SV40 polyadenylation sequence.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 1a, FIG. 1b, FIG. 1c, and FIG. 1d illustrate the primers (SEQ ID NOS: 1–64) used in the sequencing of the lysozyme gene expression controlling region (SEQ ID NO: 67).

FIG. 3a, FIG. 3b, FIG. 3c and FIG. 3d illustrate the nucleic acid sequence (SEQ ID NO: 65) comprising the chicken lysozyme gene expression controlling region (SEQ ID NO: 67), the nucleic acid sequence SEQ ID NO: 66 encoding the chicken expression optimized human interferon α2b (IFNMAGMAX) which is underlined in the figures and the SV40 polyadenylation signal sequence (SEQ ID NO: 68) which is in bold print in the figures.

FIG. 4 illustrates the nucleic acid sequence SEQ ID NO: 66 encoding the chicken expression optimized human interferon α2b (IFNMAGMAX).

FIG. 5a, 5b, 5c and 5d illustrate the nucleic acid sequence SEQ ID NO: 67 encoding the chicken lysozyme gene expression controlling region.

FIG. 6 illustrates the nucleic acid sequence SEQ ID NO: 68 encoding the SV40 polyadenylation signal sequence.

FIG. 7a, 7b, and 7c illustrate a portion of the nucleic acid sequence SEQ ID NO: 69 encoding the chicken lysozyme 3' domain.

FIG. 8a, FIG. 8b, FIG. 8c, FIG. 8d, FIG. 8e, FIG. 8f, FIG. 8g, FIG. 8h, FIG. 8i and 8j illustrate the nucleic acid sequence of SEQ ID NO: 74 encoding the lysozyme gene expression controlling region shown in SEQ ID NO: 67 linked to the nucleic acid insert encoding the chicken expression-optimized human interferon α2b (IFNMAGMAX) (SEQ ID NO: 66) which is underlined in the figure and is in turn linked to the chicken lysozyme 3' domain (SEQ ID NO: 69) which is shown in bold print. A fragment of a pBluescript cloning vector approximately 44 nucleotides in length is present between the IFNMAGMAX and the lysozyme 3' domain and is shown in lower case (FIG. 8f). The nucleotide sequence shown in lower case 3' of the chicken lysozyme 3' domain is nucleotide sequence from the cloning vectors pPolyIII and pBluescript (see, FIG. 8i to 8j).

DETAILED DESCRIPTION OF THE PREFERRED EMBODIMENTS

Figure 2:
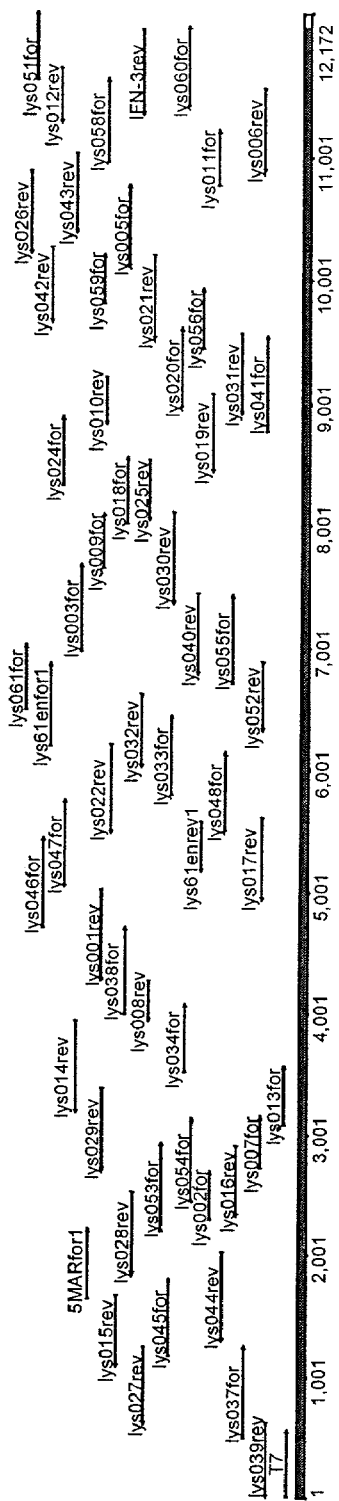
FIG. 2 schematically illustrates the approximately 12 kb lysozyme gene expression controlling region (SEQ ID NO: 67), indicating the relative positions and orientations of the primers (SEQ ID NOS: 1–64) used in the sequencing thereof.
Figure 9:
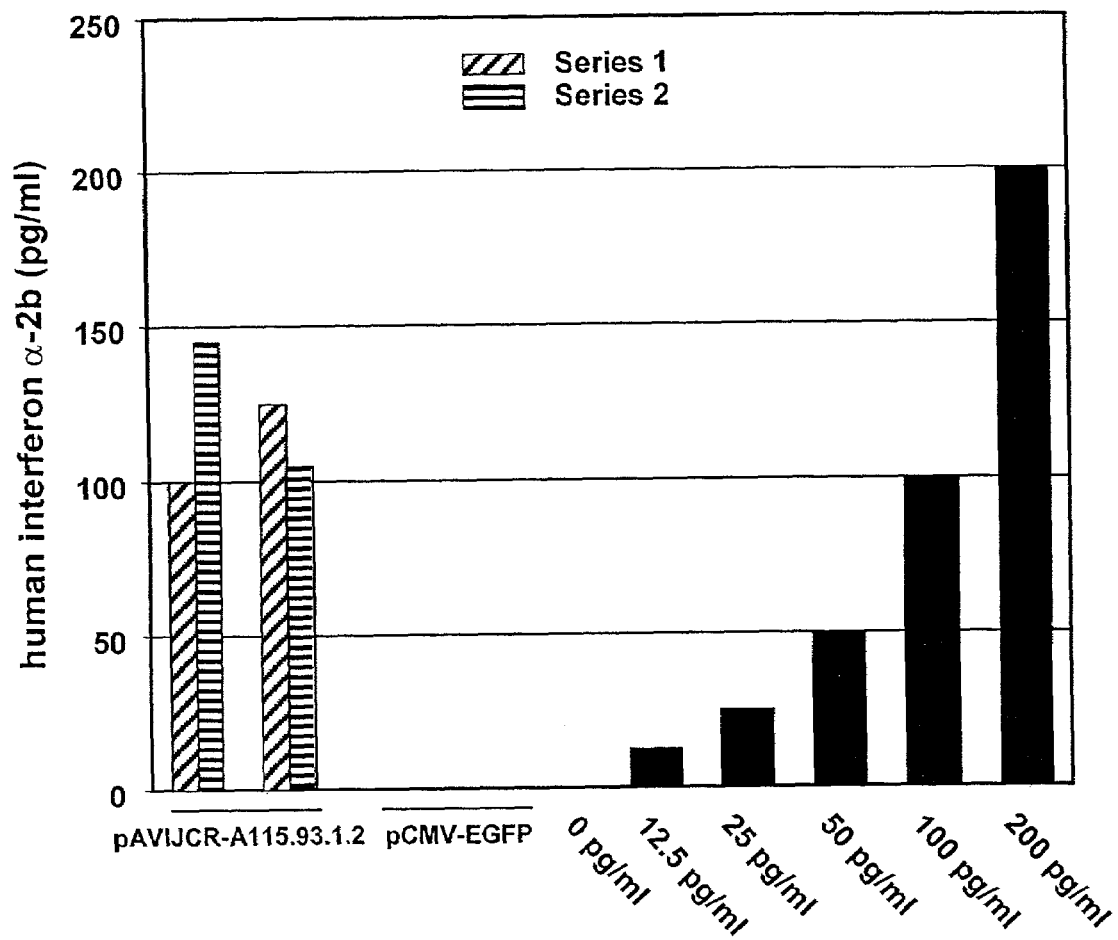
FIG. 9 illustrates the yield of the human interferon α2b, optimized for chicken expression (IFNMAGMAX), in transfected quail oviduct cultured cells.

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

This description uses gene nomenclature accepted by the Cucurbit Genetics Cooperative as it appears in the *Cucurbit Genetics Cooperative Report* 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

For convenience, certain terms employed in the specification, examples, and appended claims are collected here.

Definitions

The term "animal" is used herein to include all vertebrate animals, including avians and humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes a lysozyme gene expression control region or a variant thereof of the present invention.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term "significant" as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The terms "matrix attachment regions" or "SAR elements" as used herein refer to DNA sequences having an affinity or intrinsic binding ability for the nuclear scaffold or matrix. The MAR elements of the chicken lysozyme locus were described by Phi-Van et al., 1988, *E.M.B.O. J.* 76: 665–664 and Phi-Van L. and Stratling, W. H., 1996, Biochem. 35: 10735–10742, the contents of which are incorporated herein by reference in their entireties.

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a lysozyme gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g., low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al., 1984, *Anal. Biochem.* 138: 267–284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. 1989, "Molecular Cloning: A Laboratory Manual", 2nd ed., Cold Spring Harbor Press, the contents of which are herein incorporated by reference in its entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino avid sequences as determined using the algorithm of Karlin and Attschul, 1990, *Proc. Natl. Acad Sci.* 87: 2264–2268, modified as in Karlin and Attschul, 1993, *Proc. Natl. Acad. Sci.* 90: 5873–5877. Such an algorithm is incorporated into the NBLAST and XBLAST programs of Attschul et al., 1990, *T. Mol. Biol.* Q15: 403–410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al., 1997, *Nucl. Acids Res.* 25: 3389–3402. When utilizing BLAST and Gapped BLAST programs, the default parameters of the respective programs (e.g. XBLAST and NBLAST) are used. See www.ncbi.nlm.nih.gov. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises the lysozyme gene expression control region operably linked to a nucleotide sequence coding at least one polypeptide. As used herein, the term "regulatory sequences" includes promoters, enhancers, and other elements that may control gene expression. Standard molecular biology textbooks such as Sambrook et al. eds., 1989, "Molecular Cloning: A Laboratory Manual", 2nd ed., Cold Spring Harbor Press may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell, and more preferably a chicken male germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to the male germ cells using specific ligands that are recognized by receptors on the cell surface of the germ cell, such as the c-kit ligand or modifications thereof.

Other preferred transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

Pharmaceutical compositions comprising agents that will modulate the regulation of the expression of a polypeptide-encoding nucleic acid operably linked to a lysozyme gene expression control region can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Pharmaceutical compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Science", 17th edition, 1985 may be consulted to prepare suitable preparations, without undue experimentation. Dosages can generally range from a few hundred milligrams to a few grams.

As used herein, a "transgenic animal" is any animal, such as an avian species, including the chicken, in which one or more of the cells of the avian may contain heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide, e.g., either agonistic or antagonistic forms, or in which the gene has been disrupted. The terms "chimeric animal" or "mosaic animal" are used herein to refer to animals in which the recombinant gene is found, or in which the recombinant is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention will include one or more transcriptional regulatory sequences, polyadenylation signal sequences and any other nucleic acid, such as introns, that may be necessary for optimal expression of a selected nucleic acid.

The term "chromosomal positional effect (CPE)" as used herein refers to the variation in the degree of gene transcription as a function of the location of the transcribed locus within the cell genome. Random transgenesis may result in a transgene being inserted at different locations in the genome so that individual cells of a population of transgenic cells may each have at least one transgene, each at a different location and therefore each in a different genetic environment. Each cell, therefore, may express the transgene at a level specific for that particular cell and dependent upon the immediate genetic environment of the transgene. In a transgenic animal, as a consequence, different tissues may exhibit different levels of transgene expression.

Techniques useful for isolating and characterizing the nucleic acids and proteins of the present invention are well known to those of skill in the art and standard molecular biology and biochemical manuals may be consulted to select suitable protocols without undue experimentation. See, for example, Sambrook et al, 1989, "Molecular Cloning: A Laboratory Manual", 2nd ed., Cold Spring Harbor, the content of which is herein incorporated by reference in its entirety.

Abbreviations:

Abbreviations used in the present specification include the following: aa, amino acid(s); bp, base pair(s); cDNA, DNA complementary to RNA; nt, nucleotide(s); SSC, sodium chloride-sodium citrate; DMSO, dimethyl sulfoxide; MAR; matrix attachment region.

Chicken lysozyme gene expression control region nucleic acid sequences: A series of PCR amplifications of template chicken genomic DNA were used to isolate the gene expression control region of the chicken lysozyme locus. Two amplification reactions used the PCR primer sets SEQ ID NOS: 1 and 2 and SEQ ID NOS: 3 and 4. The amplified PCR products were united as a contiguous isolated nucleic acid by a third PCR amplification step with the primers SEQ ID NOS: 1 and 4, as described in Example 1 below.

The isolated PCR-amplified product, comprising about 12 kb of the nucleic acid region 5' upstream of the native chicken lysozyme gene locus, was cloned into the plasmid pCMV-LysSPIFNMM. pCMV-LysSPIFNMM comprises a modified nucleic acid insert encoding a human interferon α2b sequence and an SV40 polyadenylation signal sequence 3' downstream of the interferon encoding nucleic acid. The sequence SEQ ID NO: 66 of the nucleic acid insert encoding human interferon α2b was in accordance with avian cell codon usage, as determined from the nucleotide sequences encoding chicken ovomucin, ovalbumin, ovotransferrin and lysozyme. The novel chicken lysozyme gene expression control region, interferon-encoding insert and the SV40 polyadenylation signal sequence of the resulting plasmid construct pAVIJCR-A115.93.1.2, constructed as described in Example 1 below, was sequenced using the artificial oligonucleotide primers SEQ ID NOS: 1–64, as illustrated in FIGS. 1 and 2.

The nucleic acid sequence (SEQ ID NO: 65) (GenBank Accession No. AF405538) of the insert in pAVIJCR-A115.93.1.2 is shown in FIG. 3, with the modified human interferon α2b encoding nucleotide sequence SEQ ID NO: 66 (GenBank Accession No. AF405539) and the novel chicken lysozyme gene expression control region SEQ ID NO: 67 (GenBank Accession No. AF405540) shown in FIGS. 4 and 5 respectively. A polyadenylation signal sequence that is suitable for operably linking to the polypeptide-encoding nucleic acid insert is the SV40 signal sequence SEQ ID NO: 68, as shown in FIG. 6.

The plasmid pAVIJCR-A115.93.1.2 was restriction digested with enzyme FseI to isolate a 15.4 kb DNA containing the lysozyme 5' matrix attachment region (MAR) and the −12.0 kb lysozyme promotor during the expression of the interferon-encoding insert, as described in Example 2, below. Plasmid pIIIilys was restriction digested with MluI and XhoI to isolate an approximately 6 kb nucleic acids, comprising the 3' lysozyme domain, the sequence of which (SEQ ID NO: 70) is shown in FIG. 7. The 15.4 kb and 6 kb nucleic acids were ligated and the 21.4 kb nucleic acid comprising the nucleic acid sequence SEQ ID NO: 70 (GenBank Assession No.AF 497473) as shown in FIG. 8 was transformed into recipient STBL4 cells as described in Example 2, below.

The inclusion of the novel isolated avian lysozyme gene expression control region of the present invention upstream of a codon-optimized interferon-encoding sequence in pAVIJCR-A115.93.1.2 allowed expression of the interferon polypeptide in transfected avian cells, as described in Example 5, below. The 3' lysozyme domain SEQ ID NO: 69, when operably linked downstream of the heterologous nucleic acid insert, also allows expression of the nucleic acid insert as described in Example 7, below. For example, the nucleic acid insert may encode a heterologous polypeptide such as the α2b interferon having sequence SEQ ID NO: 66.

It is further contemplated that any nucleic acid sequence encoding a polypeptide may be operably linked to the novel isolated avian lysozyme gene expression control region and optionally operably linked to the 3' lysozyme domain SEQ ID NO. 69 so as to be expressed in a transfected avian cell. The plasmid construct pAVIJCR-A115.93.1.2 was transfected into cultured quail oviduct cells, which were then incubated for about 72 hours. ELISA assays of the cultured media showed that the transfected cells synthesized a polypeptide detectable with anti-human interferon α2b antibodies. Plasmid construct pAVIJCR-A212.89.2.1 and pAVIJCR-A212.89.2.3 transfected into chicken myelomonocytic HD11 cells yield detectable human α2b interferon, as described in Example 9 and shown in FIG. 10, below.

The novel isolated chicken lysozyme gene expression control region of the present invention comprises the nucleotide elements that are positioned 5' upstream of the lysozyme-encoding region of the native chicken lysozyme locus and which are necessary for the regulated expression of a downstream polypeptide-encoding nucleic acid. While not wishing to be bound by any one theory, the inclusion of at least one 5' MAR element in the isolated control region may confer positional independence to a transfected gene operably linked to the novel lysozyme gene expression control region.

The isolated lysozyme gene expression control region of the present invention is useful for reducing the chromosomal positional effect of a transgene operably linked to the lysozyme gene expression control region and transfected into a recipient avian cell. By isolating a region of the avian genome extending from a point 5' upstream of a 5' MAR of the lysozyme locus to the junction between the signal peptide sequence and a polypeptide-encoding region, cis-regulatory elements are also included that may allow gene expression in a tissue-specific manner. The lysozyme promoter region of the present invention, therefore, will allow expression of an operably linked heterologous nucleic acid insert in a transfected avian cell such as, for example, an oviduct cell.

It is further contemplated that a recombinant DNA of the present invention may further comprise the chicken lysozyme 3' domain (SEQ. ID NO: 69) linked downstream of the nucleic acid insert encoding a heterologous polypeptide. The lysozyme 3' domain includes a nucleic acid sequence encoding a 3' MAR domain that may cooperate with a 5' MAR to direct the insertion of the construct of the present invention into the chromosome of a transgenic avian, or may act independently of the 5' MAR.

One aspect of the present invention, therefore, provides a novel isolated nucleic acid that comprises the nucleotide sequence SEQ ID NO: 67, shown in FIG. 5 and derivatives and variants thereof, that is located immediately 5' upstream of the native lysozyme-encoding region of the chicken lysozyme gene locus.

In one embodiment of the novel isolated nucleic acid of the present invention, therefore, the avian nucleic acid sequence encoding a lysozyme gene expression control region comprises at least one 5' matrix attachment region, an intrinsically curved DNA region, at least one transcription enhancer element, a negative regulatory element, at least one hormone responsive element, at least one avian CR1 repeat element, and a proximal lysozyme promoter and signal peptide-encoding region. Interspersed between these constituent elements are stretches of nucleic acid that serve at least to organize the above elements in an ordered array relative to a polypeptide-encoding region, such as that encoding for chicken lysozyme. It is contemplated to be within the scope of the present invention that the cis-elements of the lysozyme gene expression control region may be in any linear arrangement that can allow the formation of a transcript comprising the nucleotide sequence or its complement of a nucleic insert operably linked to the lysozyme gene expression control region.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 67, as shown in FIG. 5, or a variant thereof.

Another aspect of the present invention provides a novel isolated nucleic avid that comprises the nucleic acid SEQ ID NO: 69 encoding the chicken 3' lysozyme domain operably liked to the nucleic acid having sequence SEQ ID NO: 65.

One embodiment of the isolated nucleic acid of the present invention, therefore, is a lysozyme gene expression control region comprising the nucleic acid sequence SEQ ID NO. 66 operably linked to a nucleic acid for expression in avian cells, and a chicken 3' lysozyme domain having the nucleic acid SEQ ID NO: 70, as shown in FIG. 8.

In another embodiment of the isolated nucleic avid of the present invention, the nucleic acid for expression in avian cells encodes a human interferon α2b protein optimized for expression in avian cells.

Another aspect of the invention provides nucleic acids that can hybridize under high, medium or low stringency conditions to an isolated nucleic acid that encodes a chicken lysozyme gene expression control region having all, a derivative of, or a portion of the nucleic acid sequence SEQ ID NO: 67 shown in FIG. 5. The nucleotide sequence determined from the isolation of the lysozyme gene expression control region from a chicken (SEQ ID NO: 67) will allow for the generation of probes designed for use in identifying homologs of lysozyme gene expression control regions in other avian species.

Fragments of a nucleic acid encoding a portion of the subject lysozyme gene expression control region are also within the scope of the invention. As used herein, a fragment of the nucleic acid encoding an active portion of a lysozyme gene expression control region refers to a nucleotide sequence having fewer nucleotides than the nucleotide sequence encoding the entire nucleic acid sequence of the lysozyme gene expression control region.

In one embodiment of the present invention, the nucleotide sequence of the isolated DNA molecule of the present invention may be used as a probe in nucleic acid hybridization assays for the detection of the lysozyme gene expression control region. The nucleotide sequence of the present invention may be used in any nucleic acid hybridization assay system known in the art, including, but not limited to, Southern blots (Southern, E. M., 1975, *J. Mol. Biol.* 98: 508), Northern blots (Thomas et al., 1980, *Proc. Natl. Acad. Sci.* 77: 5201–05), and Colony blots (Grunstein et al., 1975, *Proc. Natl. Acad. Sci.* 72: 3961–65)(the contents of which are hereby incorporated by reference in their entireties). Alternatively, the isolated DNA molecules of the present invention can be used in a gene amplification detection procedure such as a polymerase chain reaction (Erlich et al., 1991, *Science* 252: 1643–51, the content of which is hereby incorporated by reference in its entirety) or in restriction fragment length polymorphism (RFLP) diagnostic techniques, as described in pgs. 519–522 and 545–547 of Watson et al., 2nd ed., 1992, "Recombinant DNA", Scientific American Books (the contents of which is hereby incorporated by reference in its entirety).

Nucleotides constructed in accordance with the present invention can be labeled to provide a signal as a means of detection. For example, radioactive elements such as $^{32}$P, $^{3}$H, and $^{35}$S or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals, such as *Promega: Protocol and Applications Guide,* 2nd Edition, 1991 (Promega Corp., Madison, Wis., the content of which is incorporated herein in its entirety), may be consulted to select an appropriate labeling protocol without undue experimentation.

In another embodiment of the present invention, an isolated nucleic acid molecule of the present invention includes a nucleic acid that is at least about 75%, preferably at least about 80%, more preferably at least about 85%, even more preferably at least about 90%, still more preferably at least about 95%, and even more preferably at least about 99%, identical to a chicken-derived lysozyme gene expression control region-encoding nucleic acid molecule as depicted in SEQ ID NO: 67.

In another embodiment of the present invention, an avian lysozyme gene expression control region gene or nucleic acid molecule can be an allelic variant of SEQ ID NO: 67.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken lysozyme gene expression control region nucleic acid molecule (SEQ ID NO: 67) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain lysozyme gene expression control region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian lysozyme gene expression control region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to chicken lysozyme gene expression control region include, but are not limited to, GenBank and the mammalian Gene Index database of The Institute of Genomics Research (TIGR).

Codon-optimized Proteins

Another aspect of the present invention is a recombinant DNA molecule comprising the novel isolated avian lysozyme gene expression control region of the present invention operably linked to a selected polypeptide-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed polypeptide having the desired amino acid sequence.

It is anticipated that the recombinant DNA, therefore, may further comprise a polyadenylation signal sequence that will allow the transcript directed by the novel lysozyme gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof.

In one embodiment of the recombinant DNA of the present invention, the polyadenylation signal sequence is derived from the SV40 virus.

In another embodiment of the recombinant DNA of the present invention, the polyadenylation signal has the nucleic acid sequence SEQ ID NO: 68 or a variant thereof, as shown in FIG. 6.

It is further anticipated that the recombinant DNA of the present invention may further comprise the chicken lysozyme 3' domain SEQ ID NO: 69, or a variant thereof. The lysozyme 3' domain comprises a 3' untranslated region, a polyadenylation sequence and at least on 3' MAR.

Another aspect of the present invention is to provide nucleic acid sequences of a human interferon α2b protein optimized for expression in avian cells, and derivatives and fragments thereof.

In derivatives of the human interferon α2b protein of the present invention, for example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, "Biochemistry", 2nd ed, L. Stryer, ed., W H Freeman and Co., 1981). Peptides in which more than one replacement has taken place can readily be tested in the same manner.

One embodiment of the present invention is a recombinant DNA molecule comprising the isolated avian lysozyme gene expression control region of the present invention, operably linked to a nucleic acid insert encoding a polypeptide, and a polyadenylation signal sequence optionally operably linked thereto. It is contemplated that when the recombinant DNA is to be delivered to a recipient cell for expression therein, the sequence of the nucleic acid sequence may be modified so that the codons are optimized for the codon usage of the recipient species. For example, if the recombinant DNA is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken.

In one embodiment of the recombinant DNA of the present invention, therefore, the nucleic acid insert encodes the human interferon α2b polypeptide. Optimization of the sequence for codon usage elevates the level of translation in avian eggs. In this embodiment, the sequence (SEQ ID NO: 66) of the optimized human interferon sequence is shown in FIG. 4.

In yet another embodiment of the present invention, the recombinant DNA comprises the isolated avian lysozyme gene expression control region operably linked to a nucleic acid encoding a human interferon α2b and the SV40 polyadenylation sequence, the recombinant DNA having the nucleotide sequence SEQ ID NO: 65, as shown in FIG. 3, or a variant thereof.

In still another embodiment of the present invention, the recombinant DNA comprises the isolated avian lysozyme gene expression control region operably linked to the nucleic acid encoding a polypeptide, and the chicken lysozyme 3' domain SEQ ID NO: 69. In one embodiment of the present invention, the nucleic acid insert is SEQ ID NO: 66 encoding a human α2b interferon, and the recombinant DNA construct has the nucleic acid sequence SEQ ID NO: 70.

The protein of the present invention may be produced in purified form by any known conventional techniques. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

Recombinant Nucleic Acids, and Expression Thereof Under the Control of an Avian Lysozyme Promoter:

Another potentially useful application of the novel isolated lysozyme gene expression control region of the present invention is the possibility of increasing the amount of a heterologous protein present in a bird, (especially the chicken) by gene transfer. In most instances, a heterologous polypeptide-encoding nucleic acid insert transferred into the recipient animal host will operably linked with the lysozyme gene expression control region, to allow the cell to initiate and continue production of the genetic product protein. A recombinant DNA molecule of the present invention can be transferred into the extra-chromosomal or genomic DNA of the host.

The recombinant DNA nucleic acid molecules of the present invention can be delivered to cells using conventional recombinant DNA technology. The recombinant DNA molecule may be inserted into a cell to which the recombinant DNA molecule is heterologous (i.e. not normally present). Alternatively, as described more fully below, the recombinant DNA molecule may be introduced into cells which normally contain the recombinant DNA molecule, for example, to correct a deficiency in the expression of a polypeptide, or where over-expression of the polypeptide is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated lysozyme gene expression control region.

U.S. Pat. No. 4,237,224 to Cohen and Boyer, hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for expression of the vector therein. It is contemplated to be within the scope of the present invention for the expression vector to comprise an isolated avian lysozyme gene expression control region operably linked to a nucleic acid insert encoding a polypeptide, and optionally a polyadenylation signal sequence. The expression vector of the present invention may further comprise a bacterial plasmid sequence, a viral nucleic acid sequence, or fragments or variants thereof that may allow for replication of the vector in a suitable host.

The novel isolated avian lysozyme gene expression control region of the present invention (SEQ ID NO: 67) and a polypeptide-encoding nucleic acid sequence operably linked thereto, such as, for example, SEQ ID NO: 66 or a derivative or truncated variant thereof, and optionally a polyadenylation signal sequence such as, for example, SEQ ID NO: 68 or the chicken lysozyme 3' domain may be introduced into viruses such as vaccinia virus. Methods for making a viral recombinant vector useful for expressing a protein under the control of the lysozyme promoter are analogous to the methods disclosed in U.S. Pat. Nos. 4,603,112; 4,769,330; 5,174,993; 5,505,941; 5,338,683; 5,494,807; 4,722,848; Paoletti E., 1996, *Proc. Natl. Acad. Sci.,* 93: 11349–11353; Moss, B., 1996, *Proc. Natl. Acad. Sci.* 93: 11341–11348; Roizman 1996, *Proc. Natl. Acad. Sci.* 93: 11307–11302; Frolov et al., 1996, *Proc. Natl. Acad. Sci.* 93: 11371–11377; Grunhaus et al., 1993, *Seminars in Virology* 3: 237–252 and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier, F. W. et. al., 1990, *Use of T7 RNA Polymerase to Direct Expression of Cloned Genes* in "Gene Expression Technology," vol. 185, which is hereby incorporated by reference in its entirety) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., 1982, *Molecular Cloning: A Laboratory Manual,* Cold Springs Laboratory, Cold Springs Harbor, N.Y., which is hereby incorporated by reference in its entirety.

A variety of host-vector systems may be utilized to express the protein-encoding sequence(s). Primarily, the vector system must be compatible with the host cell used. The use of eukaryotic recipient host cells permits partial or complete post-translational modification such as, but not only, glycosylation and/or the formation of the relevant inter- or intra-chain disulfide bonds. Host-vector systems include but are not limited to the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, etc.); insect cell systems infected with virus (e.g., baculovirus) or avian embryonic cells inoculated with the recombinant nucleic acid. The expression elements of these vectors vary in their strength and specificities. Depending upon the host-vector system utilized, any one of a number of suitable transcription and translation elements can be used.

Once the novel isolated lysozyme gene expression control region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection and the like.

Another aspect of the present invention, therefore, is a method of expressing a heterologous polypeptide in a eukaryotic cell by transfecting the cell with a recombinant DNA comprising an avian lysozyme gene expression control region operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken lysozyme gene expression control region, a nucleic acid insert encoding a human interferon α2b and codon optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian lysozyme gene expression control region according to the present invention is produced in the white of an egg.

Viral Vector Cell Transformation:

An exemplary approach for the in vivo introduction of a nucleic acid encoding the subject novel isolated lysozyme gene expression control region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo. These vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid encoding a lysozyme gene expression control region, thereby rendering the retrovirus replication defective. Protocols for producing recombinant retroviruses and for infecting cells in vitro or in vivo with such viruses can be found in Ausubel et al, 1989, "Current Protocols in Molecular Biology," Sections 9.10–9.14, Greene Publishing Associates, and other standard laboratory manuals. Examples of suitable retroviruses include pLJ, pZIP, pWE and pEM, all of which are well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., 1989, Proc. Natl. Acad. Sci. 86: 9079–9083; Julan et al., 1992, J. Gen. Virol. 73: 3251–3255 and Goud et al., 1983, Virology 163: 251–254) or coupling cell surface ligands to the viral env proteins (Neda et al., 1991, J. Biol. Chem. 266: 14143–14146) (all of which are incorporated herein by reference in their entireties). Coupling can be in the form of the chemical cross-linking with a protein or other moiety (e.g., lactose to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., 1988, BioTechniques 6: 616; Rosenfeld et al., 1991, Science 252: 43 1434; and Rosenfeld et al., 1992, Cell 68: 143–155, all of which are incorporated herein by reference in their entireties). Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., 1979, *Cell* 16:683; Berkner et al., supra; and Graham et al., 1991, pp. 109–127 in "Methods in Molecular Biology," vol. 7, E. J. Murray, ed., Humana, Clifton, N.J., all of which are incorporated herein by reference in their entireties). Expression of an inserted gene such as, for example, encoding the human interferon α2b, can be under control of the exogenously added lysozyme gene expression control region sequences.

Yet another viral vector system useful for delivery of, for example, the subject avian lysozyme gene expression control region operably linked to a nucleic acid encoding a polypeptide, is the adeno-associated virus (AAV). Vectors containing as little as 300 base pairs of AAV can be packaged and can integrate. Space for exogenous DNA is limited to about 4.5 kb. An AAV vector, such as that described in Tratschin et al., 1985, *Mol. Cell. Biol.* 5: 3251–3260, can be used to introduce DNA into cells. A variety of nucleic acids have been introduced into different cell types using AAV vectors (see, for example, Hermonat et al., 1984, *Proc. Natl. Acad. Sci.* 81: 6466–6470; Tratschin et al., 1985, *Mol. Cell. Biol.* 4: 2072–2081; Wondisford et al., 1988, *Mol. Endocrinol.* 2: 32–39; Tratschin et al., 1984, *J. Virol.* 51: 611–619; and Flotte et al., 1993, *J. Biol. Chem.* 268: 3781–3790, all of which are incorporated herein by reference in their entireties).

Non-Viral Expression Vectors:

Most non-viral methods of gene transfer rely on normal mechanisms used by eukaryotic cells for the uptake and intracellular transport of macromolecules. In preferred embodiments, non-viral gene delivery systems of the present invention rely on endocytic pathways for the uptake of the subject lysozyme gene expression control region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated lysozyme gene expression control region of the present invention can be entrapped in liposomes bearing positive charges on their surface (e.g., lipofectins) and (optionally) which are tagged with antibodies against cell surface antigens of the target tissue (Mizuno et al., 1992, *NO Shinkei Geka* 20: 547–551; PCT publication WO91/06309; Japanese patent application 1047381; and European patent publication EP-A-43075, all of which are incorporated herein by reference in their entireties).

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180, all of which are incorporated herein by reference in their entireties). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., 1993, *Science* 260–926; Wagner et al., 1992, *Proc. Natl. Acad. Sci.* 89: 7934; and Christiano et al., 1993, *Proc. Natl. Acad. Sci.* 90: 2122, all of which are incorporated herein by reference in their entireties). It is further contemplated that a recombinant DNA molecule comprising the novel isolated lysozyme gene expression control region of the present invention may be delivered to a recipient host cell by other non-viral methods including by gene gun, microinjection, sperm-mediated transfer, or the like.

Transgenic Animals:

Another aspect of the present invention concerns transgenic animals, such as chickens, having a transgene comprising the novel isolated lysozyme gene expression control region of the present invention and which preferably (though optionally) express a heterologous gene in one or more cells in the animal. Suitable methods for the generation of transgenic avians having heterologous DNA incorporated therein are described, for example, in WO 99/19472 to Ivarie et al.; WO 00/11151 to Ivarie et al.; and WO 00/56932 to Harvey et al., all of which are incorporated herein by reference in their entirety.

In various embodiments of the present invention, the expression of the transgene may be restricted to specific subsets of cells, tissues or developmental stages utilizing, for example, cis-acting sequences acting on the lysozyme gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences. The inclusion of a 5 MAR region in the novel isolated lysozyme gene expression control region of the present invention may allow the heterologous expression unit to escape the chromosomal positional effect (CPE) and therefore be expressed at a more uniform level in transgenic tissues that received the transgene by a route other than through germ line cells.

One embodiment of the present invention, therefore, is a transgenic avian having a heterologous polynucleotide sequence comprising a nucleic acid insert encoding the heterologous polypeptide and operably linked to the novel isolated avian lysozyme gene expression control region, the lysozyme gene expression control region comprising at least one 5 matrix attachment region, an intrinsically curved DNA region, at least one transcription enhancer, a negative regulatory element, at least one hormone responsive element, at least one avian CR1 repeat element, and a proximal lysozyme promoter and signal peptide-encoding region.

In an embodiment of the present invention, the transgenic avian is selected from a chicken, a turkey, a duck, a goose, a quail, a pheasant, a ratite, an ornamental bird or a feral bird.

In another embodiment of the present invention, the transgenic avian is a chicken.

In still another embodiment of the transgenic avian of the present invention, the transgenic avian includes an avian lysozyme gene expression control region comprising the nucleic acid sequence in SEQ ID NO: 67, or a degenerate variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In an embodiment of the transgenic avian of the present invention, the polyadenylation signal sequence comprises the nucleic acid sequence in SEQ ID NO: 68, or a degenerate variant thereof.

In still another embodiment of transgenic avian of the present invention, the transgenic avian comprises the chicken lysozyme 3' domain having the nucleic acid sequence SEQ ID NO: 69.

In another embodiment of the transgenic avian of the present invention, the nucleic acid insert encoding a polypeptide has a codon complement optimized for protein expression in an avian.

In yet another embodiment of the transgenic avian of the present invention, the nucleic acid insert encodes an interferon α2b polypeptide.

In still another embodiment of the transgenic avian of the present invention, the nucleic acid insert encoding an interferon α2b polypeptide comprises the sequence in SEQ ID NO: 66, or a degenerate variant thereof.

In one embodiment of the transgenic avian of the present invention, the transgenic avian comprises the nucleotide sequence in SEQ ID NO: 65, or a degenerate variant thereof.

In yet another embodiment of the transgenic avian of the present invention, the transgenic avian comprises the nucleotide sequence in SEQ ID NO: 70, or a degenerate variant thereof. In another embodiment of the transgenic avian of the present invention, the transgenic avian produces the heterologous polypeptide in the serum or an egg white.

In another embodiment of the transgenic avian of the present invention, the transgenic avian produces the heterologous polypeptide in an egg white.

The present invention is further illustrated by the following examples, which are provided by way of illustration and should not be construed as limiting. The contents of all references, published patents and patents cited throughout the present application are hereby incorporated by reference in their entireties.

EXAMPLE 1

Construction of Lysozyme Promoter Plasmids

The chicken lysozyme gene expression control region was isolated by PCR amplification. Ligation and reamplification of the fragments thereby obtained yielded a contiguous nucleic acid construct comprising the chicken lysozyme gene expression control region operably linked to a nucleic acid sequence optimized for codon usage in the chicken (SEQ ID NO: 66) and encoding a human interferon α2b polypeptide optimized for expression in an avian cell.

White Leghorn Chicken (*Gallus gallus*) genomic DNA was PCR amplified using the primers 5pLMAR2 (SEQ ID NO: 1) (see FIG. 1) and LE-6.1 kbrev1 (SEQ ID NO: 2) in a first reaction, and Lys-6.1 (SEQ ID NO: 3) and LysE1rev (SEQ ID NO: 4) as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION™ DNA polymerase (Stratagene, LaJolla, Calif.). The PCR products from these two reactions were gel purified, and then united in a third PCR reaction using only 5pLMAR2 (SEQ ID NO: 1) and LysE1rev (SEQ ID NO: 4) as primers and a 10-minute extension period. The resulting DNA product was phosphorylated, gel-purified, and cloned into the EcoR V restriction site of the vector pBluescript KS, resulting in the plasmid p12.0-lys.

p12.0-lys was used as a template in a PCR reaction with primers 5pLMAR2 (SEQ ID NO: 1) and LYSBSU (SEQ ID NO: 5) and a 10 minute extension time. The resulting DNA was phosphorylated, gel-purified, and cloned into the EcoR V restriction site of pBluescript KS, forming plasmid p12.0lys-B.

p12.0lys-B was restriction digested with Not I and Bsu36 I, gel-purified, and cloned into Not I and Bsu36 I digested pCMV-LysSPIFNMM, resulting in p12.0-lys-LSPIFNMM. p12.0-lys-LSPIFNMM was digested with Sal I and the SalI to NotI primer (SEQ ID NO: 6) was annealed to the digested plasmid, followed by Not I digestion. The resulting 12.5 kb Not I fragment, comprising the lysozyme promoter region linked to IFNMAGMAX-encoding region and an SV40 polyadenylation signal sequence, was gel-purified and ligated to Not I cleaved and dephosphorylated pBluescript KS, thereby forming the plasmid pAVIJCR-A 115.93.1.2. The lysozyme promoter/IFN construct contained in plasmid pAVIJCR-A115.93.1.2 was sequenced as described in Example 3.

EXAMPLE 2

Construction of Plasmids which Contain the 3' Lysozyme Domain

The plasmid pAVIJCR-A 115.93.1.2 was restriction digested with FseI and blunt-ended with T4 DNA polymerase. The linearized, blunt-ended pAVIJCR-A115.93.1.2 plasmid was then digested with XhoI restriction enzyme, followed by treatment with alkaline phosphatase. The resulting 15.4 kb DNA band containing the lysozyme 5' matrix attachment region (MAR) and –12.0 kb lysozyme promoter driving expression of a human interferon was gel purified by electroelution.

The plasmid pIIIilys was restriction digested with MluI, then blunt-ended with the Klenow fragment of DNA polymerase. The linearized, blunt-ended pIIIilys plasmid was digested with XhoI restriction enzyme and the resulting 6 kb band containing the 3' lysozyme domain from exon 3 to the 3' end of the 3' MAR was gel purified by electroelution. The 15.4 kb band from pAVIJCR-A115.93.1.2 and the 6 kb band from pIIIilys were ligated with T4 DNA ligase and transformed into STBL4 cells (Invitrogen Life Technologies, Carlsbad, Calif.) by electroporation. The resulting 21.3 kb plasmids from two different bacterial colonies were named pAVIJCR-A212.89.2.1 and pAVIJCR-A212.89.2.3 respectively.

EXAMPLE 3

Sequencing Reactions

Plasmid DNA (pAVIJCR-A115.93.1.2) produced as described in Example 1 was purified with QIAGEN™ columns (Qiagen, Valencia, Calif.). Sequencing reactions were performed according to the Applied Biosystems (Foster City, Calif.) protocol for BIGDYE™ Terminators, version 2.0, using an ABI 373 Stretch sequencer. Sequencing primers used are listed in FIG. 1, and a schematic diagram illustrating the sequencing reactions using the different primers is shown in FIG. 2. Sequence data was analyzed with SEQUENCHER™ software, version 4.0 (Gene Codes Corp., Ann Arbor, Mich.).

EXAMPLE 4

Complete Lysozyme Promoter and IFNMAGMAX Sequences

The complete nucleotide sequence (SEQ ID NO: 65), shown in FIG. 3, of the 12.5 kb chicken lysozyme promoter region/IFNMAGMAX construct spans the 5' matrix attachment region (5' MAR), through the lysozyme signal peptide, to the sequence encoding the gene IFNMAGMAX and the subsequent polyadenylation signal sequence. The IFNMAGMAX nucleic acid sequence (SEQ ID NO: 66), shown in FIG. 4, encoded human interferon α2b (IFN) that had been synthesized based on a codon usage table compiled from the four most abundantly expressed hen egg white proteins ovalbumen, ovotransferrin, ovomucoid and lysozyme. The expressed IFN α2b sequence within plasmid pAVIJCR-A115.93.1.2 functioned as a reporter gene for lysozyme promoter activity. This plasmid construct may also be used for production of interferon α2b in the egg white of transgenic chickens. The isolated sequence of the 11.94 kb chicken lysozyme promoter region (SEQ ID NO: 67) alone is shown in FIG. 5. The sequence of the SV40 polyadenylation signal sequence (SEQ ID NO: 68) is shown in FIG. 6.

EXAMPLE 5

Basic Local Alignment Search Tool (BLAST) Analysis of the Complete Lysozyme Promoter Sequence (SEQ ID NO: 65)

The complete 12.5 kb lysozyme promoter/IFNMAGMAX sequence (SEQ ID NO: 65) was submitted to the National Center for Biotechnology Information for BLAST alignments with database sequences. Percent identities between the lysozyme promoter sequence (SEQ ID NO: 67, included within SEQ ID NO: 65) and corresponding known lysozyme promoter features are shown in Table II below:

TABLE II

BLAST Results of the Complete 12.0 kb Lysozyme Promoter Sequence

| Description of DNA element | Coordinates in this sequence | GenBank accession number | % identity |
| --- | --- | --- | --- |
| 5' matrix attachment region | 1–237, 261–1564 | AJ277960 | 96 |
| 5' matrix attachment region | 1–237, 261–1564 | X98408 | 96 |
| 5' matrix attachment region | 1564–1912 1930–2015 | X84223 | 99 |
| Intrinsically curved DNA | 2011–2671 | X52989 | 98 |
| Transcription enhancer (−6.1 kb) | 5848–5934 | Grewal et al., 1992 | 100 |
| Transcription enhancer (E-2.7 kb) | 9160–9329 | X05461 | 98 |
| Negative regulatory element | 9325–9626 | X05463 | 98 |
| Hormone response element | 9621–9666 9680–10060 | X12509 | 99 |
| CR1 chicken repeat element | 10576–10821, 10926–11193 | U88211, K02907 | 87 |
| Transcription enhancer (E-0.2 kb) | 11655–11797 | X05462 | 100 |
| Proximal promoter and lysozyme signal peptide | 11563–11877 | M12532 | 100 |
| Proximal promoter and lysozyme signal peptide | 11424–11938 | J00886 | 99 |

Features that have been previously identified as individual elements isolated from other component elements of the lysozyme promoter region include the 5' MAR, three transcription enhancers, a hormone-responsive element, and a chicken repeat 1 (CR1) element. The IFNMAGMAX sequence (SEQ ID NO: 66) extended from nucleotide positions 11946 to 12443 of SEQ ID NO: 65, shown in FIG. 3.

EXAMPLE 6

Expression in Transfected Cultured Avian Oviduct Cells of Human Interferon α2b Regulated by the 12 kb Lysozyme Promoter The oviduct was removed from a Japanese quail (*Coturnix coturnix japonica*) and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and titurating for 30 minutes at 37° C. The cell suspension was then filtered through sterile surgical gauze, washed three times with F-12 medium (Life Technologies, Grand Island, N.Y.) by centrifugation at 200× g, and resuspended in OPTIMEM™ (Life Technologies) such that the $OD_{600}$ was approximately 2. Cell suspension (300 µl) was plated per well of a 24-well dish. For each transfection, 2.5 µl of DMRIE-C liposomes (Life Technologies) and 1 µg of DNA were preincubated for 15 minutes at room temperature in 100 µl of OPTIMEM™, and then added to the oviduct cells. Cells with DNA/liposomes were incubated for 5 hours at 37° C. in 5% $CO_2$. Next, 0.75 ml of DMEM (Life Technologies) supplemented with 15% fetal bovine serum (FBS) (Atlanta Biologicals, Atlanta, Ga.), 2× penicillin/streptomycin (Life Technologies), $10^{-6}$ M insulin (Sigma), $10^{-8}$ M β-estradiol (Sigma), and $10^{-7}$ M corticosterone (Sigma) was added to each well, and incubation was continued for 72 hours. Medium was then harvested and centrifuged at 110×g for 5 minutes. The supernatant was analyzed by ELISA for human interferon α2b content.

The human interferon α2b contents of medium derived from cultured oviduct cells transfected with either the −12.0 kb IFN plasmid (pAVIJCR-A115.93.1.2) or the negative control plasmid pCMV-EGFP as shown in FIG. 7. Bars to the right of the figure represent the standards for the IFN ELISA.

EXAMPLE 7

Transfection of Chicken HD11 Cells with pAVIJCR-A212.89.2.1 and pAVIJCR-A212.89.2.3

Chicken cells transfected with plasmids having the 3 lysozyme domain linked to a nucleic acid expressing human α2b interferon express the heterologous polypeptide. Chicken myelomonocytic HD11 cells were transfected with plasmid pAVIJCR-A212.89.2.1 and pAVIJCR-A212.89.2.3 to test the functionality of the plasmids. One million HD11 cells were plated per each well of a 24-well dish. The next day, HD11 cells were transfected with 1 µg of plasmid DNA per 4 µl of LipofectAMINE 2000 (Invitrogen Life Technologies). For comparison, independent wells were also transfected with the parent vector pAVIJCR-A115.93.1.2. After 5 hours of transfection, the cell medium was changed with fresh medium. 48 hours later, cell medium was harvested by centrifugation at 110×g for 5 min and assayed for human interferon by ELISA (PBL Biomedicals, Flanders, N.J.).

Figure 10:
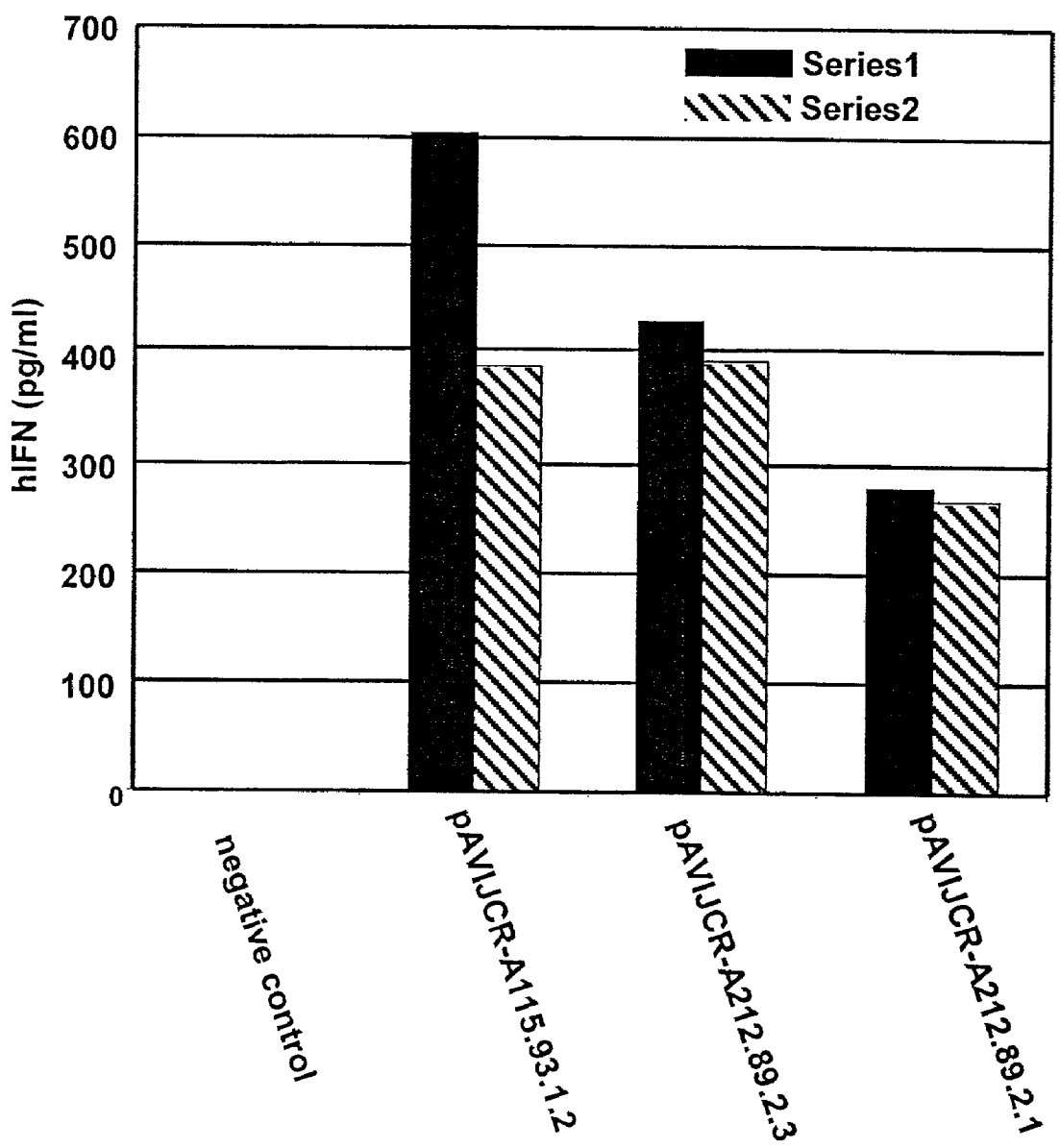
FIG. 10 illustrates the yield of the human interferon α2b, optimized for chicken expression (IFNMAGMAX), in chicken myelomonocytic HD11 cells transfected with plasmids pAVIJCR-A115.93.1.2, pAVIJC-A212.89.2.3 or pAVIJCR-A212.89.2.1.

The transfected cells expressed the heterologous human α2b interferon at least to the level seen with a plasmid not having the 3 lysozyme domain operably linked to the human α2b interferon encoding nucleic acid, as shown in FIG. 10.

EXAMPLE 8

Expression of Human α2b Interferon in a Transgenic Avian Platform

The plasmid pAVIJCR-A115.93.1.2 (containing the −12.0 kb lysozyme promoter controlling expression of human interferon α-2b) was purified with a Qiagen Plasmid Maxi Kit (Qiagen, Valencia, Calif.), and 100 micrograms of the plasmid were restriction digested with NotI restriction enzyme. The digested DNA was phenol/CHCl$_3$ extracted and ethanol precipitated. Recovered DNA was resuspended in 1 mM Tris-HCl (pH 8.0) and 0.1 mM EDTA, then placed overnight at 4° C. DNA was quantified by spectrophotometry and diluted to the appropriate concentration. DNA samples were resuspended in 0.25 M KCl and bound with a SV40 T antigen nuclear localization signal peptide (NLS peptide, amino acid sequence CGGPKKKRKVG-NH$_2$; SEQ ID NO: 71) by adding the NLS at a peptide:DNA molar ratio of 100:1 (Collas and Alestrom, 1996, Mol. Reprod. Develop. 45: 431–438; the contents of which is incoprporated by reference in its entirety).

Cytoplasmic Microinjection of DNA. Approximately two nanoliters of DNA were injected into the germinal disk of stage I White Leghorn embryos obtained two hours after oviposition of the previous egg. DNA amounts per injection ranged from 10 picograms to 400 picograms. Injected embryos were surgically transferred to recipient hens via ovum transfer according to the method of Christmann et al (PCT/US01/26723 to Christmann et al; the contents of which is hereby incorporated by reference in its entirety)

Analysis of chick blood DNA by PCR for IFN transgene: Whole blood from one week old chicks was collected with heparinized capillary tubes. Red blood cell (RBC) nuclei were released and washed with lysis buffer solution. DNA's from RBC nuclei were extracted by digestion with proteinase K (1 mg/ml) and precipitated with ethanol. Purified DNA was resuspended in 1 mM Tris-HCl (pH 8.0) and 0.1 mM EDTA and quantitated. Genomic DNA samples were analysed by PCR using primers LYS051 (SEQ ID NO.: 72) for 5'-TGCATCCTTCAG-CACTTGAG-3' and IFN-3 (SEQ ID NO: 73) for 5'-AACTCCTCTTGAGGAAAGCC-3'. This primer set amplifies a 584 bp region of the transgene carried by the pAVIJCR-A115.93.1.2 plasmid. Three hundred nanograms of genomic DNA were added to a 50 μl reaction mixture (1× Promega PCR Buffer with 1.5 mM MgCl$_2$, 200 μM of each dNTP, 5 μM primers) and 1.25 units of Taq DNA polymerase (Promega). The reaction mixtures were heated for 4 minutes at 94° C., and then amplified for 34 cycles at 94° C. for 1 min, 60° C. for 1 min and 72° C. for 1 min. The samples were heated in a final cycle for 4 minutes at 72° C. PCR products were detected on a 0.8% agarose gel with ethidium bromide staining.

Human interferon α-2b expression in chick blood by ELISA: One week after hatch, blood was collected from chicks using heparinized capillary tubes; added to an equal volume of phosphate buffered saline and centrifuged at 200×g. 100 microliters of the supernatant were assayed by human IFN ELISA (PBL Biomedical Laboratories, New Brunswick, N.J.).

Human interferon α-2b expression in egg white of transgenic hens: once hens reached sexual maturity and began to lay (approximately 22–24 weeks of age), eggs were collected and egg white assayed by ELISA using human IFN ELISA (PBL Biomedical Laboratories, New Brunswick, N.J.) according to maufacturer's instructions.

Results of PCR and ELISA analysis of blood and egg white: Table III below summarizes results of PCR and ELISA analysis.

TABLE III

Analysis of Transgene presence and Interferon Expression

| Bird # | Method | PCR (Blood) | ELISA (Blood) | ELISA (egg white) | # Birds Tested |
|---|---|---|---|---|---|
| 8305 | −NLS | + | + | NA (male) | |
| 8340 | −NLS | − | − | + | 69 (2.5%) |
| AA123 | +NLS | + | + | NA (immature) | |
| AA61 | +NLS | + | + | " | |
| AA105 | +NLS | − | + | " | |
| AA115 | +NLS | + | − | " | 43 (9%) |

Figure 11:
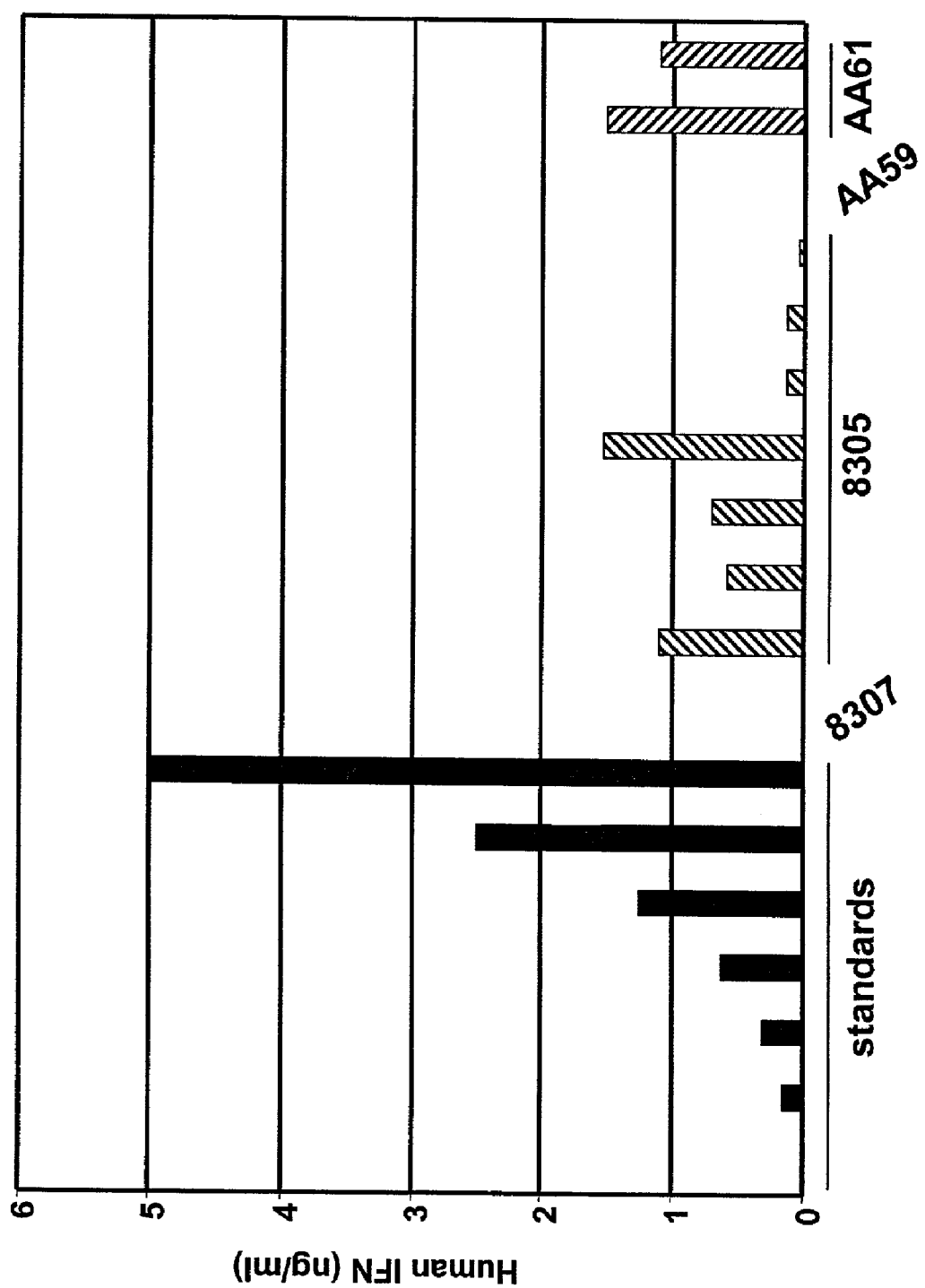
FIG. 11 illustrates the expression of α2b human interferon in the blood of transgenic chickens #8305 and #AA61, as compared to standards.
Figure 12:
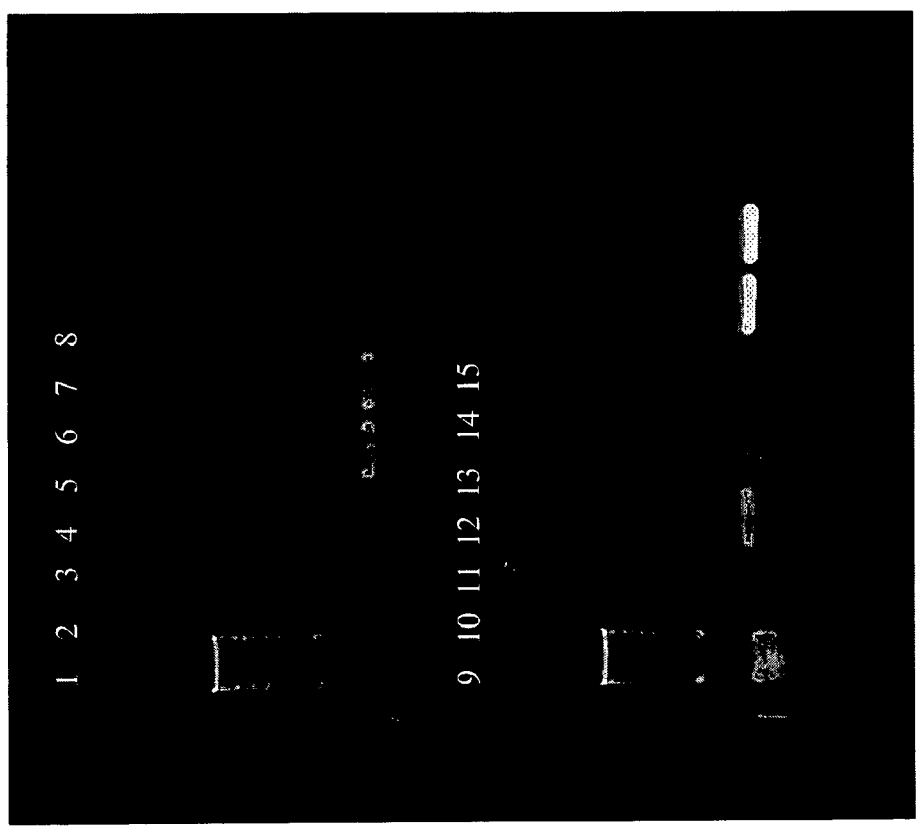
FIG. 12 illustrates the gel analysis of PCR products derived from the serum of transgenic birds. Lane and Samples applied to the gel were: 1, marker; 2, 8301; 3, 8303; 4, 8305; 5, 8305; 6, 8307; 7, 8309; 8, 8311; 9, marker; 10, 8313; 11, 8305; 12, 8305; 13, Neg. Ctrl; 14, Pos. Ctrl (500 pg)+Neg. Ctrl; 15, Pos. Ctrl (500 pg).

−NLS: DNA injected without NLS peptide;
+NLS: DNA injected with NLS peptide;
NA: not applicable As shown in Table III, one bird (#8305) of 69 produced using microinjection of DNA without the NLS peptide, was positive for both presence of the transgene and expression of interferon in the blood. Because this bird is a male, he will be bred to a non-transgenic hen to examine germline transmission of the transgene. FIG. 11 demonstrates expression of human interferon in the blood of #8305, as compared to standards. FIG. 12 illustrates PCR results from the serum of for several birds, including #8305, obtained at different intervals after hatch. As can be seen in lanes 4, 5, 11, and 12, positive signal was seen indicating the presence of the transgene at two different collection periods.

Other positives were seen in birds produced under microinjection of DNA covalently linked to the NLS peptide as described above. Table III illustrates 4 birds (AA123, AA61, AA105 and AA115) out of 43 tested that were PCR positive, ELISA positive or both. Expression levels of human IFN in AA61, as compared to standards, is also illustrated in FIG. 11. Males will be bred to determine germline transmission, and eggs collected from transgenic females to assay for IFN expression, as described above, as chicks reach sexual maturity.

EXAMPLE 9

Expression of a Human Monoclonal Antibody (Mab) in a Transgenic Avian Platform Transgenic chickens were produced as described in Example 8 above, except that two distinct constructs were coinjected into Stage 1 embryos. The constructs comprised the 12 kb lysozyme promoter, as described above in Example 4, driving either a heavy chain or light chain of a human monoclonal antibody against CTLA-4 (WO 01/14424 A2 to Korman et al; the contents of which is incorporated herein in its entirety). ELISA analysis of serum, conducted as described above in Example 8, is summarized below:

TABLE IV

ELISA analysis of Mab expression in hatched birds:

| Bird # | Method | ELISA (serum) | ELISA (egg white) | # Birds Tested |
|---|---|---|---|---|
| 214 | +NLS | + | NA (immature) | |
| 228 | +NLS | + | " | 13 |

+NLS: DNA injected with NLS peptide;
NA: not available

Results indicate that two birds of the thirteen tested to date, #214 and #228, are positive for Mab expression in the serum.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. An isolated cell containing a nucleic acid molecule comprising a gene expression control region which comprises a nucleotide sequence at least 95% identical to the full length of SEQ ID NO:67 operably linked to a polynucleotide encoding a polypeptide heterologous to polypeptides naturally expressed in the cell.

2. The cell of claim 1 wherein the cell is an avian cell.

3. The veil of claim 1 wherein the cell is a chicken cell.

4. The cell of claim 1 wherein the cell is a cultured cell.

5. The cell of claim 1 wherein the cell is an oviduct cell.

6. The cell of claim 1 wherein the cell is a tubular gland cell.

7. The cell of claim 1 wherein the nucleotide sequence is at least 99% identical to the full length of SEQ ID NO:67.

8. The cell of claim 1 wherein the nucleotide sequence is the full length of SEQ ID NO:67.

9. The cell of claim 1 wherein the nucleic acid molecule comprises a 5' matrix attachment region.

10. The cell of claim 1 wherein the nucleic acid molecule comprises an intrinsically curved region of DNA.

11. The cell of claim 1 wherein the nucleic acid molecule comprises a transcription enhancer.

12. The cell of claim 1 wherein the nucleic acid molecule comprises a negative regulatory element.

13. The cell of claim 1 wherein the nucleic acid molecule comprises at least one hormone responsive element.

14. The cell of claim 1 wherein the nucleic acid molecule comprises an avian CRI repeat element.

15. The cell of claim 1 wherein the nucleic acid molecule comprises a proximal lysozyme promoter.

16. The cell of claim 1 wherein the nucleic acid molecule comprises a signal peptide-encoding region.

17. The cell of claim 1 wherein the nucleic acid molecule comprises a polyadenylation signal sequence.

18. The cell of claim 17 wherein the polyadenylation signal sequence is derived from the SV 40 virus.

19. The cell of claim 1 wherein the heterologous polypeptide is a protein of pharmaceutical interest.

20. An isolated avian cell containing an expression vector which comprises a gene expression control region comprising a nucleotide sequence at least 95% identical to the full length of SEQ ID NO:67.

21. The avian cell of claim 20 wherein the cell is a chicken cell.

22. The avian cell of claim 20 wherein the cell is a cultured cell.

23. The avian cell of claim 20 wherein the nucleotide sequence is at least 99% identical to the full length of SEQ ID NO:67.

24. The avian cell of claim 20 wherein the nucleotide sequence is the full length of SEQ ID NO:67.

25. The avian cell of claim 20 wherein the nucleotide sequence is operably linked to a polynucleotide encoding a polypeptide heterologous to polypeptides naturally expressed in the cell.

26. The avian cell of claim 25 wherein the heterologous polypeptide is a protein of pharmaceutical interest.

27. An isolated tubular gland cell containing an expression vector comprising a gene expression control region which comprises a nucleotide sequence at least 95% identical to the full length of SEQ ID NO: 67.

28. The tubular gland cell of claim 27 wherein the cell is an avian cell.

29. The tubular gland cell of claim 27 wherein the cell is a chicken cell.

30. The tubular gland cell of claim 27 wherein the cell is a cultured cell.

31. The tubular gland cell of claim 27 wherein the nucleotide sequence is at least 99% identical to the full length of SEQ ID NO:67.

32. The tubular gland cell of claim 27 wherein the nucleotide sequence is the full length of SEQ ID NO:67.

33. The tubular gland cell of claim 27 wherein the expression vector comprises a 5' matrix attachment region.

34. The tubular gland cell of claim 27 wherein the expression vector comprises an intrinsically tuned region of DNA.

35. The tubular gland cell of claim 27 wherein the expression vector comprises a transcription enhancer.

36. The tubular gland cell of claim 27 wherein the expression vector comprises a negative regulatory element.

37. The tubular gland cell of claim 27 wherein the expression vector comprises at least one hormone responsive element.

38. The tubular gland cell of claim 27 wherein the expression vector comprises an avian CRI repeat element.

39. The tubular gland cell of claim 27 wherein the expression vector comprises at least one of a proximal lysozyme promoter and signal peptide-encoding region.

40. The tubular gland cell of claim 27 wherein the expression vector comprises a polyadenylation signal sequence.

41. The tubular gland cell of claim 40 wherein the polyadenylation signal sequence is derived from the SV 40 virus.

42. The tubular cell of claim 27 wherein the nucleotide sequence is operably linked to a polynucleotide encoding a polypeptide heterologous to polypeptides naturally expressed in the cell.

43. The tubular gland cell of claim 42 wherein the heterologous polypeptide is a protein of pharmaceutical interest.

44. A DNA molecule integrated in an avian cellular genome of an isolated cell comprising a gene expression control region operably linked to a polynucleotide encoding a polypeptide heterologous to polypeptides naturally expressed in the cell wherein the gene expression control region comprises a nucleotide sequence at least 95% identical to the full length of SEQ ID NO: 67.

45. The DNA molecule of claim 44 wherein the cellular genome is that of a chicken cell.

46. The DNA molecule of claim 44 wherein the cellular genome is that of a cultured cell.

47. The DNA molecule of claim 44 wherein the cellular genome is that of an oviduct cell.

48. The DNA molecule of claim 44 wherein the cellular genome is that of a tubular gland cell.

49. The DNA molecule of claim 44 wherein the nucleotide sequence is at least 99% identical to the full length of SEQ ID NO:67.

50. The DNA molecule of claim 44 wherein the nucleotide sequence is the full length of SEQ ID NO:67.

51. The DNA molecule of claim 44 comprising a 5' matrix attachment region.

52. The DNA molecule of claim 44 comprising an intrinsically curved region of DNA.

53. The DNA molecule of claim 44 comprising a transcription enhancer.

54. The DNA molecule of claim 44 comprising a negative regulatory element.

55. The DNA molecule of claim 44 comprising at least one hormone responsive element.

56. The DNA molecule of claim 44 comprising an avian CRI repeat element.

57. The DNA molecule of claim 44 comprising at least one of a proximal lysozyme promoter and signal peptide-encoding region.

58. The DNA molecule of claim 44 comprising a polyadenylation signal sequence.

59. The DNA molecule of claim 58 wherein the polyadenylation signal sequence is derived from the SV 40 virus.

60. The DNA molecule of claim 44 wherein the heterologous polypeptide is a protein of pharmaceutical interest.

* * * * *